United States Patent
Faruki et al.

(10) Patent No.: US 10,829,819 B2
(45) Date of Patent: Nov. 10, 2020

(54) METHODS FOR TYPING OF LUNG CANCER

(71) Applicants: GeneCentric Therapeutics, Inc., Durham, NC (US); The University of North Carolina at Chapel Hill, Chapel Hill, NC (US)

(72) Inventors: Hawazin Faruki, Durham, NC (US); Myla Lai-Goldman, Durham, NC (US); Gregory Mayhew, Durham, NC (US); Charles Perou, Carrboro, NC (US); David Neil Hayes, Chapel Hill, NC (US); Cheng Fan, Chapel Hill, NC (US); Mark Miglarese, Durham, NC (US)

(73) Assignees: GeneCentric Therapeutics, Inc., Durham, NC (US); The University of North Carolina at Chapel Hill, Chapel Hill, NC (US)

( * ) Notice: Subject to any disclaimer, the term of this patent is extended or adjusted under 35 U.S.C. 154(b) by 372 days.

(21) Appl. No.: 15/314,773

(22) PCT Filed: Jun. 1, 2015

(86) PCT No.: PCT/US2015/033611
§ 371 (c)(1),
(2) Date: Nov. 29, 2016

(87) PCT Pub. No.: WO2015/184461
PCT Pub. Date: Dec. 3, 2015

(65) Prior Publication Data
US 2017/0114416 A1    Apr. 27, 2017

Related U.S. Application Data

(60) Provisional application No. 62/005,229, filed on May 30, 2014.

(51) Int. Cl.
*C12Q 1/6886* (2018.01)
(52) U.S. Cl.
CPC ...... *C12Q 1/6886* (2013.01); *C12Q 2600/112* (2013.01); *C12Q 2600/158* (2013.01)
(58) Field of Classification Search
None
See application file for complete search history.

(56) References Cited

U.S. PATENT DOCUMENTS

| | | | |
|---|---|---|---|
| 4,843,155 A | 6/1989 | Chomczynski | |
| 5,384,261 A | 1/1995 | Winker et al. | |
| 5,445,934 A | 8/1995 | Fodor et al. | |
| 5,677,195 A | 10/1997 | Winkler et al. | |
| 5,708,153 A | 1/1998 | Dower et al. | |
| 5,744,305 A | 4/1998 | Fodor et al. | |
| 5,770,358 A | 6/1998 | Dower et al. | |
| 5,770,722 A | 6/1998 | Lockhart et al. | |
| 5,789,162 A | 8/1998 | Dower et al. | |
| 5,800,992 A | 9/1998 | Fodor et al. | |
| 5,856,174 A | 1/1999 | Lipshutz et al. | |
| 5,874,219 A | 2/1999 | Rava et al. | |
| 5,922,591 A | 7/1999 | Anderson et al. | |
| 6,020,135 A | 2/2000 | Levine et al. | |
| 6,033,860 A | 3/2000 | Lockhart et al. | |
| 6,040,138 A | 3/2000 | Lockhart et al. | |
| 6,040,193 A | 3/2000 | Winkler et al. | |
| 6,344,316 B1 | 2/2002 | Lockhart et al. | |
| 7,473,767 B2 | 1/2009 | Dimitrov | |
| 8,492,094 B2 | 7/2013 | Dimitrov et al. | |
| 2006/0024692 A1 | 2/2006 | Nakamura et al. | |
| 2010/0233695 A1 | 9/2010 | Hayes et al. | |
| 2015/0140017 A1 | 5/2015 | Dhodapkar et al. | |

FOREIGN PATENT DOCUMENTS

| | | |
|---|---|---|
| WO | WO 03/029273 A2 | 4/2003 |
| WO | WO 2004/031413 A2 | 4/2004 |
| WO | WO 2008/151110 A2 | 12/2008 |
| WO | WO 2016/168446 A1 | 10/2016 |
| WO | WO 2017/201164 A1 | 11/2017 |
| WO | WO 2017/201165 A1 | 11/2017 |

OTHER PUBLICATIONS

Wilkerson, M.D. et al. Supplemental Figure S2, Journal of Molecular Diagnostics 15(4):485 (Jul. 2013; online May 22, 2013).*
Han, S-S. et al. Lung Cancer 84:229-235. (Year: 2014).*
Kuang, B. et al. Med. Oncol. 30:536. (Year: 2013).*
Dabney, "Classification of microarrays to nearest centroids," Bioinformatics 21(22):4148-4154 (2005).
Ettinger et al., "Non-small cell lung cancer, version 2.2013." J Natl Compr Canc Netw. Jun. 1, 2013, 11(6):645-53; quiz 653.
Friedman et al., "Regularization Paths for Generalized Linear Models via Coordinate Descent," Journal of statistical software 33(1): 1-22 (2010).

(Continued)

*Primary Examiner* — Diana B Johannsen
(74) *Attorney, Agent, or Firm* — Cooley LLP

(57) ABSTRACT

Methods and compositions are provided for the molecular subtyping of lung cancer samples. Specifically, a method of assessing whether a patient's lung cancer subtype is adenocarcinoma, squamous cell carcinoma, or a neuroendocrine (encompassing both small cell carcinoma and carcinoid) is provided herein. A method for assessing whether a patient's lung cancer subtype is adenocarcinoma, squamous cell carcinoma, small cell carcinoma or carcinoid lung cancer is also provided. The methods provided herein entail probing the levels of the classifier biomarkers of Table 1-Table 6 or a subset thereof at the nucleic acid level, in a lung cancer sample obtained from the patient. Based in part on the levels of the classifier biomarkers, the lung cancer sample is classified as a particular lung cancer subtype.

15 Claims, 6 Drawing Sheets
Specification includes a Sequence Listing.

(56) References Cited

OTHER PUBLICATIONS

Rouskin et al., "Genome-wide probing of RNA structure reveals active unfolding of mRNA structures in vivo," Nature 505, pp. 701-705 (2014).
Smyth, G. K., "Linear Models and Empirical Bayes Methods for Assessing Differential Expression in Microarray Experiments," Stat. Appi. Genet. Mol. Biol. 3: Article 3 (2004).
Velculescu et al., "Serial analysis of gene expression," Science 270(5235):484-487 (1995).
American Cancer Society. Cancer Facts and Figures, retrieved Sep. 25, 2018 from https://www.cancer.org/research/cancer-facts-statistics/all-cancer-facts-figures/cancer-facts-figures-2014.html, 6 pages.
Bibikova et al., "Quantitative gene expression profiling in formalin-fixed, paraffin-embedded tissues using universal bead arrays," Am J. Pathol 165:1799-1807 (2004).
Bolstad et al., "A comparison of normalization methods for high density oligonucleotide array data based on variance and bias," Bioinformatics Bioinformatics 19(2):185-193 (2003).
Brenner et al., "Gene expression analysis by massively parallel signature sequencing (MPSS) on microbead arrays," Nat. Biotech. 18:630- 34, 2000.
Broomhead DS, Jones R, King GP., "Comment on Singular-value decomposition and embedding dimension," Phys Rev A Gen Phys. Jun. 15;37(12):5004-5005 (1988).
Cancer Genome Atlas Research Network. "Comprehensive genomic characterization of squamous cell lung cancers." Nature 489.7417 (2012): 519-525.
Cancer Genome Atlas Research Network. Comprehensive molecular profiling of lung adenocarcinoma. Nature 511(7511):543-550 (2014).
Clark et al., "Suppression of nonspecific binding of avidin-biotin complex (ABC) to proteins electroblotted to nitrocellulose paper," J Histochem Cytochem 34:1509-1512.
Cronin et al., "Measurement of gene expression in archival paraffin-embedded tissues: development and performance of a 92-gene reverse transcriptase-polymerase chain reaction assay,"Am. J Pathol. 164(1):35-42 (2004).
Fishel and Kaufman et al., "Meta-analysis of gene expression data: a predictor-based approach," Bioinformatics 23(13): 1599-1606 (2007).
Fox et al., "Formaldehyde Fixation," J Histochem Cytochem 33:845-853 (1985).
Geiss et al., "Direct multiplexed measurement of gene expression with color-coded probe pairs," Nat. Biotechnol. 26, pp. 317-325 (2008).
Grilley-Olson et al., "Validation of interobserver agreement in lung cancer assessment: hematoxylin-eosin diagnostic reproducibility for non-small cell lung cancer: the 2004 World Health Organization classification and therapeutically relevant subsets," Arch Pathol Lab Med 137(1)32-40 (2013).
Hubbell, "Robust estimators for expression analysis," Bioinformatics (2002) 18(12):1585-1592.
Irizarry et al., "Exploration, normalization, and summaries of high density oligonucleotide array probe level data," Biostatistics Apr. 4(2): 249-64 (2003).
Kwoh et al., "Transcription-based amplification system and detection of amplified human immunodeficiency virus type 1 with a bead-based sandwich hybridization format.," Proc. Natl. Acad. Sci. USA, 86:1173 (1989).
Landegren et al., "A ligase-mediated gene detection technique," Science, 241(4869):1077-1080 (1988).
McGhee and von Hippel, "Formaldehyde as a probe of DNA structure. II. Reaction with endocyclic imino groups of DNA bases," Biochemistry 14:1281-1296 1975.
Mullins et al., "Agreement in breast cancer classification between microarray and quantitative reverse transcription PCR from fresh-frozen and formalin-fixed, paraffin-embedded tissues," Clin Chem. 53(7):1273-1279 (2007).
Parzen, "On Estimation of a Probability Density Function and Mode," Stanford University, 1065-1076 (1962).
Quinlan, "Induction of Decision Trees," Machine Learning 1(1):81-106 (1986).
Robin et al., "pROC: an open source package for R and S+ to analyze and compare ROC curves," BMC bioinformatic 12:77 (2011), 8 pages.
Rupp G and Locker J., University of Pittsburgh School of Medicine, "Purification and analysis of RNA from paraffin embedded tissues," BioTechniques 6(1):56-60 (1988).
Smyth, G. K., Limma: linear models for microarray data. In: Bioinformatics and Computational Biology Solutions using Rand Bioconductor, R. Gentleman, V. Carey, S. Dudoit, R.Irizarry, W. Huber (eds.), Springer, New York, pp. 397-420 (2005).
Suykens JAK, Vandewalle J., "Least Squares Support Vector Machine Classifiers," Neural Processing Letters 9(3): 293-300 (1999).
Szumilas, "Explaining odds ratios," J. Can. Acad. Child Adolesc. Psychiatry 19(3): 227-229 (2010).
Tang et al., "Advances in lung adenocarcinoma classification: a summary of the new international multidisciplinary classification system (IASLC/ATS/ERS) ," J Thorac Dis 2014; 6(S5):S489-S501.
Thunnissen et al., "Reproducibility of histopathological subtypes and invasion in pulmonary adenocarcinoma. An international interobserver study," Mod Pathol 2012; 25(12):1574-1583. Doi: 10.1038/modpathol.2012.106 Epub Jul. 20, 2012.
Thunnissen et al., "Correlation of immunohistochemical staining p63 and TTF-1 with EGFR and K-ras mutational spectrum and diagnostic reproducibility in non small cell lung carcinoma," Virchows Arch 2012; 46(6)1:629-38.
Tibshirani et al., "Diagnosis of multiple cancer types by shrunken centroids of gene expression," Proc. Natl. Acad. Sci. USA 99(10):6576-6572) (2002).
Trapnell et al., "TopHat: discovering splice junctions with RNA-Seq.," Bioinformatics 25(9):1105-11 (2009).
Travis et al., "Diagnosis of lung cancer in small biopsies and cytology: implications of the 2011 International Association for the Study of Lung Cancer/American Thoracic Society/European Respiratory Society classification," Arch Pathol Lab Med 2013; 137(5):668-84.
Travis and Rekhtman, "Pathological diagnosis and classification of lung cancer in small biopsies and cytology: strategic management of tissue for molecular testing," Sem Resp and Crit Care Med 2011; 32(1): 22-31.
Velculescu et al., "Characterization of the yeast transcriptome," Cell 88(2):243-51 (1997).
Wilkerson et al., "Prediction of lung cancer histological types by RT-qPCR gene expression in FFPE specimens," J Molec Diagn 15(4):485-497 (2013).
Wu and Wallace, "The ligation amplification reaction (LAR)—amplification of specific DNA sequences using sequential rounds of template-dependent ligation," Genomics, 4(4):560-569 (1989).
Yang et al, "Normalization for cDNA microarray data: a robust composite method addressing single and multiple slide systematic variation,"Feb. 15, 2002;30(4):e15, 10 pages.
ALIMTA® (Pemetrexed disodium) Eli Lilly & Co., Indianapolis, IN prescribing information. http://pi.lilly.com/us/alimta-pi.pdf, 31 pages (2018).
AVASTIN® (Bevacizumab) Genentech Inc, San Francisco, CA prescribing information (2018). Retrieved online Oct. 10, 2018 at https://www.gene.com/download/pdf/avastin_prescribing.pdf, 41 pages.
Barany, "Cloning, overexpression and nucleotide sequence of a thermostable DNA ligase-encoding gene," Proc. Natl. Acad. Sci. USA 88:189-193 (1991).
Bild AH, Yao G, Chang JT, et al. Oncogenic pathway signatures in human cancers as a guide to targeted therapies. Nature 439(7074): 353-357 (2006).
Bindea et al., "Spatiotemporal dynamics of intratumoral immune cells reveal the immune landscape in human cancer," Immunity 39(4); 782-795 (2013).
Calabrese et al., "Serpin B4 Isoform Overexpression is Associated with Aberrant Epithelial Proliferation and Lung Cancer in Idiopathic Pulmonary Fibrosis," Pathology 44(3):192-198 (2012).
Cao et al "Role of LKBl-CRTCl on glycosylated COX-2 and response to COX-2 inhibition in lung cancer," J Natl Cancer Inst. 107(1):1-11 (2015).

(56) References Cited

OTHER PUBLICATIONS

Dabney AR ClaNC: Point-and-click software for classifying microarrays to nearest centroids. Bioinformatics. 2006;22: 122-123.
Extended European Search Report issued by the European Patent Office for Application No. 16780736.1, dated Nov. 9, 2018, 13 pages.
Fan et al., "A Versatile Assay for High-Throughput Gene Expression Profiling on Universal Array Matrices," Genome Res. 14:878-885 (2004).
Faruki et al., "Lung Adenocarcinoma and Squamous Cell Carcinoma Gene Expression Subtypes Demonstrate Significant Differences in Tumor Immune Landscape," Journal of Thoracic Oncology 12(6):943-953 (2017).
Faruki H, et al., "Validation of the Lung Subtyping Panel in Multiple Fresh-Frozen and Formalin-Fixed, Paraffin-Embedded Lung Tumor Gene Expression Data Sets," Archives Path & Lab Med. Oct. 2015.
Fennell et al., "Association between Gene Expression Profile and Clinical Outcome of Pemetrexed-Based Treatment in Patients ,with Advanced Non-Small Cell Lung Cancer: Exploratory Results from a Phase II study," PLOS one 2014; Sep. 14 9(9): el07455, 8 pages.
Forero et al., "Expression of the MHC class II pathway in triple negative breast cancer tumor cells is associated with a good prognosis and infiltrating lymphocytes," Cancer Immunol Res 4(5):390-399 2016.
Foundation Medicine Solid Tumor Mutation Panel accessed Oct. 2014, 2 pages.
Grilley-Olson et al. Validation of interobserver agreement in lung cancer assessment: hematoxylin-eosin diagnostic reproducibility for non-small cell lung cancer. Arch Pathol Lab Med 2013; 137: 32-40.
Guatelli et al., "Isothermal, in vitro amplification of nucleic acids by a multienzyme reaction modeled after retroviral replication," Proc Natl Acad Sci U S A. 87(5):1874-1878 (1990).
Hast et al., Cancer-derived mutations in KEAPI impair NRF2 degradation but not ubiquitination. Cancer Res 2014; 74(3): 808-817.
Hayes DN, Monti S, Parmigiani G, et al. Gene expression profiling reveals reproducible human lung adenocarcinoma subtypes in multiple independent patient cohorts. J Clin Oncol 24(31): 5079-5090 (2006).
International Search Report and Written Opinion issued by the International Searching Authority for Application No. PCT/US2015/033611, dated Sep. 14, 2015, 10 pages.
International Search Report and Written Opinion issued by the International Searching Authority for Application No. PCT/US2016/027503, dated Jul. 14, 2016, 10 pages.
International Search Report and Written Opinion issued by the International Searching Authority for Application No. PCT/US2017/033107, dated Oct. 23, 2017, 21 pages.
International Search Report and Written Opinion issued by the International Searching Authority for Application No. PCT/US2017/033110, dated Oct. 20, 2017, 21 pages.
Koyama et al., STKI1/LKBI deficiency promotes neutrophil recruitment and proinflammatory cytokine production to suppress T-cell activity in the lung tumor microenvironment. Cancer Res 76(5): 999-1008 (2016).
Kratz JR, et al., "A practical molecular assay to predict survival in resected non-squamous, non-small-cell lung cancer: development and international validation studies," Lancet 379(9818):823-832 (2012).
Li and Dewey, "RSEM: accurate transcript quantification from RNA-Seq data with or without a reference genome," BMC Bioinformatics 2011 12:323, 16 pages.
Mukhopadhyay S., "Utility of Small Biopsies for Diagnosis of Lung Nodules: Doing More with Less," Modern Pathology, 25(1):S43-S57 (2012).
Nielsen, "A comparison of PAM50 intrinsic subtyping with immunohistochemistry and clinical prognostic factors in tamoxifen-treated estrogen receptor-positive breast cancer," Clin Cancer Res. Nov. 1, 2010;16(21):5222-32. doi: 10.1158/1078-0432.CCR-10-1282. Epub Sep. 13, 2010, Downloaded from clincancerres.aacrjournals.org on Oct. 10, 2018.
Niki, T., et al., "Expression of Vascular Endothelial Growth Factors A, B. C, and D and Their Relationships to Lymph Node Status in Lung Adenocarcinoma," Clinical Cancer Research 6(6):2431-2439 (2000).
Paolillo et al., "Small molecule integrin antagonists in cancer therapy," Mini Rev Med Chem 12:1439-1446 (2009).
Prasad et al., "Differential Expression of Degradome Components in Cutaneous Squamous Cell Carcinomas," Modern Pathology 27:495-957 (2014).
Raponi et al. "Gene expression signatures for predicting prognosis of squamous cell and adenocarcinomas of the lung," Cancer Res 66(7): 466-472 (2006).
Rekhtman et al., "Distinct profile of driver mutations and clinical features in immunomarker-defined subsets of pulmonary large-cell carcinoma," Mod Pathol 26(4): 511-22 (2013).
Rekhtman et al., "Immunnohistochemical algorithm for differentiation of lung adenocarcinoma and squamous cell carcinoma based on large series of whole-tissue sections with validation in small specimens," Modern Path. 24:1348-1359 (2011).
Ringnér, M., et al., "Prognostic and Chemotherapy Predictive Value of Gene-Expression Phenotypes in Primary Lung Adenocarcinoma," Clinical Cancer Research 22(1):218-229 (2015).
Roepman P, et al. An immune response enriched 72-gene prognostic profile for early-stage non-small-cell lung cancer. Clinical Cancer Research 15.1:284-290 (2009).
Rossi G, Mengoli MC, Cavazza A, et al. Large cell carcinoma of the lung: clinically oriented classification integrating immunohistochemistry and molecular biology. Virchows Arch. 2014; 464: 61-68. DOI 10.1007/s00428-013-1501-6.
Rousseaux S, et al. Ectopic activation of germline and placental genes identifies aggressive metastasis-prone lung cancers. Sci Transl Med. 5(186):186ra66 (2013).
Schabath et al., "Differential association of STKI1 and TP53 with KRAS mutation-associated gene expression, proliferation, and immune surveillance in lung adenocarcinoma," Oncogene 35(24):3209-3216, Author manuscript, 13 pages (2016).
Schafer, G., et al., *Homo sapiens* Vascular Endothelial Growth Factor D (FIGF) Gene, Promoter Region and 5' UTR. National Center for Biotechnology Information. Genbank Entry. Jan. 3, 2005 [retrieved on Sep. 27, 2017] Retrieved from the Internet: <URL: https://www.ncbi.nlm.nih.gov/nucleotide/58223364?report=genbank&log$=nuclalign&blast_rank=5&RID=WWYAJBVM015>; pp. 1-2.
Shedden K, Taylor JMG, Enkemann SA, et al. Gene expression-based survival prediction in lung adenocarcinoma: a multi-site, blinded validation study: director's challenge consortium for the molecular classification of lung adenocarcinoma. Nat Med 14(8): 822-827 (2008). doi: 10.1038/nm. 1790.
Skoulidis et al., "Co-occuring genomic alterations define major subsets of KRAS-mutant lung adenocarcinoma with distinct biology, immune profiles, and therapeutic vulnerabilities," Cancer Discov 5(8): 860-77 (2015).
Statistical analyses R 3.2.0 software (http://www.R-project.org) retrieved online Jan. 7, 2019 at http://www.R-project.org, 3 pages.
The Clinical Lung Cancer Genome Project (CLCGP) and Network Genomic Medicine (NGM). A genomics-based classification of human lung tumors. Sci Transl Med 5, 209ra153, 28 pages (2013).
Thunnissen et al., "Reproducibility of histopathological diagnosis in poorly differentiated NSCLC: an international multiobserver study," J Thorac Oncol 2014; 9(9): 1354-1362.
Tomida S., et al "Relapse-related molecular signature in lung adenocarcinomas identifies patients with dismal prognosis," J Clin Oncol 27(17): 2793-99 (2009).
Trapnell et al., "Transcript assembly and quantification by RNA-Seq reveals unannotated transcripts and isoform switching during cell differentiation," Nature biotechnology 28(5):511-515 (2010).
Travis et al., "International Association for the study of lung cancer/American Thoracic Society/European Respiratory Society International multidisciplinary classification of lung adenocarcinoma," J Thorac Oncol, 6:244-285 (2011).

(56) References Cited

OTHER PUBLICATIONS

Travis et al., "New pathologic classification of lung cancer: relevance for clinical practice and clinical trials," J Clin Oncol 31:992-1001 (2013).

Vermeulen, Pediatric Primitive Neuroectodermal Tumors of the Central Nervous System Differentially Express Granzyme Inhibitors. PLoS One. 11(3):1-8 (2016).

Wilkerson et al., Lung Squamous Cell Carcinoma mRNA Expression Subtypes are Reproducible, Clinically Important and Correspond to Different Normal Cell Types. Clinical Clin Cancer Res 16(19):4864-4875 (2010).

Wilkerson et al., "Differential pathogenesis of lung adenocarcinoma subtypes involving sequence mutations, copy number, chromosomal instability, and methylation," PLoS ONE. 2012; 7(5) e36530. Doi:10.1371/journal.pone.0036530, 13 pages.

Wistuba et al., ""Validation of a proliferation-based expression signature as prognostic marker in early stage lung adenocarcinoma,"" Clin Cancer Res 19(22):6261-6271 (2013), Downloaded from clincancerres.aacrjournals.org on Oct. 10, 2018.

Wold, et al., "Genome expression and mRNA maturation at late stages of productive adenovirus type 2 infection," J Virol. Nov. 1976;20(2):465-77.

Zhang et al., "Assessment of VEGF-D Expression Measured by Immunohistochemical Staining and F-18 FDG Uptake on PET as Biological Prognostic Factors for Recurrence in Patients with Surgically Resected Lung Adenocarcinoma," Annals of Nuclear Medicine. 24(7):533-540 (2010).

Zhu CQ, et al., "Prognostic and predictive gene signature for adjuvant chemotherapy in resected non-small-cell lung cancer," J Clin Oncol 28(29); 4417-4424 (2010).

\* cited by examiner

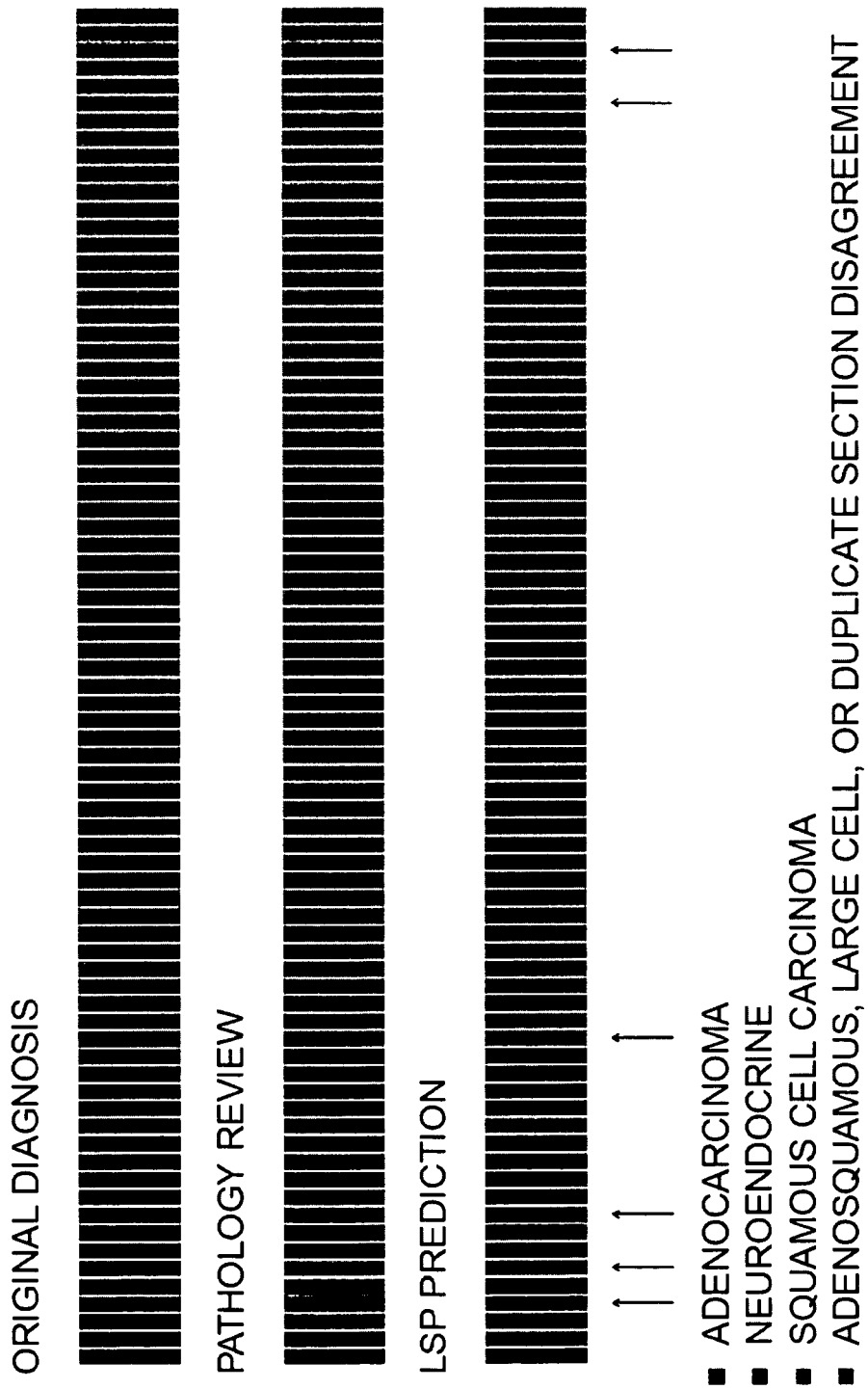

SEQUENCE LISTING

```
<160> NUMBER OF SEQ ID NOS: 114

<210> SEQ ID NO 1
<211> LENGTH: 22
<212> TYPE: DNA
<213> ORGANISM: Homo sapiens

<400> SEQUENCE: 1
aagagagatt ggatttggaa cc                                             22

<210> SEQ ID NO 2
<211> LENGTH: 22
<212> TYPE: DNA
<213> ORGANISM: Homo sapiens

<400> SEQUENCE: 2
ccagaagccc aagaagattg ta                                             22

<210> SEQ ID NO 3
<211> LENGTH: 19
<212> TYPE: DNA
<213> ORGANISM: Homo sapiens

<400> SEQUENCE: 3
aatcctggtg tcaaggaag                                                 19

<210> SEQ ID NO 4
<211> LENGTH: 19
<212> TYPE: DNA
<213> ORGANISM: Homo sapiens

<400> SEQUENCE: 4
ggaccgattt taccgatcc                                                 19

<210> SEQ ID NO 5
<211> LENGTH: 21
<212> TYPE: DNA
<213> ORGANISM: Homo sapiens

<400> SEQUENCE: 5
acagtccaga tagtcgtatg t                                              21
```

-continued

```
<210> SEQ ID NO 6
<211> LENGTH: 17
<212> TYPE: DNA
<213> ORGANISM: Homo sapiens

<400> SEQUENCE: 6
gtctccgcca tccctat                                                    17

<210> SEQ ID NO 7
<211> LENGTH: 19
<212> TYPE: DNA
<213> ORGANISM: Homo sapiens

<400> SEQUENCE: 7
actggtgtaa caggaacat                                                  19

<210> SEQ ID NO 8
<211> LENGTH: 17
<212> TYPE: DNA
<213> ORGANISM: Homo sapiens

<400> SEQUENCE: 8
tttggaagga ctgcgct                                                    17

<210> SEQ ID NO 9
<211> LENGTH: 17
<212> TYPE: DNA
<213> ORGANISM: Homo sapiens

<400> SEQUENCE: 9
cacgtcatct cccgttc                                                    17

<210> SEQ ID NO 10
<211> LENGTH: 18
<212> TYPE: DNA
<213> ORGANISM: Homo sapiens

<400> SEQUENCE: 10
attgaacttc ccacacga                                                   18

<210> SEQ ID NO 11
<211> LENGTH: 18
<212> TYPE: DNA
<213> ORGANISM: Homo sapiens

<400> SEQUENCE: 11
ggaacagact gtcaccat                                                   18

<210> SEQ ID NO 12
<211> LENGTH: 19
<212> TYPE: DNA
<213> ORGANISM: Homo sapiens

<400> SEQUENCE: 12
tcagagtgtg tggtcaggc                                                  19

<210> SEQ ID NO 13
<211> LENGTH: 17
<212> TYPE: DNA
<213> ORGANISM: Homo sapiens

<400> SEQUENCE: 13
gggacagctt caacact                                                    17
```

-continued

```
<210> SEQ ID NO 14
<211> LENGTH: 18
<212> TYPE: DNA
<213> ORGANISM: Homo sapiens

<400> SEQUENCE: 14
cctgtgaaca gccctatg                                                 18

<210> SEQ ID NO 15
<211> LENGTH: 17
<212> TYPE: DNA
<213> ORGANISM: Homo sapiens

<400> SEQUENCE: 15
ttctgggcac ggtgaag                                                  17

<210> SEQ ID NO 16
<211> LENGTH: 21
<212> TYPE: DNA
<213> ORGANISM: Homo sapiens

<400> SEQUENCE: 16
ggccaaacta gagcacgaat a                                             21

<210> SEQ ID NO 17
<211> LENGTH: 19
<212> TYPE: DNA
<213> ORGANISM: Homo sapiens

<400> SEQUENCE: 17
tcagcaagaa ggagatgcc                                                19

<210> SEQ ID NO 18
<211> LENGTH: 21
<212> TYPE: DNA
<213> ORGANISM: Homo sapiens

<400> SEQUENCE: 18
gtgctccctc tccattaagt a                                             21

<210> SEQ ID NO 19
<211> LENGTH: 20
<212> TYPE: DNA
<213> ORGANISM: Homo sapiens

<400> SEQUENCE: 19
caagttcagg agaactcgac                                               20

<210> SEQ ID NO 20
<211> LENGTH: 19
<212> TYPE: DNA
<213> ORGANISM: Homo sapiens

<400> SEQUENCE: 20
ggctgtggtt atgcgatag                                                19

<210> SEQ ID NO 21
<211> LENGTH: 18
<212> TYPE: DNA
<213> ORGANISM: Homo sapiens

<400> SEQUENCE: 21
acccgaggaa caaccttta                                                18
```

<210> SEQ ID NO 22
<211> LENGTH: 18
<212> TYPE: DNA
<213> ORGANISM: Homo sapiens

<400> SEQUENCE: 22
ccctctccat tccctaca                                                18

<210> SEQ ID NO 23
<211> LENGTH: 17
<212> TYPE: DNA
<213> ORGANISM: Homo sapiens

<400> SEQUENCE: 23
cagagcgcca ggcatta                                                 17

<210> SEQ ID NO 24
<211> LENGTH: 18
<212> TYPE: DNA
<213> ORGANISM: Homo sapiens

<400> SEQUENCE: 24
ccactggctg aggtgtta                                                18

<210> SEQ ID NO 25
<211> LENGTH: 17
<212> TYPE: DNA
<213> ORGANISM: Homo sapiens

<400> SEQUENCE: 25
tgggcgagtc tacgatg                                                 17

<210> SEQ ID NO 26
<211> LENGTH: 18
<212> TYPE: DNA
<213> ORGANISM: Homo sapiens

<400> SEQUENCE: 26
ctttctgccc tggagatg                                                18

<210> SEQ ID NO 27
<211> LENGTH: 19
<212> TYPE: DNA
<213> ORGANISM: Homo sapiens

<400> SEQUENCE: 27
gcgccatttg ctagagata                                               19

<210> SEQ ID NO 28
<211> LENGTH: 19
<212> TYPE: DNA
<213> ORGANISM: Homo sapiens

<400> SEQUENCE: 28
agagaagatg ggcagaaag                                               19

<210> SEQ ID NO 29
<211> LENGTH: 17
<212> TYPE: DNA
<213> ORGANISM: Homo sapiens

<400> SEQUENCE: 29

-continued gcccagatca tccgtca                                                  17

<210> SEQ ID NO 30
<211> LENGTH: 17
<212> TYPE: DNA
<213> ORGANISM: Homo sapiens

<400> SEQUENCE: 30
accacaagga cttcgac                                                  17

<210> SEQ ID NO 31
<211> LENGTH: 17
<212> TYPE: DNA
<213> ORGANISM: Homo sapiens

<400> SEQUENCE: 31
gctccgctgc tatcttt                                                  17

<210> SEQ ID NO 32
<211> LENGTH: 17
<212> TYPE: DNA
<213> ORGANISM: Homo sapiens

<400> SEQUENCE: 32
agcggccagg tggatta                                                  17

<210> SEQ ID NO 33
<211> LENGTH: 18
<212> TYPE: DNA
<213> ORGANISM: Homo sapiens

<400> SEQUENCE: 33
atgggctttg ggagcata                                                 18

<210> SEQ ID NO 34
<211> LENGTH: 18
<212> TYPE: DNA
<213> ORGANISM: Homo sapiens

<400> SEQUENCE: 34
gacctggatg ccaagcta                                                 18

<210> SEQ ID NO 35
<211> LENGTH: 17
<212> TYPE: DNA
<213> ORGANISM: Homo sapiens

<400> SEQUENCE: 35
ccggctcttg gaagttg                                                  17

<210> SEQ ID NO 36
<211> LENGTH: 20
<212> TYPE: DNA
<213> ORGANISM: Homo sapiens

<400> SEQUENCE: 36
acgcggatcg agtttgataa                                               20

<210> SEQ ID NO 37
<211> LENGTH: 17
<212> TYPE: DNA
<213> ORGANISM: Homo sapiens

<400> SEQUENCE: 37
cgcaagtccc agaagat           17

<210> SEQ ID NO 38
<211> LENGTH: 17
<212> TYPE: DNA
<213> ORGANISM: Homo sapiens

<400> SEQUENCE: 38
cgcggatacg atgtcac           17

<210> SEQ ID NO 39
<211> LENGTH: 17
<212> TYPE: DNA
<213> ORGANISM: Homo sapiens

<400> SEQUENCE: 39
gaactcggcc tatcgct           17

<210> SEQ ID NO 40
<211> LENGTH: 20
<212> TYPE: DNA
<213> ORGANISM: Homo sapiens

<400> SEQUENCE: 40
tctgacctca tcatcggcaa        20

<210> SEQ ID NO 41
<211> LENGTH: 20
<212> TYPE: DNA
<213> ORGANISM: Homo sapiens

<400> SEQUENCE: 41
gaggtgaagc aaactacgga        20

<210> SEQ ID NO 42
<211> LENGTH: 17
<212> TYPE: DNA
<213> ORGANISM: Homo sapiens

<400> SEQUENCE: 42
actctccaca aagctcg           17

<210> SEQ ID NO 43
<211> LENGTH: 22
<212> TYPE: DNA
<213> ORGANISM: Homo sapiens

<400> SEQUENCE: 43
ggatttcagc taccagttac tt     22

<210> SEQ ID NO 44
<211> LENGTH: 17
<212> TYPE: DNA
<213> ORGANISM: Homo sapiens

<400> SEQUENCE: 44
ttcgtcctgg tggatcg           17

<210> SEQ ID NO 45
<211> LENGTH: 22
<212> TYPE: DNA
<213> ORGANISM: Homo sapiens

```
<400> SEQUENCE: 45
agtgattgat gtgtttgcta tg                                    22

<210> SEQ ID NO 46
<211> LENGTH: 20
<212> TYPE: DNA
<213> ORGANISM: Homo sapiens

<400> SEQUENCE: 46
caaagccaag ccactcactc                                       20

<210> SEQ ID NO 47
<211> LENGTH: 17
<212> TYPE: DNA
<213> ORGANISM: Homo sapiens

<400> SEQUENCE: 47
ctcggcagtc ctgtttc                                          17

<210> SEQ ID NO 48
<211> LENGTH: 18
<212> TYPE: DNA
<213> ORGANISM: Homo sapiens

<400> SEQUENCE: 48
acacctggta cgtcagaa                                         18

<210> SEQ ID NO 49
<211> LENGTH: 20
<212> TYPE: DNA
<213> ORGANISM: Homo sapiens

<400> SEQUENCE: 49
atgcccaaga gaatcgtaaa                                       20

<210> SEQ ID NO 50
<211> LENGTH: 19
<212> TYPE: DNA
<213> ORGANISM: Homo sapiens

<400> SEQUENCE: 50
atgagtccaa agcacacga                                        19

<210> SEQ ID NO 51
<211> LENGTH: 22
<212> TYPE: DNA
<213> ORGANISM: Homo sapiens

<400> SEQUENCE: 51
tgagattgag gatgaagctg ag                                    22

<210> SEQ ID NO 52
<211> LENGTH: 17
<212> TYPE: DNA
<213> ORGANISM: Homo sapiens

<400> SEQUENCE: 52
ccgactcaac gtgagac                                          17

<210> SEQ ID NO 53
<211> LENGTH: 17
<212> TYPE: DNA
<213> ORGANISM: Homo sapiens
```

```
<400> SEQUENCE: 53
gtgccctctc cttttcg                                                17

<210> SEQ ID NO 54
<211> LENGTH: 18
<212> TYPE: DNA
<213> ORGANISM: Homo sapiens

<400> SEQUENCE: 54
cgttcttttt cgcaacgg                                               18

<210> SEQ ID NO 55
<211> LENGTH: 17
<212> TYPE: DNA
<213> ORGANISM: Homo sapiens

<400> SEQUENCE: 55
ggtgtgccac tgaagat                                                17

<210> SEQ ID NO 56
<211> LENGTH: 17
<212> TYPE: DNA
<213> ORGANISM: Homo sapiens

<400> SEQUENCE: 56
gtgtcgtggt ggtcatt                                                17

<210> SEQ ID NO 57
<211> LENGTH: 17
<212> TYPE: DNA
<213> ORGANISM: Homo sapiens

<400> SEQUENCE: 57
gcatgaagac agtggct                                                17

<210> SEQ ID NO 58
<211> LENGTH: 17
<212> TYPE: DNA
<213> ORGANISM: Homo sapiens

<400> SEQUENCE: 58
ttcttgcgac tcacgct                                                17

<210> SEQ ID NO 59
<211> LENGTH: 24
<212> TYPE: DNA
<213> ORGANISM: Homo sapiens

<400> SEQUENCE: 59
gctcctcaaa catctttgtg ttca                                        24

<210> SEQ ID NO 60
<211> LENGTH: 20
<212> TYPE: DNA
<213> ORGANISM: Homo sapiens

<400> SEQUENCE: 60
gaccactgtg ggtcattatt                                             20

<210> SEQ ID NO 61
<211> LENGTH: 17
<212> TYPE: DNA
```

```
<213> ORGANISM: Homo sapiens

<400> SEQUENCE: 61
gaaatctctg gccgctc                                                  17

<210> SEQ ID NO 62
<211> LENGTH: 21
<212> TYPE: DNA
<213> ORGANISM: Homo sapiens

<400> SEQUENCE: 62
actgggcatc ataagaaatc c                                             21

<210> SEQ ID NO 63
<211> LENGTH: 19
<212> TYPE: DNA
<213> ORGANISM: Homo sapiens

<400> SEQUENCE: 63
actgaacaga agacttcgt                                                19

<210> SEQ ID NO 64
<211> LENGTH: 20
<212> TYPE: DNA
<213> ORGANISM: Homo sapiens

<400> SEQUENCE: 64
aacctccaag tggaaattct                                               20

<210> SEQ ID NO 65
<211> LENGTH: 22
<212> TYPE: DNA
<213> ORGANISM: Homo sapiens

<400> SEQUENCE: 65
tcggtctttc aaatcgggat ta                                            22

<210> SEQ ID NO 66
<211> LENGTH: 18
<212> TYPE: DNA
<213> ORGANISM: Homo sapiens

<400> SEQUENCE: 66
ctgctgtcac aggacaat                                                 18

<210> SEQ ID NO 67
<211> LENGTH: 19
<212> TYPE: DNA
<213> ORGANISM: Homo sapiens

<400> SEQUENCE: 67
aaggtaaagc cagactcca                                                19

<210> SEQ ID NO 68
<211> LENGTH: 17
<212> TYPE: DNA
<213> ORGANISM: Homo sapiens

<400> SEQUENCE: 68
gggagcgtag ggttaag                                                  17

<210> SEQ ID NO 69
<211> LENGTH: 22
```

```
<212> TYPE: DNA
<213> ORGANISM: Homo sapiens

<400> SEQUENCE: 69
cagtgtattc tgcacaatca ac                                              22

<210> SEQ ID NO 70
<211> LENGTH: 21
<212> TYPE: DNA
<213> ORGANISM: Homo sapiens

<400> SEQUENCE: 70
gttccaggat gttggactttt c                                              21

<210> SEQ ID NO 71
<211> LENGTH: 18
<212> TYPE: DNA
<213> ORGANISM: Homo sapiens

<400> SEQUENCE: 71
ggaaagtgtg tcggagat                                                   18

<210> SEQ ID NO 72
<211> LENGTH: 18
<212> TYPE: DNA
<213> ORGANISM: Homo sapiens

<400> SEQUENCE: 72
aggcaacatc attccctc                                                   18

<210> SEQ ID NO 73
<211> LENGTH: 22
<212> TYPE: DNA
<213> ORGANISM: Homo sapiens

<400> SEQUENCE: 73
gtcaacaccc atcttcttga aa                                              22

<210> SEQ ID NO 74
<211> LENGTH: 18
<212> TYPE: DNA
<213> ORGANISM: Homo sapiens

<400> SEQUENCE: 74
cgtagtggaa gacggaaa                                                   18

<210> SEQ ID NO 75
<211> LENGTH: 23
<212> TYPE: DNA
<213> ORGANISM: Homo sapiens

<400> SEQUENCE: 75
ctggtgtaga attaggagac gta                                             23

<210> SEQ ID NO 76
<211> LENGTH: 17
<212> TYPE: DNA
<213> ORGANISM: Homo sapiens

<400> SEQUENCE: 76
ggcatcaaga gagaggc                                                    17

<210> SEQ ID NO 77
```

```
<211> LENGTH: 24
<212> TYPE: DNA
<213> ORGANISM: Homo sapiens

<400> SEQUENCE: 77
gataaagagt tacaagctcc tctg                                          24

<210> SEQ ID NO 78
<211> LENGTH: 17
<212> TYPE: DNA
<213> ORGANISM: Homo sapiens

<400> SEQUENCE: 78
tctaggcctt gacggat                                                  17

<210> SEQ ID NO 79
<211> LENGTH: 19
<212> TYPE: DNA
<213> ORGANISM: Homo sapiens

<400> SEQUENCE: 79
tttgggcaaa cctcggtaa                                                19

<210> SEQ ID NO 80
<211> LENGTH: 17
<212> TYPE: DNA
<213> ORGANISM: Homo sapiens

<400> SEQUENCE: 80
gcacagcaaa tgccact                                                  17

<210> SEQ ID NO 81
<211> LENGTH: 23
<212> TYPE: DNA
<213> ORGANISM: Homo sapiens

<400> SEQUENCE: 81
cttgtctttc cctactgtct tac                                           23

<210> SEQ ID NO 82
<211> LENGTH: 18
<212> TYPE: DNA
<213> ORGANISM: Homo sapiens

<400> SEQUENCE: 82
cttgttccag cagaacct                                                 18

<210> SEQ ID NO 83
<211> LENGTH: 18
<212> TYPE: DNA
<213> ORGANISM: Homo sapiens

<400> SEQUENCE: 83
cagtcctctg caccgtta                                                 18

<210> SEQ ID NO 84
<211> LENGTH: 18
<212> TYPE: DNA
<213> ORGANISM: Homo sapiens

<400> SEQUENCE: 84
catccagatc cctcacat                                                 18
```

```
<210> SEQ ID NO 85
<211> LENGTH: 19
<212> TYPE: DNA
<213> ORGANISM: Homo sapiens

<400> SEQUENCE: 85
ccaagacaca gccagtaat                                              19

<210> SEQ ID NO 86
<211> LENGTH: 18
<212> TYPE: DNA
<213> ORGANISM: Homo sapiens

<400> SEQUENCE: 86
tttccagccc tcgtagtc                                               18

<210> SEQ ID NO 87
<211> LENGTH: 17
<212> TYPE: DNA
<213> ORGANISM: Homo sapiens

<400> SEQUENCE: 87
gggacacagg gaagaac                                                17

<210> SEQ ID NO 88
<211> LENGTH: 17
<212> TYPE: DNA
<213> ORGANISM: Homo sapiens

<400> SEQUENCE: 88
gtctgccact ctgcaac                                                17

<210> SEQ ID NO 89
<211> LENGTH: 17
<212> TYPE: DNA
<213> ORGANISM: Homo sapiens

<400> SEQUENCE: 89
gtcggctgac gctttga                                                17

<210> SEQ ID NO 90
<211> LENGTH: 23
<212> TYPE: DNA
<213> ORGANISM: Homo sapiens

<400> SEQUENCE: 90
gaacaagtca gtctagggaa tac                                         23

<210> SEQ ID NO 91
<211> LENGTH: 21
<212> TYPE: DNA
<213> ORGANISM: Homo sapiens

<400> SEQUENCE: 91
tgctttcgat aagtccagac a                                           21

<210> SEQ ID NO 92
<211> LENGTH: 18
<212> TYPE: DNA
<213> ORGANISM: Homo sapiens

<400> SEQUENCE: 92
cctctgaggc tggaaaca                                               18
```

<210> SEQ ID NO 93
<211> LENGTH: 19
<212> TYPE: DNA
<213> ORGANISM: Homo sapiens

<400> SEQUENCE: 93
atccactgat cttccttgc                                                  19

<210> SEQ ID NO 94
<211> LENGTH: 19
<212> TYPE: DNA
<213> ORGANISM: Homo sapiens

<400> SEQUENCE: 94
cagtgctgct tcagacaca                                                  19

<210> SEQ ID NO 95
<211> LENGTH: 21
<212> TYPE: DNA
<213> ORGANISM: Homo sapiens

<400> SEQUENCE: 95
cctttcttca agggtaaagg c                                               21

<210> SEQ ID NO 96
<211> LENGTH: 20
<212> TYPE: DNA
<213> ORGANISM: Homo sapiens

<400> SEQUENCE: 96
tcgaatttct ctcctcccat                                                 20

<210> SEQ ID NO 97
<211> LENGTH: 18
<212> TYPE: DNA
<213> ORGANISM: Homo sapiens

<400> SEQUENCE: 97
ctgagtccac acaggttt                                                   18

<210> SEQ ID NO 98
<211> LENGTH: 23
<212> TYPE: DNA
<213> ORGANISM: Homo sapiens

<400> SEQUENCE: 98
cccatacttg ttgatggcaa tta                                             23

<210> SEQ ID NO 99
<211> LENGTH: 18
<212> TYPE: DNA
<213> ORGANISM: Homo sapiens

<400> SEQUENCE: 99
tcctgcgtgt gttctact                                                   18

<210> SEQ ID NO 100
<211> LENGTH: 19
<212> TYPE: DNA
<213> ORGANISM: Homo sapiens

<400> SEQUENCE: 100
agtcatcatg tacccagca                                                  19

<210> SEQ ID NO 101
<211> LENGTH: 20
<212> TYPE: DNA
<213> ORGANISM: Homo sapiens

<400> SEQUENCE: 101
cccaggatac tctcttcctt                                               20

<210> SEQ ID NO 102
<211> LENGTH: 18
<212> TYPE: DNA
<213> ORGANISM: Homo sapiens

<400> SEQUENCE: 102
cactggatca actgcctc                                                 18

<210> SEQ ID NO 103
<211> LENGTH: 19
<212> TYPE: DNA
<213> ORGANISM: Homo sapiens

<400> SEQUENCE: 103
cagctgtcac acccagagc                                                19

<210> SEQ ID NO 104
<211> LENGTH: 17
<212> TYPE: DNA
<213> ORGANISM: Homo sapiens

<400> SEQUENCE: 104
cgtatggtgc agggtca                                                  17

<210> SEQ ID NO 105
<211> LENGTH: 20
<212> TYPE: DNA
<213> ORGANISM: Homo sapiens

<400> SEQUENCE: 105
tctggactgt ctggttgaat                                               20

<210> SEQ ID NO 106
<211> LENGTH: 19
<212> TYPE: DNA
<213> ORGANISM: Homo sapiens

<400> SEQUENCE: 106
cctgtacacc aagcttcat                                                19

<210> SEQ ID NO 107
<211> LENGTH: 19
<212> TYPE: DNA
<213> ORGANISM: Homo sapiens

<400> SEQUENCE: 107
ccatgcccac tttcttgta                                                19

<210> SEQ ID NO 108
<211> LENGTH: 20
<212> TYPE: DNA
<213> ORGANISM: Homo sapiens

<400> SEQUENCE: 108

```
<210> SEQ ID NO 109
<211> LENGTH: 18
<212> TYPE: DNA
<213> ORGANISM: Homo sapiens

<400> SEQUENCE: 109
cgtggactga gatgcatt                                                   18

<210> SEQ ID NO 110
<211> LENGTH: 21
<212> TYPE: DNA
<213> ORGANISM: Homo sapiens

<400> SEQUENCE: 110
ttcatgtcgt tgaacacctt g                                               21

<210> SEQ ID NO 111
<211> LENGTH: 21
<212> TYPE: DNA
<213> ORGANISM: Homo sapiens

<400> SEQUENCE: 111
cattttggct tttaggggta g                                               21

<210> SEQ ID NO 112
<211> LENGTH: 17
<212> TYPE: DNA
<213> ORGANISM: Homo sapiens

<400> SEQUENCE: 112
ggcagaagcg agacttt                                                    17

<210> SEQ ID NO 113
<211> LENGTH: 17
<212> TYPE: DNA
<213> ORGANISM: Homo sapiens

<400> SEQUENCE: 113
gcacatagga ggtggca                                                    17

<210> SEQ ID NO 114
<211> LENGTH: 17
<212> TYPE: DNA
<213> ORGANISM: Homo sapiens

<400> SEQUENCE: 114
gcggacttta ccgtgac                                                    17
```

METHODS FOR TYPING OF LUNG CANCER

CROSS-REFERENCE TO U.S. NON-PROVISIONAL APPLICATIONS

This application is a national phase of International Application No. PCT/US15/33611, which claims priority from U.S. Provisional Application Ser. No. 60/005,229 filed May 30, 2014, each of which is incorporated by reference herein in its entirety for all purposes.

STATEMENT REGARDING SEQUENCE LISTING

The contents of the text file submitted electronically herewith are incorporated herein by reference in their entirety: A computer readable format copy of the Sequence Listing (filename: GNCN_004_01US_SeqList_ST25.txt, date recorded: Nov. 29, 2016, file size 17 kilobytes).

BACKGROUND OF THE INVENTION

Lung cancer is the leading cause of cancer death in the United States and over 220,000 new lung cancer cases are identified each year. Lung cancer is a heterogeneous disease with subtypes generally determined by histology (small cell, non-small cell, carcinoid, adenocarcinoma, and squamous cell carcinoma). Differentiation among various morphologic subtypes of lung cancer is essential in guiding patient management and additional molecular testing is used to identify specific therapeutic target markers. Variability in morphology, limited tissue samples, and the need for assessment of a growing list of therapeutically targeted markers pose challenges to the current diagnostic standard. Studies of histologic diagnosis reproducibility have shown limited intra-pathologist agreement and inter-pathologist agreement.

While new therapies are increasingly directed toward specific subtypes of lung cancer (bevacizumab and pemetrexed), studies of histologic diagnosis reproducibility have shown limited intra-pathologist agreement and even less inter-pathologist agreement. Poorly differentiated tumors, conflicting immunohistochemistry results, and small volume biopsies in which only a limited number of stains can be performed continue to pose challenges to the current diagnostic standard (Travis and Rekhtman Sem Resp and Crit Care Med 2011; 32(1): 22-31; Travis et al. Arch Pathol Lab Med 2013; 137(5):668-84; Tang et al. J Thorac Dis 2014; 6(S5):S489-S501).

A recent example involving expert pathology re-review of lung cancer samples submitted to the TCGA Lung Cancer genome project led to the reclassification of 15-20% of lung tumors submitted, confirming the ongoing challenge of morphology-based diagnoses. (Cancer Genome Atlas Research Network. "Comprehensive genomic characterization of squamous cell lung cancers." Nature 489.7417 (2012): 519-525; Cancer Genome Atlas Research Network. Comprehensive molecular profiling of lung adenocarcinoma. Nature 511.7511 (2014): 543-550, each of which is incorporated by reference herein in its entirety). Thus a need exists for a more reliable means for determining lung cancer subtype. The present invention addresses this and other needs.

SUMMARY OF THE INVENTION

In one aspect, a method of assessing whether a patient's lung cancer subtype is adenocarcinoma, squamous carcinoma, or a neuroendocrine (encompassing both small cell carcinoma and carcinoid). In one embodiment, the method comprises probing the levels of at least five of the classifier biomarkers of Table 1A, Table 1B, Table 1C, Table 2, Table 3, Table 4, Table 5 or Table 6 at the nucleic acid level, in a lung cancer sample obtained from the patient. The probing step, in one embodiment, comprises mixing the sample with five or more oligonucleotides that are substantially complementary to portions of nucleic acid molecules of the at least five classifier biomarkers of Table 1A, Table 1B, Table 1C, Table 2, Table 3, Table 4, Table 5 or Table 6 under conditions suitable for hybridization of the five or more oligonucleotides to their complements or substantial complements; detecting whether hybridization occurs between the five or more oligonucleotides to their complements or substantial complements; and obtaining hybridization values of the at least five classifier biomarkers based on the detecting step. The hybridization values of the at least five classifier biomarkers are then compared to reference hybridization value(s) from at least one sample training set, wherein the at least one sample training set comprises, hybridization values from a reference adenocarcinoma, squamous cell carcinoma, or a neuroendocrine sample. The lung cancer sample is classified as an adenocarcinoma, squamous cell carcinoma, or a neuroendocrine sample based on the results of the comparing step.

In another aspect, a method of assessing whether a patient's lung cancer subtype is adenocarcinoma, squamous cell carcinoma, small cell carcinoma or carcinoid is provided. In one embodiment, the method comprises probing the levels of at least five classifier biomarkers of Table 1A, Table 1B, Table 1C, Table 2, Table 3, Table 4, Table 5 or Table 6 at the nucleic acid level, in a lung cancer sample obtained from the patient. The probing step, in one embodiment, comprises mixing the sample with five or more oligonucleotides that are substantially complementary to portions of nucleic molecules of the at least five classifier biomarkers of Table 1A, Table 1B, Table 1C, Table 2, Table 3, Table 4, Table 5 or Table 6 under conditions suitable for hybridization of the five or more oligonucleotides to their complements or substantial complements; detecting whether hybridization occurs between the five or more oligonucleotides to their complements or substantial complements; and obtaining hybridization values of the at least five classifier biomarkers based on the detecting step. The hybridization values of the at least five classifier biomarkers are then compared to reference hybridization value(s) from at least one sample training set, wherein the at least one sample training set comprises, hybridization values from a reference adenocarcinoma, squamous cell carcinoma, small cell carcinoma or carcinoid sample. The lung cancer sample is classified as an adenocarcinoma, squamous cell carcinoma, small cell carcinoma or carcinoid based on the results of the comparing step.

In yet another aspect, a method of assessing whether a patient's non-small cell lung carcinoma (NSCLC) subtype is adenocarcinoma or squamous cell carcinoma is provided. In one embodiment, the method comprises probing the levels of at least five of the classifier biomarkers of Table 1A, Table 1B, Table 1C, Table 2, Table 3, Table 4, Table 5 or Table 6 at the nucleic acid level, in a lung cancer sample obtained from the patient. The probing step, in one embodiment, comprises mixing the sample with five or more oligonucleotides that are substantially complementary to portions of cDNA molecules of the at least five classifier biomarkers of Table 1A, Table 1B, Table 1C, Table 2, Table 3, Table 4, Table 5 or Table 6 under conditions suitable for hybridization of the five or more oligonucleotides to their complements or substantial complements; detecting whether hybridization occurs between the five or more oligonucleotides to their complements or substantial complements; and obtaining hybridization values of the at least five classifier biomarkers based on the detecting step. The hybridization values of the at least five classifier biomarkers are then compared to reference hybridization value(s) from at least one sample training set, wherein the at least one sample training set comprises, hybridization values from a reference adenocarcinoma and/or squamous cell carcinoma sample. The NSCLC sample is classified as an adenocarcinoma or squamous cell carcinoma based on the results of the comparing step.

In one embodiment, the comparing step comprises determining a correlation between the hybridization values of the at least five classifier biomarkers and the reference hybridization values.

In one embodiment, the probing step comprises isolating the nucleic acid or portion thereof prior to the mixing step. In a further embodiment, the hybridization comprises hybridization of a cDNA to a cDNA, thereby forming a non-natural complex; or hybridization of a cDNA to an mRNA, thereby forming a non-natural complex. In even a further embodiment, the probing step comprises amplifying the nucleic acid in the sample.

In one embodiment, the at least five classifier biomarkers comprise from about 5 to about 50, from about 10 to about 50, from about 15 to about 50, from about 20 to about 50 or from about 25 to about 50 biomarkers. In another embodiment, the at least five classifier biomarkers comprise from about 5 to about 30, from about 10 to about 30, from about 15 to about 30, from about 20 to about 30 classifier biomarkers.

BRIEF DESCRIPTION OF THE DRAWINGS

FIG. 3 is a comparison of path review and LSP prediction for 77 FFPE samples. Each rectangle represents a single sample ordered by sample number. Arrows indicate 6 samples that disagreed with the original diagnosis by both pathology review and gene expression.

DETAILED DESCRIPTION OF THE INVENTION

Figure 1A:
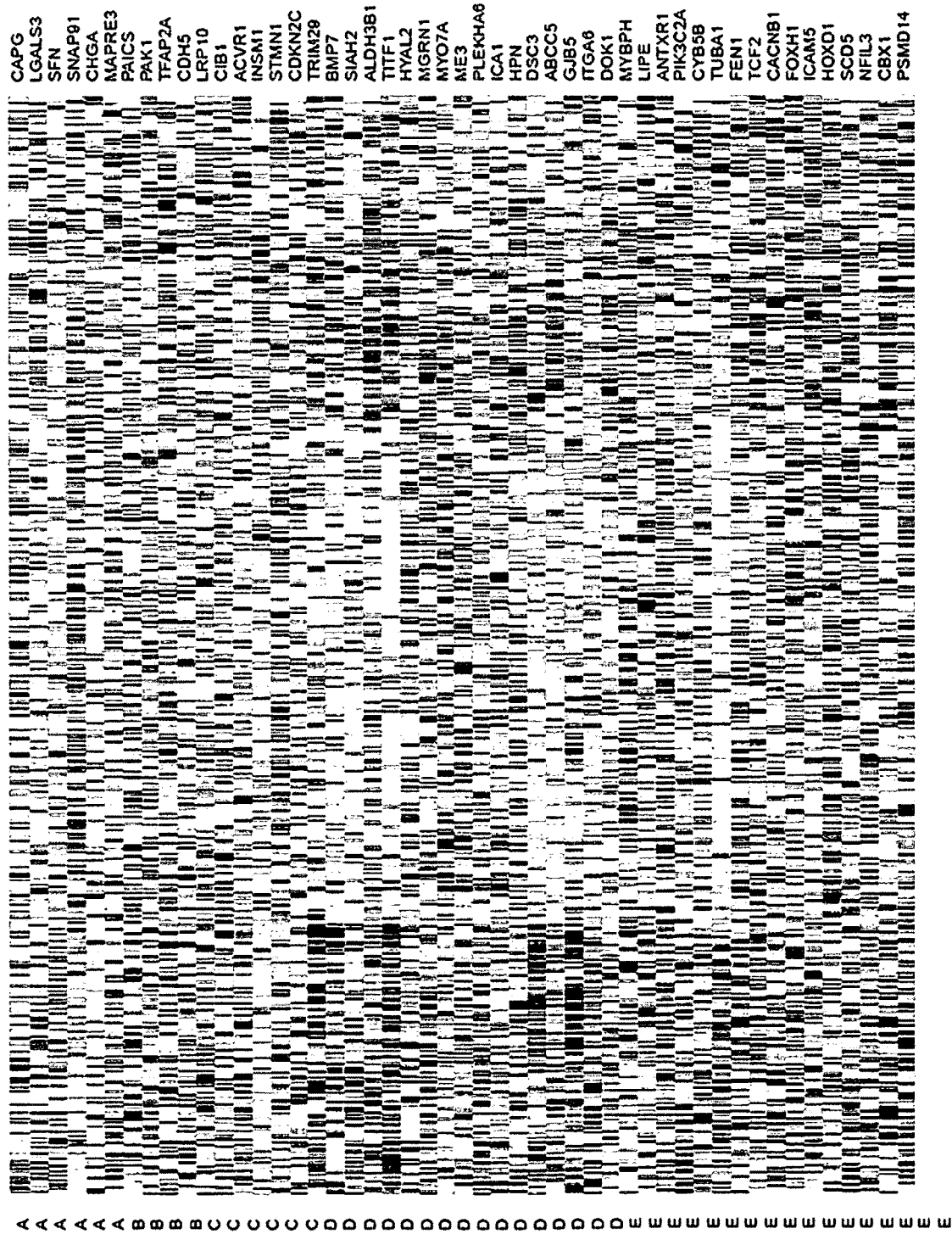
FIGS. 1A-1D illustrate exemplary gene expression heatmaps for adenocarcinoma (FIG. 1A), squamous cell carcinoma (FIG. 1B), small cell carcinoma (FIG. 1C), and carcinoid (FIG. 1D).
Figure 1B:
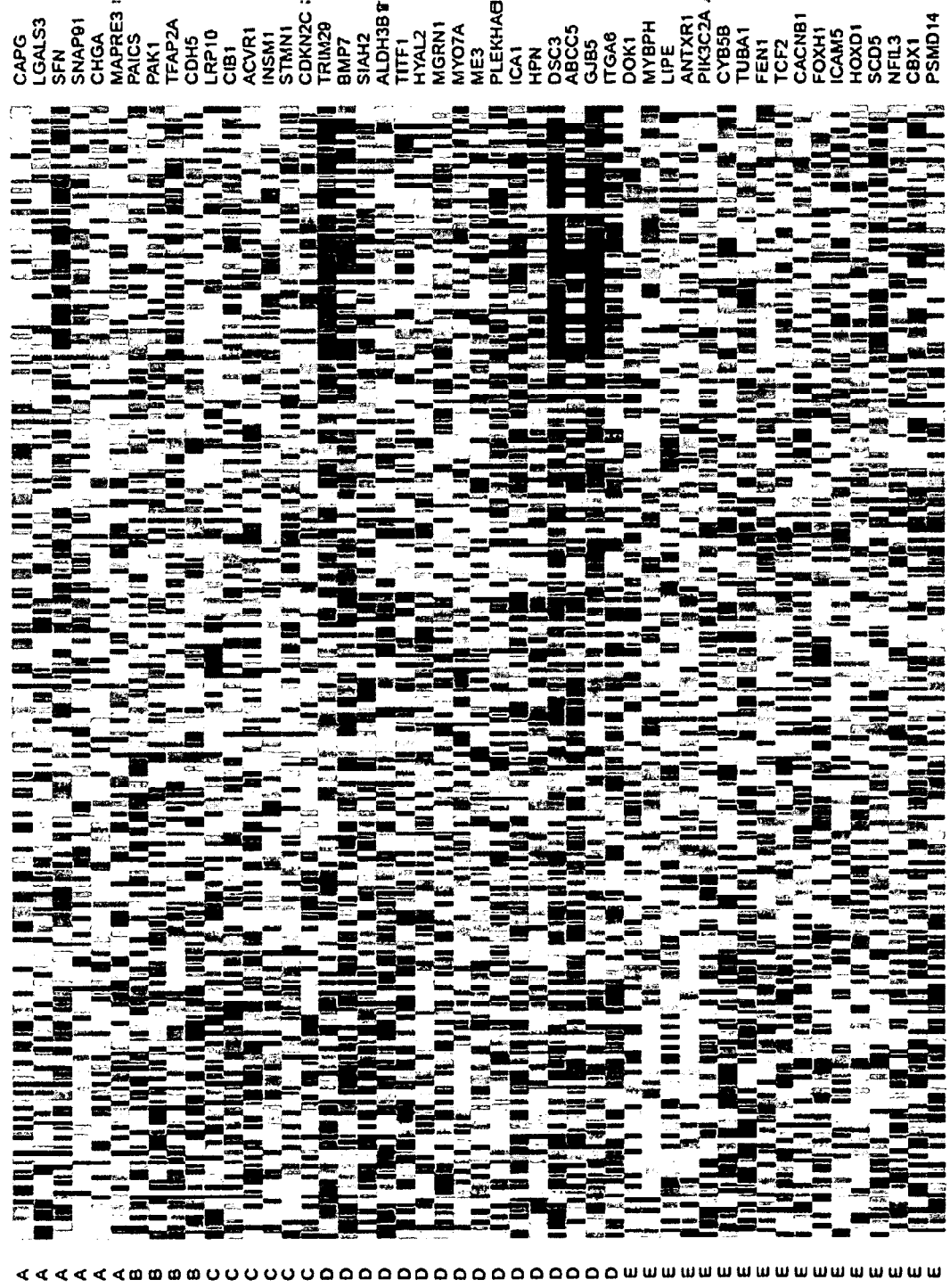
Figure 1C:
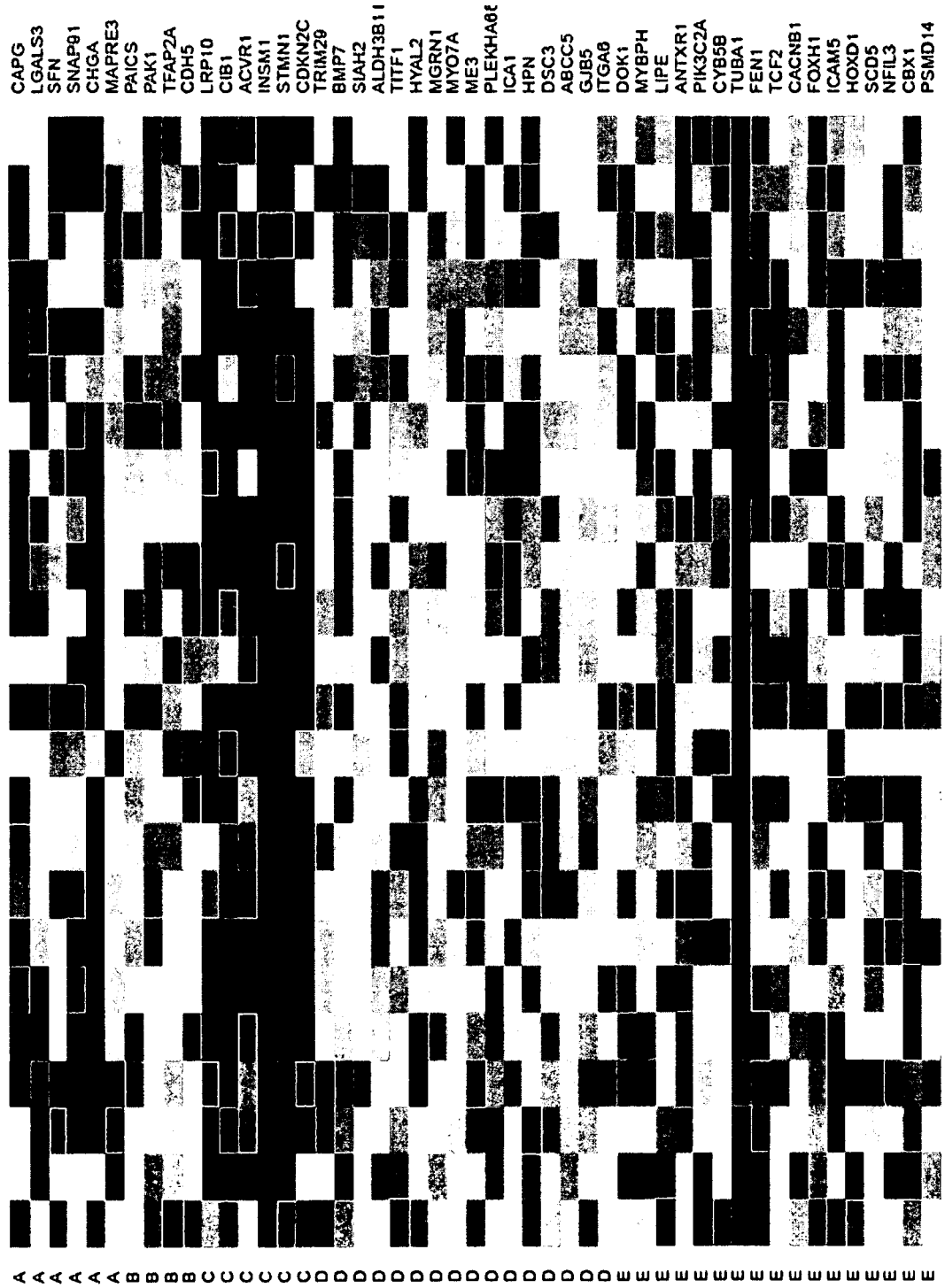
Figure 1D:
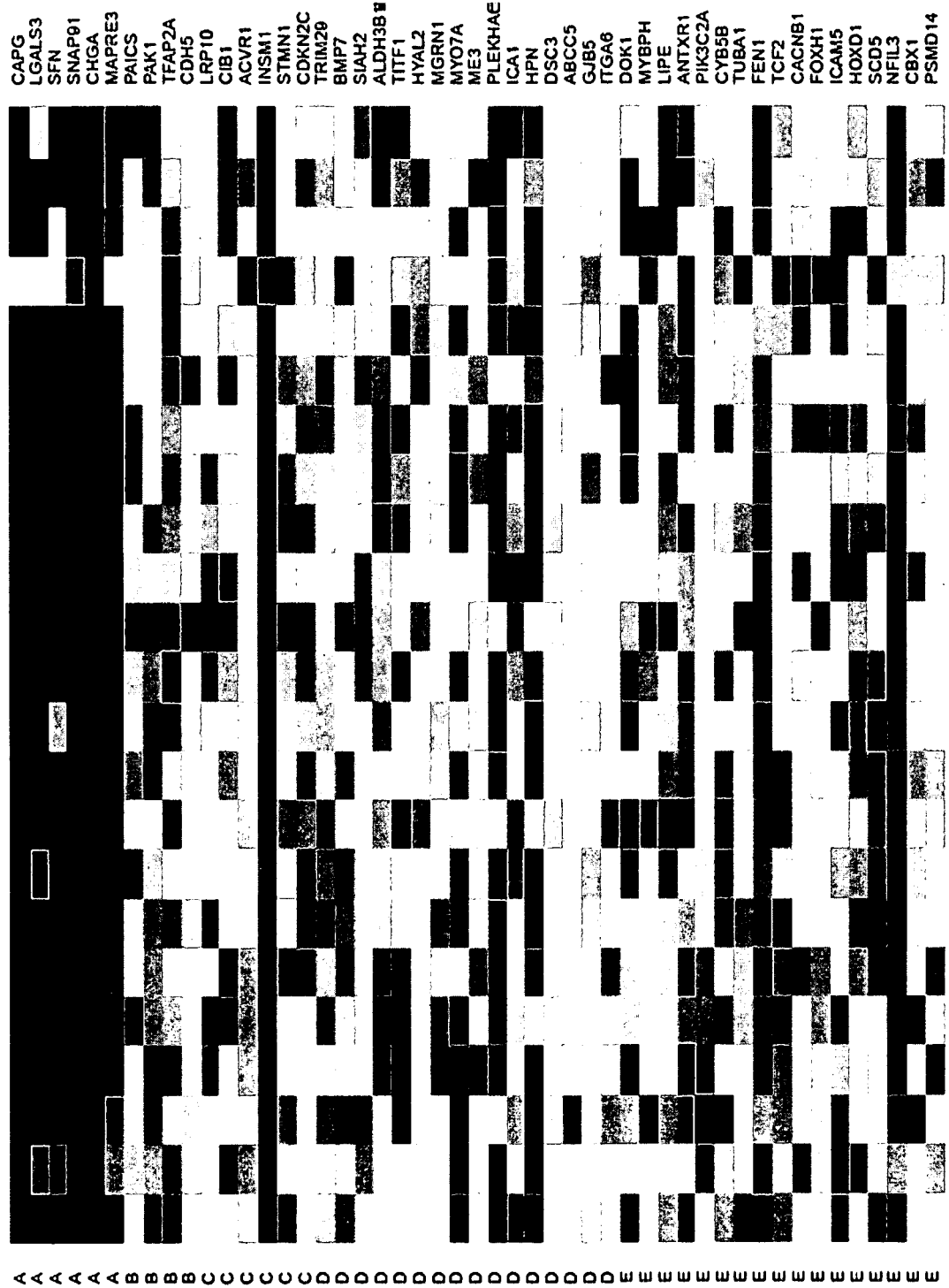

As used herein, an "expression profile" comprises one or more values corresponding to a measurement of the relative abundance, level, presence, or absence of expression of a discriminative gene. An expression profile can be derived from a subject prior to or subsequent to a diagnosis of lung cancer, can be derived from a biological sample collected from a subject at one or more time points prior to or following treatment or therapy, can be derived from a biological sample collected from a subject at one or more time points during which there is no treatment or therapy (e.g., to monitor progression of disease or to assess development of disease in a subject diagnosed with or at risk for lung cancer), or can be collected from a healthy subject.

The biomarker panels and methods provided herein are used in various aspects, to assess, (i) whether a patient's NSCLC subtype is adenocarcinoma or squamous cell carcinoma; (ii) whether a patient's lung cancer subtype is adenocarcinoma, squamous cell carcinoma, or a neuroendocrine (encompassing both small cell carcinoma and carcinoid) and/or (iii) whether a patient's lung cancer subtype is adenocarcinoma, squamous cell carcinoma, small cell carcinoma or carcinoid.

For example, the biomarker panels, or subsets thereof, as disclosed in Table 1A, Table 1B, Table 1C, Table 2, Table 3, Table 4, Table 5 and Table 6 are used in various embodiments to assess and classify a patient's lung cancer subtype. In one embodiment, the biomarker panel of Table 14 or Table 15, or a subset thereof is used to assess and classify a patient's lung cancer subtype.

In general, the methods provided herein are used to classify a lung cancer sample as a particular lung cancer subtype. In one embodiment, the method comprises probing the levels of at least five of the classifier biomarkers of Table 1A, Table 1B, Table 1C, Table 2, Table 3, Table 4, Table 5 or Table 6 at the nucleic acid level, in a lung cancer sample obtained from the patient. The probing step, in one embodiment, comprises mixing the sample with five or more oligonucleotides that are substantially complementary to portions of nucleic acid molecules, e.g., cDNA molecules or mRNA molecules, of the at least five classifier biomarkers of Table 1A, Table 1B, Table 1C, Table 2, Table 3, Table 4, Table 5 or Table 6 under conditions suitable for hybridization of the five or more oligonucleotides to their complements or substantial complements; detecting whether hybridization occurs between the five or more oligonucleotides to their complements or substantial complements; and obtaining hybridization values of the at least five classifier biomarkers based on the detecting step. The hybridization values of the at least five classifier biomarkers are then compared to reference hybridization value(s) from at least one sample training set. For example, the at least one sample training set comprises hybridization values from a reference adenocarcinoma, squamous cell carcinoma, a neuroendocrine sample, small cell carcinoma sample. The lung cancer sample is classified, for example, as an adenocarcinoma, squamous cell carcinoma, a neuroendocrine or small cell carcinoma based on the results of the comparing step.

The lung tissue sample can be any sample isolated from a human subject. For example, in one embodiment, the analysis is performed on lung biopsies that are embedded in paraffin wax. This aspect of the invention provides a means to improve current diagnostics by accurately identifying the major histological types, even from small biopsies. The methods of the invention, including the RT-PCR methods, are sensitive, precise and have multianalyte capability for use with paraffin embedded samples. See, for example, Cronin et al. (2004) Am. J Pathol. 164(1):35-42, herein incorporated by reference.

Formalin fixation and tissue embedding in paraffin wax is a universal approach for tissue processing prior to light microscopic evaluation. A major advantage afforded by formalin-fixed paraffin-embedded (FFPE) specimens is the preservation of cellular and architectural morphologic detail in tissue sections. (Fox et al. (1985) J Histochem Cytochem 33:845-853). The standard buffered formalin fixative in which biopsy specimens are processed is typically an aqueous solution containing 37% formaldehyde and 10-15% methyl alcohol. Formaldehyde is a highly reactive dipolar compound that results in the formation of protein-nucleic acid and protein-protein crosslinks in vitro (Clark et al.

(1986) J Histochem Cytochem 34:1509-1512; McGhee and von Hippel (1975) Biochemistry 14:1281-1296, each incorporated by reference herein).

In one embodiment, the sample used herein is obtained from an individual, and comprises fresh-frozen paraffin embedded (FFPE) tissue. However, other tissue and sample types are amenable for use herein.

Methods are known in the art for the isolation of RNA from FFPE tissue. In one embodiment, total RNA can be isolated from FFPE tissues as described by Bibikova et al. (2004) American Journal of Pathology 165:1799-1807, herein incorporated by reference. Likewise, the High Pure RNA Paraffin Kit (Roche) can be used. Paraffin is removed by xylene extraction followed by ethanol wash. RNA can be isolated from sectioned tissue blocks using the MasterPure Purification kit (Epicenter, Madison, Wis.); a DNase I treatment step is included. RNA can be extracted from frozen samples using Trizol reagent according to the supplier's instructions (Invitrogen Life Technologies, Carlsbad, Calif.). Samples with measurable residual genomic DNA can be resubjected to DNaseI treatment and assayed for DNA contamination. All purification, DNase treatment, and other steps can be performed according to the manufacturer's protocol. After total RNA isolation, samples can be stored at −80° C. until use.

General methods for mRNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker (Lab Invest. 56:A67, 1987) and De Andres et al. (Biotechniques 18:42-44, 1995). In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Other commercially available RNA isolation kits include MasterPure™. Complete DNA and RNA Purification Kit (Epicentre, Madison, Wis.) and Paraffin Block RNA Isolation Kit (Ambion, Austin, Tex.). Total RNA from tissue samples can be isolated, for example, using RNA Stat-60 (Tel-Test, Friendswood, Tex.). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155, incorporated by reference in its entirety for all purposes).

In one embodiment, a sample comprises cells harvested from a lung tissue sample, for example, an adenocarcinoma sample. Cells can be harvested from a biological sample using standard techniques known in the art. For example, in one embodiment, cells are harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract nucleic acid, e.g, messenger RNA. All samples obtained from a subject, including those subjected to any sort of further processing, are considered to be obtained from the subject.

The sample, in one embodiment, is further processed before the detection of the biomarker levels of the combination of biomarkers set forth herein. For example, mRNA in a cell or tissue sample can be separated from other components of the sample. The sample can be concentrated and/or purified to isolate mRNA in its non-natural state, as the mRNA is not in its natural environment. For example, studies have indicated that the higher order structure of mRNA in vivo differs from the in vitro structure of the same sequence (see, e.g., Rouskin et al. (2014). Nature 505, pp. 701-705, incorporated herein in its entirety for all purposes).

mRNA from the sample in one embodiment, is hybridized to a synthetic DNA probe, which in some embodiments, includes a detection moiety (e.g., detectable label, capture sequence, barcode reporting sequence). Accordingly, in these embodiments, a non-natural mRNA-cDNA complex is ultimately made and used for detection of the biomarker. In another embodiment, mRNA from the sample is directly labeled with a detectable label, e.g., a fluorophore. In a further embodiment, the non-natural labeled-mRNA molecule is hybridized to a cDNA probe and the complex is detected.

In one embodiment, once the mRNA is obtained from a sample, it is converted to complementary DNA (cDNA) in a hybridization reaction or is used in a hybridization reaction together with one or more cDNA probes. cDNA does not exist in vivo and therefore is a non-natural molecule. Furthermore, cDNA-mRNA hybrids are synthetic and do not exist in vivo. Besides cDNA not existing in vivo, cDNA is necessarily different than mRNA, as it includes deoxyribonucleic acid and not ribonucleic acid. The cDNA is then amplified, for example, by the polymerase chain reaction (PCR) or other amplification method known to those of ordinary skill in the art. For example, other amplification methods that may be employed include the ligase chain reaction (LCR) (Wu and Wallace, Genomics, 4:560 (1989), Landegren et al., Science, 241:1077 (1988), incorporated by reference in its entirety for all purposes, transcription amplification (Kwoh et al., *Proc. Natl. Acad. Sci. USA*, 86:1173 (1989), incorporated by reference in its entirety for all purposes), self-sustained sequence replication (Guatelli et al., *Proc. Nat. Acad. Sci. USA*, 87:1874 (1990), incorporated by reference in its entirety for all purposes), incorporated by reference in its entirety for all purposes, and nucleic acid based sequence amplification (NASBA). Guidelines for selecting primers for PCR amplification are known to those of ordinary skill in the art. See, e.g., McPherson et al., PCR Basics: From Background to Bench, Springer-Verlag, 2000, incorporated by reference in its entirety for all purposes. The product of this amplification reaction, i.e., amplified cDNA is also necessarily a non-natural product. First, as mentioned above, cDNA is a non-natural molecule. Second, in the case of PCR, the amplification process serves to create hundreds of millions of cDNA copies for every individual cDNA molecule of starting material. The number of copies generated are far removed from the number of copies of mRNA that are present in vivo.

In one embodiment, cDNA is amplified with primers that introduce an additional DNA sequence (e.g., adapter, reporter, capture sequence or moiety, barcode) onto the fragments (e.g., with the use of adapter-specific primers), or mRNA or cDNA biomarker sequences are hybridized directly to a cDNA probe comprising the additional sequence (e.g., adapter, reporter, capture sequence or moiety, barcode). Amplification and/or hybridization of mRNA to a cDNA probe therefore serves to create non-natural double stranded molecules from the non-natural single stranded cDNA, or the mRNA, by introducing additional sequences and forming non-natural hybrids. Further, as known to those of ordinary skill in the art, amplification procedures have error rates associated with them. Therefore, amplification introduces further modifications into the cDNA molecules. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature and (iv) the chemical addition of a detectable label to the cDNA molecules.

In some embodiments, the expression of a biomarker of interest is detected at the nucleic acid level via detection of non-natural cDNA molecules.

In some embodiments, the method for lung cancer subtyping includes detecting expression levels of a classifier biomarker set. In some embodiments, the detecting includes all of the classifier biomarkers of Table 1A, 1B or 1C, Table 2, Table 3, Table 4, Table 5 or Table 6 at the nucleic acid level. In another embodiment, a subset of the classifier biomarkers of Table 1A, 1B or 1C are probed for, for example, from about 5 to about 20. In one embodiment, a subset of biomarkers probed for comprises from about 5 to about 50, from about 5 to about 40, from about 5 to about 30, or from about 5 to about 25 of the classifier biomarkers of Table 1A, 1B or 1C, Table 2, Table 3, Table 4, Table 5 or Table 6. In another embodiment, a subset of biomarkers probed for comprises from about 10 to about 50, from about 10 to about 40, from about 10 to about 30, or from about 10 to about 25 of the classifier biomarkers of Table 1A, 1B or 1C, Table 2, Table 3, Table 4, Table 5 or Table 6. In yet another embodiment, a subset of biomarkers probed for comprises 5, 10, 15, 20, 25, 30, 35, 40, 45 or 50 of the classifier biomarkers of Table 1A, 1B or 1C, Table 2, Table 3, Table 4, Table 5 or Table 6. In even another embodiment, a subset of biomarkers probed for comprises at least about 5, at least about 10, at least about 15, at least about 20, at least about 25, at least about 30, at least about 35, at least about 40, at least about 45 or at least about 50 of the classifier biomarkers of Table 1A, 1B or 1C, Table 2, Table 3, Table 4, Table 5 or Table 6. It should be understood that the number of biomarkers probed for will dictate the number of oligonucleotides initially used in a method provided herein. For example, where 5 or 10 of the biomarkers of Table 1A, 1B or 1C, Table 2, Table 3, Table 4, Table 5 or Table 6 are probed for, 5 oligonucleotides or 10 oligonucleotides, respectively, will be mixed with the sample under conditions suitable for hybridization of the oligonucleotides to the biomarkers, or fragments thereof.

In one embodiment, from about five to about 10, from about 5 to about 15, from about 5 to about 20, from about 5 to about 25, from about 5 to about 30, from about 5 to about 35, from about 5 to about 40, from about 5 to about 45, from about 5 to about 50 of the biomarkers in any of Table 1A, Table 1B, Table 1C, Table 2, Table 3, Table 4, Table 5 and Table 6 are probed for in a method to determine the lung cancer subtype. In another embodiment, each of the biomarkers from any one of Table 1A, Table 1B, Table 1C, Table 2, Table 3, Table 4, Table 5, or from Table 6 are probed for in a method to determine the lung cancer subtype of a patient's lung cancer sample.

The detecting can be performed by any suitable technique including, but not limited to, RNA-seq, a reverse transcriptase polymerase chain reaction (RT-PCR), a microarray hybridization assay, or another hybridization assay, e.g., a NanoString assay for example, with primers and/or probes specific to the classifier biomarkers, and/or the like. It should be noted that the primers provided in Table 1A, Table 1B, Table 1C, Table 2, Table 3, Table 4, Table 5 and Table 6 are merely for illustrative purposes and should not be construed as limiting the invention.

The biomarkers described herein include RNA comprising the entire or partial sequence of any of the nucleic acid sequences of interest, or their non-natural cDNA product, obtained synthetically in vitro in a reverse transcription reaction. The term "fragment" is intended to refer to a portion of the polynucleotide that generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein of the invention.

In some embodiments, overexpression, such as of an RNA transcript or its expression product, is determined by normalization to the level of reference RNA transcripts or their expression products, which can be all measured transcripts (or their products) in the sample or a particular reference set of RNA transcripts (or their non-natural cDNA products). Normalization is performed to correct for or normalize away both differences in the amount of RNA or cDNA assayed and variability in the quality of the RNA or cDNA used. Therefore, an assay typically measures and incorporates the expression of certain normalizing genes, including well known housekeeping genes, such as, for example, GAPDH and/or β-Actin. Alternatively, normalization can be based on the mean or median signal of all of the assayed biomarkers or a large subset thereof (global normalization approach).

TABLE 1A

| Gene Symbol | Gene name | Forward primer | SEQ ID | Reverse primer | SEQ ID |
|---|---|---|---|---|---|
| CDH5 | cadherin 5, type 2, VE-cadherin (vascular epithelium) | AAGAGAGATTG GATTTGGAACC | 1 | TTCTTGCGACTCACGCT | 58 |
| CLEC3B | C-type lectin domain family 3, member B | CCAGAAGCCCA AGAAGATTGTA | 2 | GCTCCTCAAACAT CTTTGTGTTCA | 59 |
| PAICS | phosphoribosylami noimidazole carboxylase, phosphoribosylami noimidazole | AATCCTGGTGT CAAGGAAG | 3 | GACCACTGTGGG TCATTATT | 60 |

TABLE 1A-continued

| Gene Symbol | Gene name | Forward primer | SEQ ID | Reverse primer | SEQ ID |
|---|---|---|---|---|---|
| | succinocarboxamide synthetase | | | | |
| PAK1 | p21/Cdc42/Rac1-activated kinase 1 (STE20 homolog, yeast) | GGACCGATTTT ACCGATCC | 4 | GAAATCTCTGGC CGCTC | 61 |
| PECAM1 | platelet/endothelial cell adhesion molecule (CD31 antigen) | ACAGTCCAGAT AGTCGTATGT | 5 | ACTGGGCATCAT AAGAAATCC | 62 |
| TFAP2A | transcription factor AP-2 alpha (activating enhancer binding protein 2 alpha) | GTCTCCGCCATC CCTAT | 6 | ACTGAACAGAAG ACTTCGT | 63 |
| ACVR1 | activin A receptor, type 1 | ACTGGTGTAAC AGGAACAT | 7 | AACCTCCAAGTG GAAATTCT | 64 |
| CDKN2C | cyclin-dependent kinase inhibitor 2C (p18, inhibits CDK4) | TTTGGAAGGAC TGCGCT | 8 | TCGGTCTTTCAAA TCGGGATTA | 65 |
| CIB1 | calcium and integrin binding 1 (calmyrin) | CACGTCATCTCC CGTTC | 9 | CTGCTGTCACAG GACAAT | 66 |
| INSM1 | insulinoma-associated 1 | ATTGAACTTCCC ACACGA | 10 | AAGGTAAAGCCA GACTCCA | 67 |
| LRP10 | low density lipo-protein receptor-related protein 10 | GGAACAGACTG TCACCAT | 11 | GGGAGCGTAGGG TTAAG | 68 |
| STMN1 | stathmin 1/oncoprotein 18 | TCAGAGTGTGTG GTCAGGC | 12 | CAGTGTATTCTGC ACAATCAAC | 69 |
| CAPG | capping protein (actin filament), gelsolin-like | GGGACAGCTTC AACACT | 13 | GTTCCAGGATGTT GGACTTTC | 70 |
| CHGA | chromogranin A (parathyroid secretory protein 1) | CCTGTGAACAG CCCTATG | 14 | GGAAAGTGTGTC GGAGAT | 71 |
| LGALS3 | lectin, galactoside-binding, soluble, 3 (galectin 3) | TTCTGGGCACG GTGAAG | 15 | AGGCAACATCAT TCCCTC | 72 |
| MAPRE3 | microtubule-associated protein, RP/EB family, member 3 | GGCCAAACTAG AGCACGAATA | 16 | GTCAACACCCAT CTTCTTAAA | 73 |
| SFN | stratifin | TCAGCAAGAAG GAGATGCC | 17 | CGTAGTGGAAGA CGGAAA | 74 |
| SNAP91 | synaptosomal-associated protein, 91 kDa homolog (mouse) | GTGCTCCCTCTC CATTAAGTA | 18 | CTGGTGTAGAATT AGGAGACGTA | 75 |
| ABCC5 | ATP-binding cassette, sub-family C (CFTR/MRP), member 5 | CAAGTTCAGGA GAACTCGAC | 19 | GGCATCAAGAGA GAGGC | 76 |
| ALDH3B1 | aldehyde dehydro-genase 3 family, member B1 | GGCTGTGGTTA TGCGATAG | 20 | GATAAAGAGTTA CAAGCTCCTCTG | 77 |
| ANTXR1 | Anthrax toxin receptor 1 | ACCCGAGGAAC AACCTTA | 21 | TCTAGGCCTTGAC GGAT | 78 |
| BMP7 | Bone morphogenetic protein 7 | CCCTCTCCATTC CCTACA | 22 | TTTGGGCAAACCTCGGTA A | 79 |

TABLE 1A-continued

| Gene Symbol | Gene name | Forward primer | SEQ ID | Reverse primer | SEQ ID |
|---|---|---|---|---|---|
| | (osteogenic protein 1) | | | | |
| CACNB1 | calcium channel, voltage-dependent, beta 1 subunit | CAGAGCGCCAG GCATTA | 23 | GCACAGCAAATG CCACT | 80 |
| CBX1 | chromobox homolog 1 (HP1 beta homolog *Drosophila*) | CCACTGGCTGA GGTGTTA | 24 | CTTGTCTTTCCCT ACTGTCTTAC | 81 |
| CYB5B | cytochrome b5 tye B (outer mitochondrial membrane) | TGGGCGAGTCT ACGATG | 25 | CTTGTTCCAGCAG AACCT | 82 |
| DOK1 | docking, protein 1, 62 kDa (downstream of tyrosine kinase 1) | CTTTCTGCCCTG GAGATG | 26 | CAGTCCTCTGCAC CGTTA | 83 |
| DSC3 | desmocollin 3 | GCGCCATTTGCT AGAGATA | 27 | CATCCAGATCCCT CACAT | 84 |
| FEN1 | flap structure-specific endonuclease 1 | AGAGAAGATGG GCAGAAAG | 28 | CCAAGACACAGC CAGTAAT | 85 |
| FOXH1 | forkhead box H1 | GCCCAGATCAT CCGTCA | 29 | TTTCCAGCCCTCG TAGTC | 86 |
| GJB5 | gap junction protein, beta 5 (connexin 31.1) | ACCACAAGGAC TTCGAC | 30 | GGGACACAGGGA AGAAC | 87 |
| HOXD1 | homeobox D1 | GCTCCGCTGCT ATCTTT | 31 | GTCTGCCACTCTG CAAC | 88 |
| HPN | Hepsin (transmembrane protease, serine 1) | AGCGGCCAGGT GGATTA | 32 | GTCGGCTGACGC TTTGA | 89 |
| HYAL2 | hyaluronoglucosam | ATGGGCTTTGG GAGCATA | 33 | GAACAAGTCAGT CTAGGGAATAC | 90 |
| ICA1 | islet cell autoantigen 1, 69 kDa | GACCTGGATGC CAAGCTA | 34 | TGCTTTCGATAAG TCCAGACA | 91 |
| ICAM5 | intercellular adhesion molecule 5, telencephalin | CCGGCTCTTGG AAGTTG | 35 | CCTCTGAGGCTG GAAACA | 92 |
| ITGA6 | integrin, alpha 6 | ACGCGGATCGA GTTTGATAA | 36 | ATCCACTGATCTT CCTTGC | 93 |
| LIPE | lipase, hormone-sensitive | CGCAAGTCCCA GAAGAT | 37 | CAGTGCTGCTTCA GACACA | 94 |
| MF3 | malic enzyme 3, NADP(+)-dependent, Mitochondrial | CGCGGATACGA TGTCAC | 38 | CCTTTCTTCAAGG GTAAAGGC | 95 |
| MGRN1 | mahogunin, ring finger 1 | GAACTCGGCCT ATCGCT | 39 | TCGAATTTCTCTC CTCCCAT | 96 |
| MYBPH | mysoin binding protein H | TCTGACCTCATC ATCGGCAA | 40 | CTGAGTCCACAC AGGTTT | 97 |
| MYO7A | mysosin VIIA | GAGGTGAAGCA AACTACGGA | 41 | CCCATACTTGTTG ATGGCAATTA | 98 |
| NFIL3 | nuclear factor, interlukin 3 regulated | ACTCTCCACAA AGCTCG | 42 | TCCTGCGTGTGTT CTACT | 99 |
| PIK3C2A | phosphoinositide-3-kinase, class 2, alpha polypeptide | GGATTTCAGCT ACCAGTTACTT | 43 | AGTCATCATGTAC CAGCA | 100 |

TABLE 1A-continued

| Gene Symbol | Gene name | Forward primer | SEQ ID | Reverse primer | SEQ ID |
|---|---|---|---|---|---|
| PLEKHA6 | pleckstrin homology domain containing, family A member 6 | TTCGTCCTGGTGGATCG | 44 | CCCAGGATACTCTCTTCCTT | 101 |
| PSMD14 | proteasome (prosome, macropain) 26S subunit, non-ATPase, 14 | AGTGATTGATGTGTTTGCTATG | 45 | CACTGGATCAACTGCCTC | 102 |
| SCD5 | stearoyl-CoA desaturase 5 | CAAAGCCAAGCCACTCACTC | 46 | CAGCTGTCACACCCAGAGC | 103 |
| SIAH2 | seven in absentia homolog 2 (Drosophila) | CTCGGCAGTCCTGTTTC | 47 | CGTATGGTGCAGGGTCA | 104 |
| TCF2 | transcription factor 2, hepatic; LF-B3; variant hepatic nuclear factor | ACACCTGGTACGTCAGAA | 48 | TCTGGACTGTCTGGTTGAAT | 105 |
| TCP1 | t-complex 1 | ATGCCCAAGAGAATCGTAAA | 49 | CCTGTACACCAAGCTTCAT | 106 |
| TTF1 | thyroid transcription factor 1 | ATGAGTCCAAAGCACACGA | 50 | CCATGCCCACTTTCTTGTA | 107 |
| TRIM29 | triparite morif-contain 29 | TGAGATTGAGGATGAAGCTGAG | 51 | CATTGGTGGTGAAGCTCTTG | 108 |
| TUBA1 | tubulin, aplha 1 | CCGACTCAACGTGAGAC | 52 | CCTGGACTGAGATGCATT | 109 |
| CFL1 | cofilin 1 (non-muscle) | GTGCCCTCTCCTTTTCG | 53 | TTCATGTCGTTGAACACTTG | 110 |
| EEF1A1 | eukaryotic translation elongation factor 1 alpha 1 | CGTTCTTTTTCGCAACGG | 54 | CATTTTGGCTTTAGGGGTAG | 111 |
| RPL10 | ribosomal protein L10 | GGTGTGCCACTGAAGAT | 55 | GGCAGAAGCGAGACTTT | 112 |
| RPL28 | ribosomal protein L28 | GTGTCGTGGTGGTCATT | 56 | GCACATAGGAGGTGGCA | 113 |
| RPL37A | ribosomal protein L37a | GCATGAAGACAGTGGCT | 57 | GCGGACTTTACCGTGAC | 114 |

TABLE 1B

| Gene Symbol | Gene name | Forward primer | SEQ ID | Reverse primer | SEQ ID |
|---|---|---|---|---|---|
| CDH5 | cadherin 5, type 2, VE-cadherin (vascular epithelium) | AAGAGAGATTGGATTTGGAACC | 1 | TTCTTGCGACTCACGCT | 58 |
| CLEC3B | C-type lectin domain family 3, member B | CCAGAAGCCCAAGAAGATTGTA | 2 | GCTCCTCAAACATCTTTGTGTTCA | 59 |
| PAICS | phosphoribosylaminoimidazole carboxylase, phosphoribosylaminoimidazole succinocarboxamide synthetase | AATCCTGGTGTCAAGGAAG | 3 | GACCACTGTGGGTCATTATT | 60 |
| PAK1 | p21/Cdc42/Rac1-activated kinase 1 (STE20 homolog, yeast) | GGACCGATTTTACCGATCC | 4 | GAAATCTCTGGCCGCTC | 61 |

TABLE 1B -continued

| Gene Symbol | Gene name | Forward primer | SEQ ID | Reverse primer | SEQ ID |
|---|---|---|---|---|---|
| PECAM1 | platelet/endothelial cell adhesion molecule (CD31 antigen) | ACAGTCCAGAT AGTCGTATGT | 5 | ACTGGGCATCAT AAGAAATCC | 62 |
| TFAP2A | transcription factor AP-2 alpha (activating enhancer binding protein 2 alpha) | GTCTCCGCCATC CCTAT | 6 | ACTGAACAGAAG ACTTCGT | 63 |
| ACVR1 | activin A receptor, type 1 | ACTGGTGTAAC AGGAACAT | 7 | AACCTCCAAGTG GAAATTCT | 64 |
| CDKN2C | cyclin-dependent kinase inhibitor 2C (p18, inhibits CDK4) | TTTGGAAGGAC TGCGCT | 8 | TCGGTCTTTCAAA TCGGGATTA | 65 |
| CIB1 | calcium and integrin binding 1 (calmyrin) | CACGTCATCTCC CGTTC | 9 | CTGCTGTCACAG GACAAT | 66 |
| INSM1 | insulinoma- associated 1 | ATTGAACTTCCC ACACGA | 10 | AAGGTAAAGCCA GACTCCA | 67 |
| LRP10 | low density lipo- protein receptor- related protein 10 | GGAACAGACTG TCACCAT | 11 | GGGAGCGTAGGG TTAAG | 68 |
| STMN1 | stathmin 1/oncoprotein 18 | TCAGAGTGTGTG GTCAGGC | 12 | CAGTGTATTCTGC ACAATCAAC | 69 |
| CAPG | capping protein (actin filament), gelsolin-like | GGGACAGCTTC AACACT | 13 | GTTCCAGGATGTT GGACTTTC | 70 |
| CHGA | chromogranin A (parathyroid secretory protein 1) | CCTGTGAACAG CCCTATG | 14 | GGAAAGTGTGTC GGAGAT | 71 |
| LGALS3 | lectin, galactoside- binding, soluble, 3 (galectin 3) | TTCTGGGCACG GTGAAG | 15 | AGGCAACATCAT TCCCTC | 72 |
| MAPRE3 | microtubule- associated protein, RP/EB family, member 3 | GGCCAAACTAG AGCACGAATA | 16 | GTCAACACCCAT CTTCTTAAA | 73 |
| SFN | stratifin | TCAGCAAGAAG GAGATGCC | 17 | CGTAGTGGAAGA CGGAAA | 74 |
| SNAP91 | synaptosomal- associated protein, 91 kDa homolog (mouse) | GTGCTCCCTCTC CATTAAGTA | 18 | CTGGTGTAGAATT AGGAGACGTA | 75 |
| ABCC5 | ATP-binding cassette, sub-family C (CFTR/MRP), member 5 | CAAGTTCAGGA GAACTCGAC | 19 | GGCATCAAGAGA GAGGC | 76 |
| ALDH3B1 | aldehyde dehydro- genase 3 family, member B1 | GGCTGTGGTTA TGCGATAG | 20 | GATAAAGAGTTA CAAGCTCCTCTG | 77 |
| ANTXR1 | Anthrax toxin receptor 1 | ACCCGAGGAAC AACCTTA | 21 | TCTAGGCCTTGAC GGAT | 78 |
| CACNB1 | calcium channel, voltage-dependent, beta 1 subunit | CAGAGCGCCAG GCATTA | 23 | GCACAGCAAATG CCACT | 80 |
| CBX1 | chromobox homolog 1 (HP1 beta homolog *Drosophila*) | CCACTGGCTGA GGTGTTA | 24 | CTTGTCTTTCCCT ACTGTCTTAC | 81 |

TABLE 1B-continued

| Gene Symbol | Gene name | Forward primer | SEQ ID | Reverse primer | SEQ ID |
|---|---|---|---|---|---|
| CYB5B | cytochrome b5 tye B (outer mitochondrial membrane) | TGGGCGAGTCT ACGATG | 25 | CTTGTTCCAGCAG AACCT | 82 |
| DOK1 | docking, protein 1, 62 kDa (downstream of tyrosine kinase 1) | CTTTCTGCCCTG GAGATG | 26 | CAGTCCTCTGCAC CGTTA | 83 |
| DSC3 | desmocollin 3 | GCGCCATTTGCT AGAGATA | 27 | CATCCAGATCCCT CACAT | 84 |
| FEN1 | flap structure-specific endonuclease 1 | AGAGAAGATGG GCAGAAAG | 28 | CCAAGACACAGC CAGTAAT | 85 |
| FOXH1 | forkhead box H1 | GCCCAGATCAT CCGTCA | 29 | TTTCCAGCCCTCG TAGTC | 86 |
| GJB5 | gap junction protein, beta 5 (connexin 31.1) | ACCACAAGGAC TTCGAC | 30 | GGGACACAGGGA AGAAC | 87 |
| HOXD1 | homeobox D1 | GCTCCGCTGCT ATCTTT | 31 | GTCTGCCACTCTG CAAC | 88 |
| HPN | Hepsin (transmembrane protease, serine 1) | AGCGGCCAGGT GGATTA | 32 | GTCGGCTGACGC TTTGA | 89 |
| HYAL2 | hyaluronoglucosam | ATGGGCTTTGG GAGCATA | 33 | GAACAAGTCAGT CTAGGGAATAC | 90 |
| ICA1 | islet cell autoantigen 1, 69 kDa | GACCTGGATGC CAAGCTA | 34 | TGCTTTCGATAAG TCCAGACA | 91 |
| ICAM5 | intercellular adhesion molecule 5, telencephalin | CCGGCTCTTGG AAGTTG | 35 | CCTCTGAGGCTG GAAACA | 92 |
| ITGA6 | integrin, alpha 6 | ACGCGGATCGA GTTTGATAA | 36 | ATCCACTGATCTT CCTTGC | 93 |
| LIPE | lipase, | CGCAAGTCCCA GAAGAT | 37 | CAGTGCTGCTTCA | 94 |
| MF3 | malic enzyme 3, NADP(+)-dependent, Mitochondrial | CGCGGATACGA TGTCAC | 38 | CCTTTCTTCAAGG GTAAAGGC | 95 |
| MGRN1 | mahogunin, ring finger 1 | GAACTCGGCCT ATCGCT | 39 | TCGAATTTCTCTC CTCCCAT | 96 |
| MYBPH | mysoin binding protein H | TCTGACCTCATC ATCGGCAA | 40 | CTGAGTCCACAC AGGTTT | 97 |
| MYO7A | mysosin VIIA | GAGGTGAAGCA AACTACGGA | 41 | CCCATACTTGTTG ATGGCAATTA | 98 |
| NFIL3 | nuclear factor, interlukin 3 regulated | ACTCTCCACAA AGCTCG | 42 | TCCTGCGTGTGTT CTACT | 99 |
| PIK3C2A | phosphoinositide-3-kinase, class 2, alpha polypeptide | GGATTTCAGCT ACCAGTTACTT | 43 | AGTCATCATGTAC CCAGCA | 100 |
| PLEKHA6 | pleckstrin homology domain containing, family A member 6 | TTCGTCCTGGTG GATCG | 44 | CCCAGGATACTCT CTTCCTT | 101 |
| PSMD14 | proteasome (prosome, macropain) 26S subunit, non-ATPase, 14 | AGTGATTGATG TGTTTGCTATG | 45 | CACTGGATCAAC TGCCTC | 102 |

TABLE 1B -continued

| Gene Symbol | Gene name | Forward primer | SEQ ID | Reverse primer | SEQ ID |
|---|---|---|---|---|---|
| SCD5 | stearoyl-CoA desaturase 5 | CAAAGCCAAGC CACTCACTC | 46 | CAGCTGTCACAC CCAGAGC | 103 |
| SIAH2 | seven in absentia homolog 2 (Drosophila) | CTCGGCAGTCC TGTTTC | 47 | CGTATGGTGCAG GGTCA | 104 |
| TCF2 | transcription factor 2, hepatic; LF-B3; variant hepatic nuclear factor | ACACCTGGTAC GTCAGAA | 48 | TCTGGACTGTCTG GTTGAAT | 105 |
| TCP1 | t-complex 1 | ATGCCCAAGAG AATCGTAAA | 49 | CCTGTACACCAA GCTTCAT | 106 |
| TTF1 | thyroid transcription factor 1 | ATGAGTCCAAA GCACACGA | 50 | CCATGCCCACTTT CTTGTA | 107 |
| TRIM29 | triparite morif-contain 29 | TGAGATTGAGG ATGAAGCTGAG | 51 | CATTGGTGGTGA AGCTCTTG | 108 |
| TUBA1 | tubulin, aplha 1 | CCGACTCAACG TGAGAC | 52 | CCTGGACTGAGA TGCATT | 109 |
| CFL1 | cofilin 1 (non-muscle) | GTGCCCTCTCCT TTTCG | 53 | TTCATGTCGTTGA ACACTTG | 110 |
| EEF1A1 | eukaryotic translation elongation factor 1 alpha 1 | CGTTCTTTTTCG CAACGG | 54 | CATTTTGGCTTTT AGGGGTAG | 111 |
| RPL10 | ribosomal protein L10 | GGTGTGCCACT GAAGAT | 55 | GGCAGAAGCGAG ACTTT | 112 |
| RPL28 | ribosomal protein L28 | GTGTCGTGGTG GTCATT | 56 | GCACATAGGAGG TGGCA | 113 |
| RPL37A | ribosomal protein L37a | GCATGAAGACA GTGGCT | 57 | GCGGACTTTACC GTGAC | 114 |

TABLE 1C

| Gene Symbol | Gene name | Forward primer | SEQ ID | Reverse primer | SEQ ID |
|---|---|---|---|---|---|
| CDH5 | cadherin 5, type 2, VE-cadherin (vascular epithelium) | AAGAGAGATTG GATTTGGAACC | 1 | TTCTTGCGACTCACGCT | 58 |
| CLEC3B | C-type lectin domain family 3, member B | CCAGAAGCCCA AGAAGATTGTA | 2 | GCTCCTCAAACAT CTTTGTGTTCA | 59 |
| PAICS | phosphoribosylami noimidazole carboxylase, phosphoribosylami noimidazole succinocarboxamide synthetase | AATCCTGGTGT CAAGGAAG | 3 | GACCACTGTGGG TCATTATT | 60 |
| PAK1 | p21/Cdc42/Rac1-activated kinase 1 (STE20 homolog, yeast) | GGACCGATTTT ACCGATCC | 4 | GAAATCTCTGGC CGCTC | 61 |
| PECAM1 | platelet/endothelial cell adhesion molecule (CD31 antigen) | ACAGTCCAGAT AGTCGTATGT | 5 | ACTGGGCATCAT AAGAAATCC | 62 |
| TFAP2A | transcription factor AP-2 alpha (activating enhancer | GTCTCCGCCATC CCTAT | 6 | ACTGAACAGAAG ACTTCGT | 63 |

TABLE 1C -continued

| Gene Symbol | Gene name | Forward primer | SEQ ID | Reverse primer | SEQ ID |
|---|---|---|---|---|---|
| | binding protein 2 alpha) | | | | |
| ACVR1 | activin A receptor, type 1 | ACTGGTGTAAC AGGAACAT | 7 | AACCTCCAAGTG GAAATTCT | 64 |
| CDKN2C | cyclin-dependent kinase inhibitor 2C (p18, inhibits CDK4) | TTTGGAAGGAC TGCGCT | 8 | TCGGTCTTTCAAA TCGGGATTA | 65 |
| CIB1 | calcium and integrin binding 1 (calmyrin) | CACGTCATCTCC CGTTC | 9 | CTGCTGTCACAG GACAAT | 66 |
| INSM1 | insulinoma-associated 1 | ATTGAACTTCCC ACACGA | 10 | AAGGTAAAGCCA GACTCCA | 67 |
| LRP10 | low density lipo-protein receptor-related protein 10 | GGAACAGACTG TCACCAT | 11 | GGGAGCGTAGGG TTAAG | 68 |
| STMN1 | stathmin 1/oncoprotein 18 | TCAGAGTGTGTG GTCAGGC | 12 | CAGTGTATTCTGC ACAATCAAC | 69 |
| CAPG | capping protein (actin filament), gelsolin-like | GGGACAGCTTC AACACT | 13 | GTTCCAGGATGTT GGACTTTC | 70 |
| CHGA | chromogranin A (parathyroid secretory protein 1) | CCTGTGAACAG CCCTATG | 14 | GGAAAGTGTGTC GGAGAT | 71 |
| LGALS3 | lectin, galactoside-binding, soluble, 3 (galectin 3) | TTCTGGGCACG GTGAAG | 15 | AGGCAACATCAT TCCCTC | 72 |
| MAPRE3 | microtubule-associated protein, RP/EB family, member 3 | GGCCAAACTAG AGCACGAATA | 16 | GTCAACACCCAT CTTCTTAAA | 73 |
| SFN | stratifin | TCAGCAAGAAG GAGATGCC | 17 | CGTAGTGGAAGA CGGAAA | 74 |
| SNAP91 | synaptosomal-associated protein, 91 kDa homolog (mouse) | GTGCTCCCTCTC CATTAAGTA | 18 | CTGGTGTAGAATT AGGAGACGTA | 75 |
| ABCC5 | ATP-binding cassette, sub-family C (CFTR/MRP), member 5 | CAAGTTCAGGA GAACTCGAC | 19 | GGCATCAAGAGA GAGGC | 76 |
| ALDH3B1 | aldehyde dehydro-genase 3 family, member B1 | GGCTGTGGTTA TGCGATAG | 20 | GATAAAGAGTTA CAAGCTCCTCTG | 77 |
| ANTXR1 | Anthrax toxin receptor 1 | ACCCGAGGAAC AACCTTA | 21 | TCTAGGCCTTGAC GGAT | 78 |
| BMP7 | Bone morphogenetic protein 7 (osteogenic protein 1) | CCCTCTCCATTC CCTACA | 22 | TTTGGGCAAACCTCGGTA A | 79 |
| CACNB1 | calcium channel, voltage-dependent, beta 1 subunit | CAGAGCGCCAG GCATTA | 23 | GCACAGCAAATG CCACT | 80 |
| CBX1 | chromobox homolog 1 (HP1 beta homolog *Drosophila*) | CCACTGGCTGA GGTGTTA | 24 | CTTGTCTTTCCCT ACTGTCTTAC | 81 |
| CYB5B | cytochrome b5 tye B (outer mitochondrial membrane) | TGGGCGAGTCT ACGATG | 25 | CTTGTTCCAGCAG AACCT | 82 |

TABLE 1C -continued

| Gene Symbol | Gene name | Forward primer | SEQ ID | Reverse primer | SEQ ID |
|---|---|---|---|---|---|
| DOK1 | docking, protein 1, 62 kDa (downstream of tyrosine kinase 1) | CTTTCTGCCCTGGAGATG | 26 | CAGTCCTCTGCACCGTTA | 83 |
| DSC3 | desmocollin 3 | GCGCCATTTGCTAGAGATA | 27 | CATCCAGATCCCTCACAT | 84 |
| FEN1 | flap structure-specific endonuclease 1 | AGAGAAGATGGGCAGAAAG | 28 | CCAAGACACAGCCAGTAAT | 85 |
| FOXH1 | forkhead box H1 | GCCCAGATCATCCGTCA | 29 | TTTCCAGCCCTCGTAGTC | 86 |
| GJB5 | gap junction protein, beta 5 (connexin 31.1) | ACCACAAGGACTTCGAC | 30 | GGGACACAGGGAAGAAC | 87 |
| HOXD1 | homeobox D1 | GCTCCGCTGCTATCTTT | 31 | GTCTGCCACTCTGCAAC | 88 |
| HPN | Hepsin (transmembrane protease, serine 1) | AGCGGCCAGGTGGATTA | 32 | GTCGGCTGACGCTTTGA | 89 |
| HYAL2 | hyaluronoglucosam | ATGGGCTTTGGGAGCATA | 33 | GAACAAGTCAGTCTAGGGAATAC | 90 |
| ICA1 | islet cell autoantigen 1, 69 kDa | GACCTGGATGCCAAGCTA | 34 | TGCTTTCGATAAGTCCAGACA | 91 |
| ICAM5 | intercellular adhesion molecule 5, telencephalin | CCGGCTCTTGGAAGTTG | 35 | CCTCTGAGGCTGGAAACA | 92 |
| ITGA6 | integrin, alpha 6 | ACGCGGATCGAGTTTGATAA | 36 | ATCCACTGATCTTCCTTGC | 93 |
| LIPE | lipase, | CGCAAGTCCCAGAAGAT | 37 | CAGTGCTGCTTCA | 94 |
| MF3 | malic enzyme 3, NADP(+)-dependent, Mitochondrial | CGCGGATACGATGTCAC | 38 | CCTTTCTTCAAGGGTAAAGGC | 95 |
| MGRN1 | mahogunin, ring finger 1 | GAACTCGGCCTATCGCT | 39 | TCGAATTTCTCTCCTCCCAT | 96 |
| MYBPH | mysoin binding protein H | TCTGACCTCATCATCGGCAA | 40 | CTGAGTCCACACAGGTTT | 97 |
| MYO7A | mysosin VIIA | GAGGTGAAGCAAACTACGGA | 41 | CCCATACTTGTTGATGGCAATTA | 98 |
| NFIL3 | nuclear factor, interlukin 3 regulated | ACTCTCCACAAAGCTCG | 42 | TCCTGCGTGTGTTCTACT | 99 |
| PIK3C2A | phosphoinositide-3-kinase, class 2, alpha polypeptide | GGATTTCAGCTACCAGTTACTT | 43 | AGTCATCATGTACCCAGCA | 100 |
| PLEKHA6 | pleckstrin homology domain containing, family A member 6 | TTCGTCCTGGTGGATCG | 44 | CCCAGGATACTCTCTTCCTT | 101 |
| PSMD14 | proteasome (prosome, macropain) 26S subunit, non-ATPase, 14 | AGTGATTGATGTGTTTGCTATG | 45 | CACTGGATCAACTGCCTC | 102 |
| SCD5 | stearoyl-CoA desaturase 5 | CAAAGCCAAGCCACTCACTC | 46 | CAGCTGTCACACCCAGAGC | 103 |

TABLE 1C -continued

| Gene Symbol | Gene name | Forward primer | SEQ ID | Reverse primer | SEQ ID |
|---|---|---|---|---|---|
| SIAH2 | seven in absentia homolog 2 (Drosophila) | CTCGGCAGTCC TGTTTC | 47 | CGTATGGTGCAG GGTCA | 104 |
| TCF2 | transcription factor 2, hepatic; LF-B3; variant hepatic nuclear factor | ACACCTGGTAC GTCAGAA | 48 | TCTGGACTGTCTG GTTGAAT | 105 |
| TCP1 | t-complex 1 | ATGCCCAAGAG AATCGTAAA | 49 | CCTGTACACCAA GCTTCAT | 106 |
| TTF1 | thyroid transcription factor 1 | ATGAGTCCAAA GCACACGA | 50 | CCATGCCCACTTT CTTGTA | 107 |
| TRIM29 | triparite morif-contain 29 | TGAGATTGAGG ATGAAGCTGAG | 51 | CATTGGTGGTGA AGCTCTTG | 108 |
| TUBA1 | tubulin, aplha 1 | CCGACTCAACG TGAGAC | 52 | CCTGGACTGAGA TGCATT | 109 |

TABLE 2

| Gene Symbol | Gene name | Forward primer | SEQ ID | Reverse primer | SEQ ID |
|---|---|---|---|---|---|
| CDH5 | cadherin 5, type 2, VE-cadherin (vascular epithelium) | AAGAGAGATTG GATTTGGAACC | 1 | TTCTTGCGACTCACGCT | 58 |
| PAICS | phosphoribosylami noimidazole carboxylase, phosphoribosylami noimidazole succinocarboxamide synthetase | AATCCTGGTGT CAAGGAAG | 3 | GACCACTGTGGG TCATTATT | 60 |
| PAK1 | p21/Cdc42/Rac1-activated kinase 1 (STE20 homolog, yeast) | GGACCGATTTT ACCGATCC | 4 | GAAATCTCTGGC CGCTC | 61 |
| PECAM1 | platelet/endothelial cell adhesion molecule (CD31 antigen) | ACAGTCCAGAT AGTCGTATGT | 5 | ACTGGGCATCAT AAGAAATCC | 62 |
| TFAP2A | transcription factor AP-2 alpha (activating enhancer binding protein 2 alpha) | GTCTCCGCCATC CCTAT | 6 | ACTGAACAGAAG ACTTCGT | 63 |
| ACVR1 | activin A receptor, type 1 | ACTGGTGTAAC AGGAACAT | 7 | AACCTCCAAGTG GAAATTCT | 64 |
| CDKN2C | cyclin-dependent kinase inhibitor 2C (p18, inhibits CDK4) | TTTGGAAGGAC TGCGCT | 8 | TCGGTCTTTCAAA TCGGGATTA | 65 |
| CIB1 | calcium and integrin binding 1 (calmyrin) | CACGTCATCTCC CGTTC | 9 | CTGCTGTCACAG GACAAT | 66 |
| INSM1 | insulinoma-associated 1 | ATTGAACTTCCC ACACGA | 10 | AAGGTAAAGCCA GACTCCA | 67 |
| LRP10 | low density lipo-protein receptor-related protein 10 | GGAACAGACTG TCACCAT | 11 | GGGAGCGTAGGG TTAAG | 68 |
| STMN1 | stathmin 1/oncoprotein 18 | TCAGAGTGTGTG GTCAGGC | 12 | CAGTGTATTCTGC ACAATCAAC | 69 |

TABLE 2-continued

| Gene Symbol | Gene name | Forward primer | SEQ ID | Reverse primer | SEQ ID |
|---|---|---|---|---|---|
| CAPG | capping protein (actin filament), gelsolin-like | GGGACAGCTTC AACACT | 13 | GTTCCAGGATGTT GGACTTTC | 70 |
| CHGA | chromogranin A (parathyroid secretory protein 1) | CCTGTGAACAG CCCTATG | 14 | GGAAAGTGTGTC GGAGAT | 71 |
| LGALS3 | lectin, galactoside-binding, soluble, 3 (galectin 3) | TTCTGGGCACG GTGAAG | 15 | AGGCAACATCAT TCCCTC | 72 |
| MAPRE3 | microtubule-associated protein, RP/EB family, member 3 | GGCCAAACTAG AGCACGAATA | 16 | GTCAACACCCAT CTTCTTAAA | 73 |
| SFN | stratifin | TCAGCAAGAAG GAGATGCC | 17 | CGTAGTGGAAGA CGGAAA | 74 |
| SNAP91 | synaptosomal-associated protein, 91 kDa homolog (mouse) | GTGCTCCCTCTC CATTAAGTA | 18 | CTGGTGTAGAATT AGGAGACGTA | 75 |
| ABCC5 | ATP-binding cassette, sub-family C (CFTR/MRP), member 5 | CAAGTTCAGGA GAACTCGAC | 19 | GGCATCAAGAGA GAGGC | 76 |
| ALDH3B1 | aldehyde dehydrogenase 3 family, member B1 | GGCTGTGGTTA TGCGATAG | 20 | GATAAAGAGTTA CAAGCTCCTCTG | 77 |
| ANTXR1 | Anthrax toxin receptor 1 | ACCCGAGGAAC AACCTTA | 21 | TCTAGGCCTTGAC GGAT | 78 |
| CACNB1 | calcium channel, voltage-dependent, beta 1 subunit | CAGAGCGCCAG GCATTA | 23 | GCACAGCAAATG CCACT | 80 |
| CBX1 | chromobox homolog 1 (HP1 beta homolog Drosophila) | CCACTGGCTGA GGTGTTA | 24 | CTTGTCTTTCCCT ACTGTCTTAC | 81 |
| CYB5B | cytochrome b5 tye B (outer mitochondrial membrane) | TGGGCGAGTCT ACGATG | 25 | CTTGTTCCAGCAG AACCT | 82 |
| DOK1 | docking, protein 1, 62 kDa (downstream of tyrosine kinase 1) | CTTTCTGCCCTG GAGATG | 26 | CAGTCCTCTGCAC CGTTA | 83 |
| DSC3 | desmocollin 3 | GCGCCATTTGCT AGAGATA | 27 | CATCCAGATCCCT CACAT | 84 |
| FEN1 | flap structure-specific endonuclease 1 | AGAGAAGATGG GCAGAAAG | 28 | CCAAGACACAGC CAGTAAT | 85 |
| FOXH1 | forkhead box H1 | GCCCAGATCAT CCGTCA | 29 | TTTCCAGCCCTCG TAGTC | 86 |
| GJB5 | gap junction protein, beta 5 (connexin 31.1) | ACCACAAGGAC TTCGAC | 30 | GGGACACAGGGA AGAAC | 87 |
| HOXD1 | homeobox D1 | GCTCCGCTGCT ATCTTT | 31 | GTCTGCCACTCTG CAAC | 88 |
| HPN | Hepsin (transmembrane protease, serine 1) | AGCGGCCAGGT GGATTA | 32 | GTCGGCTGACGC TTTGA | 89 |
| HYAL2 | hyaluronoglucosam | ATGGGCTTTGG GAGCATA | 33 | GAACAAGTCAGT CTAGGGAATAC | 90 |

TABLE 2-continued

| Gene Symbol | Gene name | Forward primer | SEQ ID | Reverse primer | SEQ ID |
|---|---|---|---|---|---|
| ICA1 | islet cell autoantigen 1, 69 kDa | GACCTGGATGC CAAGCTA | 34 | TGCTTTCGATAAG TCCAGACA | 91 |
| ICAM5 | intercellular adhesion molecule 5, telencephalin | CCGGCTCTTGG AAGTTG | 35 | CCTCTGAGGCTG GAAACA | 92 |
| ITGA6 | integrin, alpha 6 | ACGCGGATCGA GTTTGATAA | 36 | ATCCACTGATCTT CCTTGC | 93 |
| LIPE | lipase, | CGCAAGTCCCA GAAGAT | 37 | CAGTGCTGCTTCA | 94 |
| ME3 | malic enzyme 3, NADP(+)-dependent, Mitochondrial | CGCGGATACGA TGTCAC | 38 | CCTTTCTTCAAGG GTAAAGGC | 95 |
| MGRN1 | mahogunin, ring finger 1 | GAACTCGGCCT ATCGCT | 39 | TCGAATTTCTCTC CTCCCAT | 96 |
| MYBPH | mysoin binding protein H | TCTGACCTCATC ATCGGCAA | 40 | CTGAGTCCACAC AGGTTT | 97 |
| MYO7A | mysosin VIIA | GAGGTGAAGCA AACTACGGA | 41 | CCCATACTTGTTG ATGGCAATTA | 98 |
| NFIL3 | nuclear factor, interlukin 3 regulated | ACTCTCCACAA AGCTCG | 42 | TCCTGCGTGTGTT CTACT | 99 |
| PIK3C2A | phosphoinositide-3-kinase, class 2, alpha polypeptide | GGATTTCAGCT ACCAGTTACTT | 43 | AGTCATCATGTAC CCAGCA | 100 |
| PLEKHA6 | pleckstrin homology domain containing, family A member 6 | TTCGTCCTGGTG GATCG | 44 | CCCAGGATACTCT CTTCCTT | 101 |
| PSMD14 | proteasome (prosome, macropain) 26S subunit, non-ATPase, 14 | AGTGATTGATG TGTTTGCTATG | 45 | CACTGGATCAAC TGCCTC | 102 |
| SCD5 | stearoyl-CoA desaturase 5 | CAAAGCCAAGC CACTCACTC | 46 | CAGCTGTCACAC CCAGAGC | 103 |
| SIAH2 | seven in absentia homolog 2 (Drosophila) | CTCGGCAGTCC TGTTTC | 47 | CGTATGGTGCAG GGTCA | 104 |
| TCF2 | transcription factor 2, hepatic; LF-B3; variant hepatic nuclear factor | ACACCTGGTAC GTCAGAA | 48 | TCTGGACTGTCTG GTTGAAT | 105 |
| TCP1 | t-complex 1 | ATGCCCAAGAG AATCGTAAA | 49 | CCTGTACACCAA GCTTCAT | 106 |
| TTF1 | thyroid transcription factor 1 | ATGAGTCCAAA GCACACGA | 50 | CCATGCCCACTTT CTTGTA | 107 |
| TRIM29 | triparite morif-contain 29 | TGAGATTGAGG ATGAAGCTGAG | 51 | CATTGGTGGTGA AGCTCTTG | 108 |
| TUBA1 | tubulin, aplha 1 | CCGACTCAACG TGAGAC | 52 | CCTGGACTGAGA TGCATT | 109 |
| CFL1 | cofilin 1 (non-muscle) | GTGCCCTCTCCT TTTCG | 53 | TTCATGTCGTTGA ACACTTG | 110 |
| EEF1A1 | eukaryotic translation elongation factor 1 alpha 1 | CGTTCTTTTTCG CAACGG | 54 | CATTTTGGCTTTT AGGGGTAG | 111 |

TABLE 2-continued

| Gene Symbol | Gene name | Forward primer | SEQ ID | Reverse primer | SEQ ID |
|---|---|---|---|---|---|
| RPL10 | ribosomal protein L10 | GGTGTGCCACT GAAGAT | 55 | GGCAGAAGCGAG ACTTT | 112 |
| RPL28 | ribosomal protein L28 | GTGTCGTGGTG GTCATT | 56 | GCACATAGGAGG TGGCA | 113 |
| RPL37A | ribosomal protein L37a | GCATGAAGACA GTGGCT | 57 | GCGGACTTTACC GTGAC | 114 |

TABLE 3

| Gene Symbol | Gene name | Forward primer | SEQ ID | Reverse primer | SEQ ID |
|---|---|---|---|---|---|
| CDH5 | cadherin 5, type 2, VE-cadherin (vascular epithelium) | AAGAGAGATTG GATTTGGAACC | 1 | TTCTTGCGACTCACGCT | 58 |
| CLEC3B | C-type lectin domain family 3, member B | CCAGAAGCCCA AGAAGATTGTA | 2 | GCTCCTCAAACAT CTTTGTGTTCA | 59 |
| PAICS | phosphoribosylami noimidazole carboxylase, phosphoribosylami noimidazole succinocarboxamide synthetase | AATCCTGGTGT CAAGGAAG | 3 | GACCACTGTGGG TCATTATT | 60 |
| PAK1 | p21/Cdc42/Rac1-activated kinase 1 (STE20 homolog, yeast) | GGACCGATTTT ACCGATCC | 4 | GAAATCTCTGGC CGCTC | 61 |
| TFAP2A | transcription factor AP-2 alpha (activating enhancer binding protein 2 alpha) | GTCTCCGCCATC CCTAT | 6 | ACTGAACAGAAG ACTTCGT | 63 |
| ACVR1 | activin A receptor, type 1 | ACTGGTGTAAC AGGAACAT | 7 | AACCTCCAAGTG GAAATTCT | 64 |
| CDKN2C | cyclin-dependent kinase inhibitor 2C (p18, inhibits CDK4) | TTTGGAAGGAC TGCGCT | 8 | TCGGTCTTTCAAA TCGGGATTA | 65 |
| INSM1 | insulinoma-associated 1 | ATTGAACTTCCC ACACGA | 10 | AAGGTAAAGCCA GACTCCA | 67 |
| LRP10 | low density lipo-protein receptor-related protein 10 | GGAACAGACTG TCACCAT | 11 | GGGAGCGTAGGG TTAAG | 68 |
| STMN1 | stathmin 1/oncoprotein 18 | TCAGAGTGTGTG GTCAGGC | 12 | CAGTGTATTCTGC ACAATCAAC | 69 |
| CAPG | capping protein (actin filament), gelsolin-like | GGGACAGCTTC AACACT | 13 | GTTCCAGGATGTT GGACTTTC | 70 |
| CHGA | chromogranin A (parathyroid secretory protein 1) | CCTGTGAACAG CCCTATG | 14 | GGAAAGTGTGTC GGAGAT | 71 |
| LGALS3 | lectin, galactoside-binding, soluble, 3 (galectin 3) | TTCTGGGCACG GTGAAG | 15 | AGGCAACATCAT TCCCTC | 72 |
| MAPRE3 | microtubule-associated protein, RP/EB family, member 3 | GGCCAAACTAG AGCACGAATA | 16 | GTCAACACCCAT CTTCTTAAA | 73 |

TABLE 3-continued

| Gene Symbol | Gene name | Forward primer | SEQ ID | Reverse primer | SEQ ID |
|---|---|---|---|---|---|
| SFN | stratifin | TCAGCAAGAAGGAGATGCC | 17 | CGTAGTGGAAGACGGAAA | 74 |
| SNAP91 | synaptosomal-associated protein, 91 kDa homolog (mouse) | GTGCTCCCTCTCCATTAAGTA | 18 | CTGGTGTAGAATTAGGAGACGTA | 75 |
| ABCC5 | ATP-binding cassette, sub-family C (CFTR/MRP), member 5 | CAAGTTCAGGAGAACTCGAC | 19 | GGCATCAAGAGAGAGGC | 76 |
| ALDH3B1 | aldehyde dehydrogenase 3 family, member B1 | GGCTGTGGTTATGCGATAG | 20 | GATAAAGAGTTACAAGCTCCTCTG | 77 |
| ANTXR1 | Anthrax toxin receptor 1 | ACCCGAGGAACAACCTTA | 21 | TCTAGGCCTTGACGGAT | 78 |
| CACNB1 | calcium channel, voltage-dependent, beta 1 subunit | CAGAGCGCCAGGCATTA | 23 | GCACAGCAAATGCCACT | 80 |
| CBX1 | chromobox homolog 1 (HP1 beta homolog Drosophila) | CCACTGGCTGAGGTGTTA | 24 | CTTGTCTTTCCCTACTGTCTTAC | 81 |
| CYB5B | cytochrome b5 tye B (outer mitochondrial membrane) | TGGGCGAGTCTACGATG | 25 | CTTGTTCCAGCAGAACCT | 82 |
| DOK1 | docking, protein 1, 62 kDa (downstream of tyrosine kinase 1) | CTTTCTGCCCTGGAGATG | 26 | CAGTCCTCTGCACCGTTA | 83 |
| DSC3 | desmocollin 3 | GCGCCATTTGCTAGAGATA | 27 | CATCCAGATCCCTCACAT | 84 |
| FEN1 | flap structure-specific endonuclease 1 | AGAGAAGATGGGCAGAAAG | 28 | CCAAGACACAGCCAGTAAT | 85 |
| GJB5 | gap junction protein, beta 5 (connexin 31.1) | ACCACAAGGACTTCGAC | 30 | GGGACACAGGGAAGAAC | 87 |
| HOXD1 | homeobox D1 | GCTCCGCTGCTATCTTT | 31 | GTCTGCCACTCTGCAAC | 88 |
| HPN | Hepsin (transmembrane protease, serine 1) | AGCGGCCAGGTGGATTA | 32 | GTCGGCTGACGCTTTGA | 89 |
| HYAL2 | hyaluronoglucosam | ATGGGCTTTGGGAGCATA | 33 | GAACAAGTCAGTCTAGGGAATAC | 90 |
| ICA1 | islet cell autoantigen 1, 69 kDa | GACCTGGATGCCAAGCTA | 34 | TGCTTTCGATAAGTCCAGACA | 91 |
| ICAM5 | intercellular adhesion molecule 5, telencephalin | CCGGCTCTTGGAAGTTG | 35 | CCTCTGAGGCTGGAAACA | 92 |
| ITGA6 | integrin, alpha 6 | ACGCGGATCGAGTTTGATAA | 36 | ATCCACTGATCTTCCTTGC | 93 |
| LIPE | lipase, | CGCAAGTCCCAGAAGAT | 37 | CAGTGCTGCTTCA | 94 |
| ME3 | malic enzyme 3, NADP(+)-dependent, Mitochondrial | CGCGGATACGATGTCAC | 38 | CCTTTCTTCAAGGGTAAAGGC | 95 |
| MGRN1 | mahogunin, ring finger 1 | GAACTCGGCCTATCGCT | 39 | TCGAATTTCTCTCCTCCCAT | 96 |

TABLE 3-continued

| Gene Symbol | Gene name | Forward primer | SEQ ID | Reverse primer | SEQ ID |
|---|---|---|---|---|---|
| MYBPH | mysoin binding protein H | TCTGACCTCATCATCGGCAA | 40 | CTGAGTCCACACAGGTTT | 97 |
| MYO7A | mysosin VIIA | GAGGTGAAGCAAACTACGGA | 41 | CCCATACTTGTTGATGGCAATTA | 98 |
| NFIL3 | nuclear factor, interlukin 3 regulated | ACTCTCCACAAAGCTCG | 42 | TCCTGCGTGTGTTCTACT | 99 |
| PIK3C2A | phosphoinositide-3-kinase, class 2, alpha polypeptide | GGATTTCAGCTACCAGTTACTT | 43 | AGTCATCATGTACCCAGCA | 100 |
| PLEKHA6 | pleckstrin homology domain containing, family A member 6 | TTCGTCCTGGTGGATCG | 44 | CCCAGGATACTCTCTTCCTT | 101 |
| PSMD14 | proteasome (prosome, macropain) 26S subunit, non-ATPase, 14 | AGTGATTGATGTGTTTGCTATG | 45 | CACTGGATCAACTGCCTC | 102 |
| SCD5 | stearoyl-CoA desaturase 5 | CAAAGCCAAGCCACTCACTC | 46 | CAGCTGTCACACCCAGAGC | 103 |
| SIAH2 | seven in absentia homolog 2 (Drosophila) | CTCGGCAGTCCTGTTTC | 47 | CGTATGGTGCAGGGTCA | 104 |
| TCF2 | transcription factor 2, hepatic; LF-B3; variant hepatic nuclear factor | ACACCTGGTACGTCAGAA | 48 | TCTGGACTGTCTGGTTGAAT | 105 |
| TCP1 | t-complex 1 | ATGCCCAAGAGAATCGTAAA | 49 | CCTGTACACCAAGCTTCAT | 106 |
| TTF1 | thyroid transcription factor 1 | ATGAGTCCAAAGCACACGA | 50 | CCATGCCCACTTTCTTGTA | 107 |
| TRIM29 | triparite morif-contain 29 | TGAGATTGAGGATGAAGCTGAG | 51 | CATTGGTGGTGAAGCTCTTG | 108 |
| CFL1 | cofilin 1 (non-muscle) | GTGCCCTCTCCTTTTCG | 53 | TTCATGTCGTTGAACACTTG | 110 |
| EEF1A1 | eukaryotic translation elongation factor 1 alpha 1 | CGTTCTTTTTCGCAACGG | 54 | CATTTTGGCTTTTAGGGGTAG | 111 |
| RPL10 | ribosomal protein L10 | GGTGTGCCACTGAAGAT | 55 | GGCAGAAGCGAGACTTT | 112 |
| RPL28 | ribosomal protein L28 | GTGTCGTGGTGGTCATT | 56 | GCACATAGGAGGTGGCA | 113 |
| RPL37A | ribosomal protein L37a | GCATGAAGACAGTGGCT | 57 | GCGGACTTTACCGTGAC | 114 |

TABLE 4

| Gene Symbol | Gene name | Forward primer | SEQ ID | Reverse primer | SEQ ID |
|---|---|---|---|---|---|
| ACVR1 | activin A receptor, type 1 | ACTGGTGTAACAGGAACAT | 7 | AACCTCCAAGTGGAAATTCT | 64 |
| CDKN2C | cyclin-dependent kinase inhibitor 2C (p18, inhibits CDK4) | TTTGGAAGGACTGCGCT | 8 | TCGGTCTTTCAAATCGGGATTA | 65 |

TABLE 4-continued

| Gene Symbol | Gene name | Forward primer | SEQ ID | Reverse primer | SEQ ID |
|---|---|---|---|---|---|
| CIB1 | calcium and integrin binding 1 (calmyrin) | CACGTCATCTCC CGTTC | 9 | CTGCTGTCACAG GACAAT | 66 |
| INSM1 | insulinoma-associated 1 | ATTGAACTTCCC ACACGA | 10 | AAGGTAAAGCCA GACTCCA | 67 |
| LRP10 | low density lipo-protein receptor-related protein 10 | GGAACAGACTG TCACCAT | 11 | GGGAGCGTAGGG TTAAG | 68 |
| STMN1 | stathmin 1/oncoprotein 18 | TCAGAGTGTGTG GTCAGGC | 12 | CAGTGTATTCTGC ACAATCAAC | 69 |

TABLE 5

| Gene Symbol | Gene name | Forward primer | SEQ ID | Reverse primer | SEQ ID |
|---|---|---|---|---|---|
| CAPG | capping protein (actin filament), gelsolin-like | GGGACAGCTTC AACACT | 13 | GTTCCAGGATGTT GGACTTTC | 70 |
| CHGA | chromogranin A (parathyroid secretory protein 1) | CCTGTGAACAG CCCTATG | 14 | GGAAAGTGTGTC GGAGAT | 71 |
| LGALS3 | lectin, galactoside-binding, soluble, 3 (galectin 3) | TTCTGGGCACG GTGAAG | 15 | AGGCAACATCAT TCCCTC | 72 |
| MAPRE3 | microtubule-associated protein, RP/EB family, member 3 | GGCCAAACTAG AGCACGAATA | 16 | GTCAACACCCAT CTTCTTAAA | 73 |
| SFN | stratifin | TCAGCAAGAAG GAGATGCC | 17 | CGTAGTGGAAGA CGGAAA | 74 |
| SNAP91 | synaptosomal-associated protein, 91 kDa homolog (mouse) | GTGCTCCCTCTC CATTAAGTA | 18 | CTGGTGTAGAATT AGGAGACGTA | 75 |

TABLE 6

| Gene Symbol | Gene name | Forward primer | SEQ ID | Reverse primer | SEQ ID |
|---|---|---|---|---|---|
| ABCC5 | ATP-binding cassette, sub-family C (CFTR/MRP), member 5 | CAAGTTCAGGA GAACTCGAC | 19 | GGCATCAAGAGA GAGGC | 76 |
| ALDH3B1 | aldehyde dehydro-genase 3 family, member B1 | GGCTGTGGTTA TGCGATAG | 20 | GATAAAGAGTTA CAAGCTCCTCTG | 77 |
| ANTXR1 | Anthrax toxin receptor 1 | ACCCGAGGAAC AACCTTA | 21 | TCTAGGCCTTGAC GGAT | 78 |
| BMP7 | Bone morphogenetic protein 7 (osteogenic protein 1) | CCCTCTCCATTC CCTACA | 22 | TTTGGGCAAACCTCGGTA A | 79 |
| CACNB1 | calcium channel, voltage-dependent, beta 1 subunit | CAGAGCGCCAG GCATTA | 23 | GCACAGCAAATG CCACT | 80 |

TABLE 6-continued

| Gene Symbol | Gene name | Forward primer | SEQ ID | Reverse primer | SEQ ID |
|---|---|---|---|---|---|
| CBX1 | chromobox homolog 1 (HP1 beta homolog Drosophila) | CCACTGGCTGA GGTGTTA | 24 | CTTGTCTTTCCCT ACTGTCTTAC | 81 |
| CYB5B | cytochrome b5 tye B (outer mitochondrial membrane) | TGGGCGAGTCT ACGATG | 25 | CTTGTTCCAGCAG AACCT | 82 |
| DOK1 | docking, protein 1, 62 kDa (downstream of tyrosine kinase 1) | CTTTCTGCCCTG GAGATG | 26 | CAGTCCTCTGCAC CGTTA | 83 |
| DSC3 | desmocollin 3 | GCGCCATTTGCT AGAGATA | 27 | CATCCAGATCCCT CACAT | 84 |
| FEN1 | flap structure-specific endonuclease 1 | AGAGAAGATGG GCAGAAAG | 28 | CCAAGACACAGC CAGTAAT | 85 |
| FOXH1 | forkhead box H1 | GCCCAGATCAT CCGTCA | 29 | TTTCCAGCCCTCG TAGTC | 86 |
| GJB5 | gap junction protein, beta 5 (connexin 31.1) | ACCACAAGGAC TTCGAC | 30 | GGGACACAGGGA AGAAC | 87 |
| HOXD1 | homeobox D1 | GCTCCGCTGCT ATCTTT | 31 | GTCTGCCACTCTG CAAC | 88 |
| HPN | Hepsin (transmembrane protease, serine 1) | AGCGGCCAGGT GGATTA | 32 | GTCGGCTGACGC TTTGA | 89 |
| HYAL2 | hyaluronoglucosam | ATGGGCTTTGG GAGCATA | 33 | GAACAAGTCAGT CTAGGGAATAC | 90 |
| ICA1 | islet cell autoantigen 1, 69 kDa | GACCTGGATGC CAAGCTA | 34 | TGCTTTCGATAAG TCCAGACA | 91 |
| ICAM5 | intercellular adhesion molecule 5, telencephalin | CCGGCTCTTGG AAGTTG | 35 | CCTCTGAGGCTG GAAACA | 92 |
| ITGA6 | integrin, alpha 6 | ACGCGGATCGA GTTTGATAA | 36 | ATCCACTGATCTT CCTTGC | 93 |
| LIPE | lipase, hormone-sensitive | CGCAAGTCCCA GAAGAT | 37 | CAGTGCTGCTTCA GACACA | 94 |
| MF3 | malic enzyme 3, NADP(+)-dependent, Mitochondrial | CGCGGATACGA TGTCAC | 38 | CCTTTCTTCAAGG GTAAAGGC | 95 |
| MGRN1 | mahogunin, ring finger 1 | GAACTCGGCCT ATCGCT | 39 | TCGAATTTCTCTC CTCCCAT | 96 |
| MYBPH | mysoin binding protein H | TCTGACCTCATC ATCGGCAA | 40 | CTGAGTCCACAC AGGTTT | 97 |
| MYO7A | mysosin VIIA | GAGGTGAAGCA AACTACGGA | 41 | CCCATACTTGTTG ATGGCAATTA | 98 |
| NFIL3 | nuclear factor, interlukin 3 regulated | ACTCTCCACAA AGCTCG | 42 | TCCTGCGTGTGTT CTACT | 99 |
| PIK3C2A | phosphoinositide-3-kinase, class 2, alpha polypeptide | GGATTTCAGCT ACCAGTTACTT | 43 | AGTCATCATGTAC CCAGCA | 100 |
| PLEKHA6 | pleckstrin homology domain containing, family A member 6 | TTCGTCCTGGTG GATCG | 44 | CCCAGGATACTCT CTTCCTT | 101 |
| PSMD14 | proteasome (prosome, macropain) 26S | AGTGATTGATG TGTTTGCTATG | 45 | CACTGGATCAAC TGCCTC | 102 |

TABLE 6-continued

| Gene Symbol | Gene name | Forward primer | SEQ ID | Reverse primer | SEQ ID |
|---|---|---|---|---|---|
| | subunit, non-ATPase, 14 | | | | |
| SCD5 | stearoyl-CoA desaturase 5 | CAAAGCCAAGC CACTCACTC | 46 | CAGCTGTCACAC CCAGAGC | 103 |
| SIAH2 | seven in absentia homolog 2 (Drosophila) | CTCGGCAGTCC TGTTTC | 47 | CGTATGGTGCAG GGTCA | 104 |
| TCF2 | transcription factor 2, hepatic; LF-B3; variant hepatic nuclear factor | ACACCTGGTAC GTCAGAA | 48 | TCTGGACTGTCTG GTTGAAT | 105 |
| TCP1 | t-complex 1 | ATGCCCAAGAG AATCGTAAA | 49 | CCTGTACACCAA GCTTCAT | 106 |
| TTF1 | thyroid transcription factor 1 | ATGAGTCCAAA GCACACGA | 50 | CCATGCCCACTTT CTTGTA | 107 |
| TRIM29 | triparite morif-contain 29 | TGAGATTGAGG ATGAAGCTGAG | 51 | CATTGGTGGTGA AGCTCTTG | 108 |
| TUBA1 | tubulin, aplha 1 | CCGACTCAACG TGAGAC | 52 | CCTGGACTGAGA TGCATT | 109 |

Isolated mRNA can be used in hybridization or amplification assays that include, but are not limited to, Southern or Northern analyses, PCR analyses and probe arrays, NanoString Assays. One method for the detection of mRNA levels involves contacting the isolated mRNA or synthesized cDNA with a nucleic acid molecule (probe) that can hybridize to the mRNA encoded by the gene being detected. The nucleic acid probe can be, for example, a cDNA, or a portion thereof, such as an oligonucleotide of at least 7, 15, 30, 50, 100, 250, or 500 nucleotides in length and sufficient to specifically hybridize under stringent conditions to the non-natural cDNA or mRNA biomarker of the present invention.

As explained above, in one embodiment, once the mRNA is obtained from a sample, it is converted to complementary DNA (cDNA) in a hybridization reaction. cDNA does not exist in vivo and therefore is a non-natural molecule. In a further embodiment, the cDNA is then amplified, for example, by the polymerase chain reaction (PCR) or other amplification method known to those of ordinary skill in the art. The product of this amplification reaction, i.e., amplified cDNA is necessarily a non-natural product. As mentioned above, cDNA is a non-natural molecule. Second, in the case of PCR, the amplification process serves to create hundreds of millions of cDNA copies for every individual cDNA molecule of starting material. The number of copies generated are far removed from the number of copies of mRNA that are present in vivo.

In one embodiment, cDNA is amplified with primers that introduce an additional DNA sequence (adapter sequence) onto the fragments (with the use of adapter-specific primers). Amplification therefore serves to create non-natural double stranded molecules from the non-natural single stranded cDNA, by introducing barcode, adapter and/or reporter sequences onto the already non-natural cDNA. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature and (iv) the chemical addition of a detectable label to the cDNA molecules.

In one embodiment, the synthesized cDNA (for example, amplified cDNA) is immobilized on a solid surface via hybridization with a probe, e.g., via a microarray. In another embodiment, cDNA products are detected via real-time polymerase chain reaction (PCR) via the introduction of fluorescent probes that hybridize with the cDNA products. For example, in one embodiment, biomarker detection is assessed by quantitative fluorogenic RT-PCR (e.g., with TaqMan® probes). For PCR analysis, well known methods are available in the art for the determination of primer sequences for use in the analysis.

Biomarkers provided herein in one embodiment, are detected via a hybridization reaction that employs a capture probe and/or a reporter probe. For example, the hybridization probe is a probe derivatized to a solid surface such as a bead, glass or silicon substrate. In another embodiment, the capture probe is present in solution and mixed with the patient's sample, followed by attachment of the hybridization product to a surface, e.g., via a biotin-avidin interaction (e.g., where biotin is a part of the capture probe and avidin is on the surface). The hybridization assay in one embodiment, employs both a capture probe and a reporter probe. The reporter probe can hybridize to either the capture probe or the biomarker nucleic acid. Reporter probes e.g., are then counted and detected to determine the level of biomarker(s) in the sample. The capture and/or reporter probe, in one embodiment contain a detectable label, and/or a group that allows functionalization to a surface.

For example, the nCounter gene analysis system (see, e.g., Geiss et al. (2008) Nat. Biotechnol. 26, pp. 317-325, incorporated by reference in its entirety for all purposes, is amenable for use with the methods provided herein.

Hybridization assays described in U.S. Pat. Nos. 7,473,767 and 8,492,094, the disclosures of which are incorporated by reference in their entireties for all purposes, are amenable for use with the methods provided herein, i.e., to detect the biomarkers and biomarker combinations described herein.

Biomarker levels may be monitored using a membrane blot (such as used in hybridization analysis such as Northern, Southern, dot, and the like), or microwells, sample tubes, gels, beads, or fibers (or any solid support comprising bound nucleic acids). See, for example, U.S. Pat. Nos. 5,770,722, 5,874,219, 5,744,305, 5,677,195 and 5,445,934, each incorporated by reference in their entireties.

In one embodiment, microarrays are used to detect biomarker levels. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316, each incorporated by reference in their entireties. High-density oligonucleotide arrays are particularly useful for determining the biomarker profile for a large number of RNAs in a sample.

Techniques for the synthesis of these arrays using mechanical synthesis methods are described in, for example, U.S. Pat. No. 5,384,261. Although a planar array surface is generally used, the array can be fabricated on a surface of virtually any shape or even a multiplicity of surfaces. Arrays can be nucleic acids (or peptides) on beads, gels, polymeric surfaces, fibers (such as fiber optics), glass, or any other appropriate substrate. See, for example, U.S. Pat. Nos. 5,770,358, 5,789,162, 5,708,153, 6,040,193 and 5,800,992, each incorporated by reference in their entireties. Arrays can be packaged in such a manner as to allow for diagnostics or other manipulation of an all-inclusive device. See, for example, U.S. Pat. Nos. 5,856,174 and 5,922,591, each incorporated by reference in their entireties.

Serial analysis of gene expression (SAGE) in one embodiment is employed in the methods described herein. SAGE is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. See, Velculescu et al. Science 270:484-87, 1995; Cell 88:243-51, 1997, incorporated by reference in its entirety.

An additional method of biomarker level analysis at the nucleic acid level is the use of a sequencing method, for example, RNAseq, next generation sequencing, and massively parallel signature sequencing (MPSS), as described by Brenner et al. (Nat. Biotech. 18:630-34, 2000, incorporated by reference in its entirety). This is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3.0 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

Immunohistochemistry methods are also suitable for detecting the levels of the biomarkers of the present invention. Samples can be frozen for later preparation or immediately placed in a fixative solution. Tissue samples can be fixed by treatment with a reagent, such as formalin, gluteraldehyde, methanol, or the like and embedded in paraffin. Methods for preparing slides for immunohistochemical analysis from formalin-fixed, paraffin-embedded tissue samples are well known in the art.

In one embodiment, the levels of the biomarkers of Table 1A, Table 1B, Table 1C, Table 2, Table 3, Table 4, Table 5 or Table 6 (or subsets thereof, for example 5 to 20, 5 to 30, 5 to 40 biomarkers), are normalized against the expression levels of all RNA transcripts or their non-natural cDNA expression products, or protein products in the sample, or of a reference set of RNA transcripts or a reference set of their non-natural cDNA expression products, or a reference set of their protein products in the sample.

As provided throughout, the methods set forth herein provide a method for determining the lung cancer subtype of a patient. Once the biomarker levels are determined, for example by measuring non natural cDNA biomarker levels or non-natural mRNA-cDNA biomarker complexes, the biomarker levels are compared to reference values or a reference sample, for example with the use of statistical methods or direct comparison of detected levels, to make a determination of the lung cancer molecular subtype. Based on the comparison, the patient's lung cancer sample is classified, e.g., as neuroendocrine, squamous cell carcinoma, adenocarcinoma. In another embodiment, based on the comparison, the patient's lung cancer sample is classified as squamous cell carcinoma, adenocarcinoma or small cell carcinoma. In another embodiment, based on the comparison, the patient's lung cancer sample is classified as squamous cell carcinoma, adenocarcinoma, small cell carcinoma or carcinoid lung cancer.

In one embodiment, hybridization values of the at least five classifier biomarkers of Table 1A, Table 1B, Table 1C, Table 2, Table 3, Table 4, Table 5 or Table 6 are compared to reference hybridization value(s) from at least one sample training set, wherein the at least one sample training set comprises hybridization values from a reference sample(s). In a further embodiment, the at least one sample training set comprises hybridization values of the at least five classifier biomarkers of Table 1A, Table 1B, Table 1C, Table 2, Table 3, Table 4, Table 5 or Table 6 from an adenocarcinoma sample, a squamous cell carcinoma sample, a neuroendocrine sample, a small cell lung carcinoma sample, a carcinoid lung cancer sample, or a combination thereof. In another embodiment, the at least one sample training set comprises hybridization values of at least five classifier biomarkers of Table 1A, Table 1B, Table 1C, Table 2, Table 3, Table 4, Table 5, Table 6 from the reference samples provided in Table A below.

TABLE A

Various sample training set embodiments of the invention

| At least one sample training set | Origin of reference sample hybridization values | Lung cancer subtyping method |
|---|---|---|
| Embodiment 1 | Adenocarcinoma reference sample and/or squamous cell carcinoma reference sample | Assessing whether patient sample is adenocarcinoma or squamous cell carcinoma |
| Embodiment 2 | Adenocarcinoma reference sample, squamous cell carcinoma reference sample and/or neuroendocrine reference sample | Assessing whether patient sample is adenocarcinoma, squamous cell carcinoma or neuroendocrine sample |
| Embodiment 3 | Adenocarcinoma reference sample, squamous cell carcinoma reference sample, small cell carcinoma reference and/or carcinoid reference sample | Assessing whether patient sample is adenocarcinoma, squamous cell carcinoma, small cell carcinoma sample or carcinoid |

Methods for comparing detected levels of biomarkers to reference values and/or reference samples are provided herein. Based on this comparison, in one embodiment a correlation between the biomarker levels obtained from the subject's sample and the reference values is obtained. An assessment of the lung cancer subtype is then made.

Various statistical methods can be used to aid in the comparison of the biomarker levels obtained from the patient and reference biomarker levels, for example, from at least one sample training set.

In one embodiment, a supervised pattern recognition method is employed. Examples of supervised pattern recognition methods can include, but are not limited to, the nearest centroid methods (Dabney (2005) Bioinformatics 21(22):4148-4154 and Tibshirani et al. (2002) Proc. Natl. Acad. Sci. USA 99(10):6576-6572); soft independent modeling of class analysis (SIMCA) (see, for example, Wold, 1976); partial least squares analysis (PLS) (see, for example, Wold, 1966; Joreskog, 1982; Frank, 1984; Bro, R., 1997); linear descriminant analysis (LDA) (see, for example, Nillson, 1965); K-nearest neighbour analysis (KNN) (sec, for example, Brown et al., 1996); artificial neural networks (ANN) (see, for example, Wasserman, 1989; Anker et al., 1992; Hare, 1994); probabilistic neural networks (PNNs) (see, for example, Parzen, 1962; Bishop, 1995; Speckt, 1990; Broomhead et al., 1988; Patterson, 1996); rule induction (RI) (see, for example, Quinlan, 1986); and, Bayesian methods (see, for example, Bretthorst, 1990a, 1990b, 1988). In one embodiment, the classifier for identifying tumor subtypes based on gene expression data is the centroid based method described in Mullins et al. (2007) Clin Chem. 53(7):1273-9, each of which is herein incorporated by reference in its entirety.

In other embodiments, an unsupervised training approach is employed, and therefore, no training set is used.

Referring to sample training sets for supervised learning approaches again, in some embodiments, a sample training set(s) can include expression data of all of the classifier biomarkers (e.g., all the classifier biomarkers of any of Table 1A, Table 1B, Table 1C, Table 2, Table 3, Table 4, Table 5, Table 6) from an adenocarcinoma sample. In some embodiments, a sample training set(s) can include expression data of all of the classifier biomarkers (e.g., all the classifier biomarkers of any of Table 1A, Table 1B, Table 1C, Table 2, Table 3, Table 4, Table 5, Table 6) from a squamous cell carcinoma sample, an adenocarcinoma sample and/or a neuroendocrine sample. In some embodiments, the sample training set(s) are normalized to remove sample-to-sample variation.

In some embodiments, comparing can include applying a statistical algorithm, such as, for example, any suitable multivariate statistical analysis model, which can be parametric or non-parametric. In some embodiments, applying the statistical algorithm can include determining a correlation between the expression data obtained from the human lung tissue sample and the expression data from the adenocarcinoma and squamous cell carcinoma training set(s). In some embodiments, cross-validation is performed, such as (for example), leave-one-out cross-validation (LOOCV). In some embodiments, integrative correlation is performed. In some embodiments, a Spearman correlation is performed. In some embodiments, a centroid based method is employed for the statistical algorithm as described in Mullins et al. (2007) Clin Chem. 53(7):1273-9, and based on gene expression data, which is herein incorporated by reference in its entirety.

Results of the gene expression performed on a sample from a subject (test sample) may be compared to a biological sample(s) or data derived from a biological sample(s) that is known or suspected to be normal ("reference sample" or "normal sample", e.g., non-adenocarcinoma sample). In another embodiment, a reference sample or reference biomarker level data is obtained or derived from an individual known to have a lung cancer subtype, e.g., adenocarcinoma, squamous cell carcinoma, neuroendocrine, small cell carcinoma and/or carcinoid.

The reference sample may be assayed at the same time, or at a different time from the test sample. Alternatively, the biomarker level information from a reference sample may be stored in a database or other means for access at a later date.

The biomarker level results of an assay on the test sample may be compared to the results of the same assay on a reference sample. In some cases, the results of the assay on the reference sample are from a database, or a reference value(s). In some cases, the results of the assay on the reference sample are a known or generally accepted value or range of values by those skilled in the art. In some cases the comparison is qualitative. In other cases the comparison is quantitative. In some cases, qualitative or quantitative comparisons may involve but are not limited to one or more of the following: comparing fluorescence values, spot intensities, absorbance values, chemiluminescent signals, histograms, critical threshold values, statistical significance values, expression levels of the genes described herein, mRNA copy numbers.

In one embodiment, an odds ratio (OR) is calculated for each biomarker level panel measurement. Here, the OR is a measure of association between the measured biomarker values for the patient and an outcome, e.g., lung cancer subtype. For example, see, *J. Can. Acad. Child Adolesc. Psychiatry* 2010; 19(3): 227-229, which is incorporated by reference in its entirety for all purposes.

In one embodiment, a specified statistical confidence level may be determined in order to provide a confidence level regarding the lung cancer subtype. For example, it may be determined that a confidence level of greater than 90% may be a useful predictor of the lung cancer subtype. In other embodiments, more or less stringent confidence levels may be chosen. For example, a confidence level of about or at least about 50%, 60%, 70%, 75%, 80%, 85%, 90%, 95%, 97.5%, 99%, 99.5%, or 99.9% may be chosen. The confidence level provided may in some cases be related to the quality of the sample, the quality of the data, the quality of the analysis, the specific methods used, and/or the number of gene expression values (i.e., the number of genes) analyzed. The specified confidence level for providing the likelihood of response may be chosen on the basis of the expected number of false positives or false negatives. Methods for choosing parameters for achieving a specified confidence level or for identifying markers with diagnostic power include but are not limited to Receiver Operating Characteristic (ROC) curve analysis, binormal ROC, principal component analysis, odds ratio analysis, partial least squares analysis, singular value decomposition, least absolute shrinkage and selection operator analysis, least angle regression, and the threshold gradient directed regularization method.

Determining the lung cancer subtype in some cases be improved through the application of algorithms designed to normalize and or improve the reliability of the biomarker level data. In some embodiments of the present invention, the data analysis utilizes a computer or other device, machine or apparatus for application of the various algorithms described herein due to the large number of individual data points that are processed. A "machine learning algorithm" refers to a computational-based prediction methodology, also known to persons skilled in the art as a "classifier," employed for characterizing a biomarker level profile or profiles, e.g., to determine the lung cancer subtype. The biomarker levels, determined by, e.g., microarray-based hybridization assays, sequencing assays, NanoString assays, etc., are in one embodiment subjected to the algorithm in order to classify the profile. Supervised learning generally involves "training" a classifier to recognize the distinctions among classes (e.g., adenocarcinoma positive, adenocarcinoma negative, squamous positive, squamous negative, neuroendocrine positive, neuroendocrine negative, small cell positive, small cell negative, carcinoid positive, carcinoid negative), and then "testing" the accuracy of the classifier on an independent test set. For new, unknown samples the classifier can be used to predict, for example, the class (e.g., (i) adenocarcinoma vs. squamous cell carcinoma vs. neuroendocrine or (ii) adenocarcinoma vs. squamous cell carcinoma vs. small cell vs. carcinoid, etc.) in which a particular sample or samples belongs.

In some embodiments, a robust multi-array average (RMA) method may be used to normalize raw data. The RMA method begins by computing background-corrected intensities for each matched cell on a number of microarrays. In one embodiment, the background corrected values are restricted to positive values as described by Irizarry et al. (2003). Biostatistics April 4 (2): 249-64, incorporated by reference in its entirety for all purposes. After background correction, the base-2 logarithm of each background corrected matched-cell intensity is then obtained. The background corrected, log-transformed, matched intensity on each microarray is then normalized using the quantile normalization method in which for each input array and each probe value, the array percentile probe value is replaced with the average of all array percentile points, this method is more completely described by Bolstad et al. Bioinformatics 2003, incorporated by reference in its entirety. Following quantile normalization, the normalized data may then be fit to a linear model to obtain an intensity measure for each probe on each microarray. Tukey's median polish algorithm (Tukey, J. W., Exploratory Data Analysis. 1977, incorporated by reference in its entirety for all purposes) may then be used to determine the log-scale intensity level for the normalized probe set data.

Various other software programs may be implemented. In certain methods, feature selection and model estimation may be performed by logistic regression with lasso penalty using glmnet (Friedman et al. (2010). *Journal of statistical software* 33(1): 1-22, incorporated by reference in its entirety). Raw reads may be aligned using TopHat (Trapnell et al. (2009). *Bioinformatics* 25(9): 1105-11, incorporated by reference in its entirety). In methods, top features (N ranging from 10 to 200) are used to train a linear support vector machine (SVM) (Suykens J A K, Vandewalle J. Least Squares Support Vector Machine Classifiers. *Neural Processing Letters* 1999; 9(3): 293-300, incorporated by reference in its entirety) using the e1071 library (Meyer D. Support vector machines: the interface to libsvm in package e1071. 2014, incorporated by reference in its entirety). Confidence intervals, in one embodiment, are computed using the pROC package (Robin X, Turck N, Hainard A, et al. pROC: an open-source package for R and S+ to analyze and compare ROC curves. *BMC bioinformatics* 2011; 12: 77, incorporated by reference in its entirety).

In addition, data may be filtered to remove data that may be considered suspect. In one embodiment, data derived from microarray probes that have fewer than about 4, 5, 6, 7 or 8 guanosine+cytosine nucleotides may be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine+cytosine nucleotides may in one embodiment be considered unreliable due to their aberrant hybridization propensity or secondary structure issues.

In some embodiments of the present invention, data from probe-sets may be excluded from analysis if they are not identified at a detectable level (above background).

In some embodiments of the present disclosure, probe-sets that exhibit no, or low variance may be excluded from further analysis. Low-variance probe-sets are excluded from the analysis via a Chi-Square test. In one embodiment, a probe-set is considered to be low-variance if its transformed variance is to the left of the 99 percent confidence interval of the Chi-Squared distribution with (N−1) degrees of freedom. (N−1)*Probe-set Variance/(Gene Probe-set Variance). about.Chi-Sq(N−1) where N is the number of input CEL files, (N−1) is the degrees of freedom for the Chi-Squared distribution, and the "probe-set variance for the gene" is the average of probe-set variances across the gene. In some embodiments of the present invention, probe-sets for a given mRNA or group of mRNAs may be excluded from further analysis if they contain less than a minimum number of probes that pass through the previously described filter steps for GC content, reliability, variance and the like. For example in some embodiments, probe-sets for a given gene or transcript cluster may be excluded from further analysis if they contain less than about 1, 2, 3, 4, 5, 6, 7, 8, 9, 10, 11, 12, 13, 14, 15, or less than about 20 probes.

Methods of biomarker level data analysis, in one embodiment, further include the use of a feature selection algorithm as provided herein. In some embodiments of the present invention, feature selection is provided by use of the LIMMA software package (Smyth, G. K. (2005). Limma: linear models for microarray data. In: Bioinformatics and Computational Biology Solutions using R and Bioconductor, R. Gentleman, V. Carey, S. Dudoit, R. Irizarry, W. Huber (eds.), Springer, New York, pages 397-420, incorporated by reference in its entirety for all purposes).

Methods of biomarker level data analysis, in one embodiment, include the use of a pre-classifier algorithm. For example, an algorithm may use a specific molecular fingerprint to pre-classify the samples according to their composition and then apply a correction/normalization factor. This data/information may then be fed in to a final classification algorithm which would incorporate that information to aid in the final diagnosis.

Methods of biomarker level data analysis, in one embodiment, further include the use of a classifier algorithm as provided herein. In one embodiment of the present invention, a diagonal linear discriminant analysis, k-nearest neighbor algorithm, support vector machine (SVM) algorithm, linear support vector machine, random forest algorithm, or a probabilistic model-based method or a combination thereof is provided for classification of microarray data. In some embodiments, identified markers that distinguish samples (e.g., of varying biomarker level profiles, of varying lung cancer subtypes, and/or varying molecular subtypes of adenocarcinoma are selected based on statistical significance of the difference in biomarker levels between classes of interest. In some cases, the statistical significance is adjusted by applying a Benjamin Hochberg or another correction for false discovery rate (FDR).

In some cases, the classifier algorithm may be supplemented with a meta-analysis approach such as that described by Fishel and Kaufman et al. 2007 Bioinformatics 23(13): 1599-606, incorporated by reference in its entirety for all purposes. In some cases, the classifier algorithm may be supplemented with a meta-analysis approach such as a repeatability analysis.

Methods for deriving and applying posterior probabilities to the analysis of biomarker level data are known in the art and have been described for example in Smyth, G. K. 2004 *Stat. Appi. Genet. Mol. Biol.* 3: Article 3, incorporated by reference in its entirety for all purposes. In some cases, the posterior probabilities may be used in the methods of the present invention to rank the markers provided by the classifier algorithm.

A statistical evaluation of the results of the biomarker level profiling may provide a quantitative value or values indicative of the lung cancer subtype (e.g., adenocarcinoma, squamous cell carcinoma, neuroendocrine, small cell, carcinoid). In one embodiment, the data is presented directly to the physician in its most useful form to guide patient care, or is used to define patient populations in clinical trials or a patient population for a given medication. The results of the molecular profiling can be statistically evaluated using a number of methods known to the art including, but not limited to: the students T test, the two sided T test, Pearson rank sum analysis, hidden Markov model analysis, analysis of q-q plots, principal component analysis, one way ANOVA, two way ANOVA, LIMMA and the like.

In some cases, accuracy may be determined by tracking the subject over time to determine the accuracy of the original diagnosis. In other cases, accuracy may be established in a deterministic manner or using statistical methods. For example, receiver operator characteristic (ROC) analysis may be used to determine the optimal assay parameters to achieve a specific level of accuracy, specificity, positive predictive value, negative predictive value, and/or false discovery rate.

In some cases the results of the biomarker level profiling assays, are entered into a database for access by representatives or agents of a molecular profiling business, the individual, a medical provider, or insurance provider. In some cases, assay results include sample classification, identification, or diagnosis by a representative, agent or consultant of the business, such as a medical professional. In other cases, a computer or algorithmic analysis of the data is provided automatically. In some cases the molecular profiling business may bill the individual, insurance provider, medical provider, researcher, or government entity for one or more of the following: molecular profiling assays performed, consulting services, data analysis, reporting of results, or database access.

In some embodiments of the present invention, the results of the biomarker level profiling assays are presented as a report on a computer screen or as a paper record. In some embodiments, the report may include, but is not limited to, such information as one or more of the following: the levels of biomarkers (e.g., as reported by copy number or fluorescence intensity, etc.) as compared to the reference sample or reference value(s); the lung cancer subtype, proposed therapies.

In one embodiment, the results of the classifier biomarker profiling may be classified into one or more of the following: adenocarcinoma positive, adenocarcinoma negative, squamous cell carcinoma positive, squamous cell carcinoma negative, neuroendocrine positive, neuroendocrine negative, small cell carcinoma positive, small cell carcinoma negative, carcinoid positive, carcinoid negative or a combination thereof.

In some embodiments of the present invention, results are classified using a trained algorithm. Trained algorithms of the present invention include algorithms that have been developed using a reference set of known gene expression values and/or normal samples, for example, samples from individuals diagnosed with a particular molecular subtype of adenocarcinoma. In some cases a reference set of known gene expression values are obtained from individuals who have been diagnosed with a particular molecular subtype of lung cancer.

Algorithms suitable for categorization of samples include but are not limited to k-nearest neighbor algorithms, support vector machines, linear discriminant analysis, diagonal linear discriminant analysis, updown, naive Bayesian algorithms, neural network algorithms, hidden Markov model algorithms, genetic algorithms, or any combination thereof.

When a binary classifier is compared with actual true values (e.g., values from a biological sample), there are typically four possible outcomes. If the outcome from a prediction is p (where "p" is a positive classifier output, such as the presence of a deletion or duplication syndrome) and the actual value is also p, then it is called a true positive (TP); however if the actual value is n then it is said to be a false positive (FP). Conversely, a true negative has occurred when both the prediction outcome and the actual value are n (where "n" is a negative classifier output, such as no deletion or duplication syndrome), and false negative is when the prediction outcome is n while the actual value is p. In one embodiment, consider a test that seeks to determine a molecular subtype of lung cancer. A false positive in this case occurs when the person tests for a molecular subtype that he or she does not actually have. A false negative, on the other hand, occurs when the person tests negative, suggesting the sample is not a particular lung cancer subtype, when the sample is in fact the lung cancer sample should be characterized as the particular lung cancer subtype.

The positive predictive value (PPV), or precision rate, or post-test probability of disease, is the proportion of subjects diagnosed with the correct lung cancer subtype. It reflects the probability that a positive test reflects the underlying condition being tested for. Its value does however depend on the prevalence of the disease, which may vary. In one example the following characteristics are provided: FP (false positive); TN (true negative); TP (true positive); FN (false negative). False positive rate $(\alpha)$=FP/(FP+TN)-specificity; False negative rate $(\beta)$=FN/(TP+FN)-sensitivity; Power=sensitivity=$1-\beta$; Likelihood-ratio positive=sensitivity/(1-specificity); Likelihood-ratio negative=(1-sensitivity)/specificity. The negative predictive value (NPV) is the proportion of subjects with negative test results who are correctly diagnosed.

In some embodiments, the results of the biomarker level analysis of the subject methods provide a statistical confidence level that a given diagnosis is correct. In some embodiments, such statistical confidence level is at least about, or more than about 85%, 90%, 91%, 92%, 93%, 94%, 95%, 96%, 97%, 98%, 99% 99.5%, or more.

In some embodiments, the method further includes classifying the lung tissue sample as a particular lung cancer subtype based on the comparison of biomarker levels in the sample and reference biomarker levels, for example present in at least one training set. In some embodiments, the lung tissue sample is classified as a particular subtype if the results of the comparison meet one or more criterion such as, for example, a minimum percent agreement, a value of a statistic calculated based on the percentage agreement such as (for example) a kappa statistic, a minimum correlation (e.g., Pearson's correlation) and/or the like.

It is intended that the methods described herein can be performed by software (stored in memory and/or executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including Unix utilities, C, C++, Java™, Ruby, SQL, SAS®, the R programming language/software environment, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Some embodiments described herein relate to devices with a non-transitory computer-readable medium (also can be referred to as a non-transitory processor-readable medium or memory) having instructions or computer code thereon for performing various computer-implemented operations and/or methods disclosed herein. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

In some embodiments, at least five biomarkers, from about 5 to about 20 biomarkers, from about 5 to about 50 biomarkers, from about 5 to about 40 biomarkers, or from about 5 to about 30 biomarkers (e.g., as disclosed in Table 1A, Table 1B, Table 1C, Table 2, Table 3, Table 4, Table 5 and Table 6) is capable of classifying types and/or subtypes of lung cancer with a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between. In some embodiments, any combination of biomarkers disclosed herein (e.g., in Table 1A, Table 1B, Table 1C, Table 2, Table 3, Table 4, Table 5 and Table 6 and sub-combinations thereof) can used to obtain a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between.

In some embodiments, at least five biomarkers, from about 5 to about 20 biomarkers, from about 5 to about 50 biomarkers, from about 5 to about 40 biomarkers, or from about 5 to about 30 biomarkers (e.g., as disclosed in Table 1A, Table 1B, Table 1C, Table 2, Table 3, Table 4, Table 5 and Table 6) is capable of classifying lung cancer types and/or subtypes with a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between. In some embodiments, any combination of biomarkers disclosed herein can be used to obtain a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between.

In some embodiments, one or more kits for practicing the methods of the invention are further provided. The kit can encompass any manufacture (e.g., a package or a container) including at least one reagent, e.g., an antibody, a nucleic acid probe or primer, and/or the like, for detecting the biomarker level of a classifier biomarker. The kit can be promoted, distributed, or sold as a unit for performing the methods of the present invention. Additionally, the kits can contain a package insert describing the kit and methods for its use.

In one embodiment, upon determining a patient's lung cancer subtype, the patient is selected for suitable therapy, for example chemotherapy or drug therapy with an angiogenesis inhibitor. In one embodiment, the therapy is angiogenesis inhibitor therapy, and the angiogenesis inhibitor is a vascular endothelial growth factor (VEGF) inhibitor, a VEGF receptor inhibitor, a platelet derived growth factor (PDGF) inhibitor or a PDGF receptor inhibitor.

In another embodiment, the angiogenesis inhibitor is an integrin antagonist, a selectin antagonist, an adhesion molecule antagonist (e.g., antagonist of intercellular adhesion molecule (ICAM)-1, ICAM-2, ICAM-3, platelet endothelial adhesion molecule (PCAM), vascular cell adhesion molecule (VCAM)), lymphocyte function-associated antigen 1 (LFA-1)), a basic fibroblast growth factor antagonist, a vascular endothelial growth factor (VEGF) modulator, or a platelet derived growth factor (PDGF) modulator (e.g., a PDGF antagonist).

In one embodiment, as provided above, upon determining a patient's lung cancer subtype, the patient is selected for suitable therapy, for example chemotherapy or drug therapy with an angiogenesis inhibitor. In one embodiment, the angiogenesis inhibitor is one or more of the following: interferon gamma 1β, interferon gamma 1β (Actimmune®) with pirfenidone, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with *salvia* and *Schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260, XV615, endostatin, a 20 kDa C-terminal fragment derived from type XVIII collagen, angiostatin (a 38 kDa fragment of plasmin), or a member of the thrombospondin (TSP) family of proteins. In a further embodiment, the angiogenesis inhibitor is a TSP-1, TSP-2, TSP-3, TSP-4 and TSP-5.

In one embodiment, the therapy is aa soluble VEGF receptor, e.g., soluble VEGFR-1 and neuropilin 1 (NPR1), angiopoietin-1, angiopoietin-2, vasostatin, calreticulin, platelet factor-4, a tissue inhibitor of metalloproteinase (TIMP) (e.g., TIMP1, TIMP2, TIMP3, TIMP4), cartilage-derived angiogenesis inhibitor (e.g., peptide troponin I and chrondomodulin I), a disintegrin and metalloproteinase with thrombospondin motif 1, an interferon (IFN) (e.g., IFN-α, IFN-β, IFN-γ), a chemokine, e.g., a chemokine having the C-X-C motif (e.g., CXCL10, also known as interferon gamma-induced protein 10 or small inducible cytokine B10), an interleukin cytokine (e.g., IL-4, IL-12, IL-18), prothrombin, antithrombin III fragment, prolactin, the protein encoded by the TNFSF15 gene, osteopontin, maspin, canstatin, proliferin-related protein, angiopoietin-1, angiopoietin-2, angiostatin, endostatin, vasostatin, thrombospondin, calreticulin, platelet factor-4, TIMP, CDAI, interferon α, interferon β, vascular endothelial growth factor inhibitor (VEGI) meth-1, meth-2, prolactin, VEGI, SPARC, osteopontin, maspin, canstatin, proliferin-related protein (PRP), restin, TSP-1, TSP-2, interferon gamma 1β, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with *salvia* and *Schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260, XV615 or a combination thereof.

In yet another embodiment, upon determining a patient's lung cancer subtype, the patient is selected for suitable therapy with pazopanib (Votrient), sunitinib (Sutent), sorafenib (Nexavar), axitinib (Inlyta), ponatinib (Iclusig), vandetanib (Caprelsa), cabozantinib (Cometrig), ramucirumab (Cyramza), regorafenib (Stivarga), ziv-aflibercept (Zaltrap), or a combination thereof. In yet another embodiment, upon determining a patient's lung cancer subtype, the patient is selected for suitable therapy with a VEGF inhibitor. In a further embodiment, the VEGF inhibitor is axitinib, cabozantinib, aflibercept, brivanib, tivozanib, ramucirumab or motesanib. In yet a further embodiment, the VEGF inhibitor is motesanib.

In yet another embodiment, upon determining a patient's lung cancer subtype, the patient is selected for suitable therapy with a platelet derived growth factor (PDGF) antagonist. For example, the PDGF antagonist, in one embodiment, is an anti-PDGF aptamer, an anti-PDGF antibody or fragment thereof, an anti-PDGF receptor antibody or fragment thereof, or a small molecule antagonist. In one embodiment, the PDGF antagonist is an antagonist of the PDGFR-α or PDGFR-β. In one embodiment, the PDGF antagonist is the anti-PDGF-β aptamer E10030, sunitinib, axitinib, sorefenib, imatinib, imatinib mesylate, nintedanib, pazopanib HCl, ponatinib, MK-2461, dovitinib, pazopanib, crenolanib, PP-121, telatinib, imatinib, KRN 633, CP 673451, TSU-68, Ki8751, amuvatinib, tivozanib, masitinib, motesanib diphosphate, dovitinib dilactic acid, linifanib (ABT-869).

EXAMPLES

The present invention is further illustrated by reference to the following Examples. However, it should be noted that these Examples, like the embodiments described above, is illustrative and is not to be construed as restricting the scope of the invention in any way.

Methods

Several publically available lung cancer gene expression data sets including 2,168 lung cancer samples (TCGA, NCI, UNC, Duke, Expo, Seoul, Tokyo, and France) were assembled to validate a 57 gene expression Lung Subtype Panel (LSP) developed to complement morphologic classification of lung tumors. LSP included 52 lung tumor classifying genes plus 5 housekeeping genes. Data sets with both gene expression data and lung tumor morphologic classification were selected. Three categories of genomic data were represented in the data sets: Affymetrix U133+2(n=883) (also referred to as "A-833"), Agilent 44K(n=334) (also referred to as "A-334"), and Illumina RNAseq(n=951) (also referred to as "I-951"). Data sources are provided in Table 7 and normalization methods in Table 8. Samples with a definitive diagnosis of adenocarcinoma, carcinoid, small cell, and squamous cell carcinoma were used in the analysis.

TABLE 7

Data sources for publicly available lung cancer gene expression data

| Source | Platform(s) | N | Subtype | Ref |
|---|---|---|---|---|
| TCGA[1] | RNASeq (LUAD) | 528 | adenocarcinomas | TCGA-DCC |
| TCGA[2] | RNASeq (LUSC) | 534 | Squamous | TCGA-DCC |
| UNC[3] | Agilent_44K | 56 | 56 squamous | CCR (2010) PMID: 20643781 |
| UNC[4] | Agilent_44K | 116 | 116 adenocarcinomas | PLoS One (2012) PMID: 22590557 |
| NCI[5] | Agilent_44K | 172 | 56 adenocarcinoma, 92 squamous, 10 large cell | CCR (2009) |
| Korea[6] | HG-U133 + 2 | 138 | 63 adenocarcinoma, 75 squamous | CCR (2008) PMID: 19010856 |
| Expo[7] | HG-U133 + 2 | 130 | all histology subtypes | GSE2109 |
| French[8] | HG-U133 + 2 | 307 | all histology subtypes | Sci Transl Med (2013) PMID: 23698379 |
| Duke[9] | HG-U133 + 2 | 118 | adenocarcinoma and squamous | Nature (2006) PMID: 16273092 |
| Tokyo[10] | HG-U133 + 2 | 246 | adenocarcinomas | PLoS One (2012) PMID: 22080568, 23028479 |

[1]https://tcga-data.nci.nih.gov/tcgafiles/ftp_auth/distro_ftpusers/anonymous/tumor/luad/cgcc/unc.edu/illuminahiseq_rnaseqv2/rnaseqv2/?C=S;O=A
[2]https://tcga-data.nci.nih.gov/tcgafiles/ftp_auth/distro_ftpusers/anonymous/tumor/lusc/cgcc/unc.edu/illuminahiseq_rnaseqv2/rnaseqv2/
[3]http://www.ncbi.nlm.nih.gov/geo/query/acc.cgi?acc=GSE17710
[4]http://www.ncbi.nlm.nih.gov/geo/query/acc.cgi?acc=GSE26939
[5]http://research.agendia.com/
[6]http://www.ncbi.nlm.nih.gov/geo/query/acc.cgi?acc=GSE8894
[7]http://www.ncbi.nlm.nih.gov/geo/query/acc.cgi?acc=GSE2109
[8]http://www.ncbi.nlm.nih.gov/geo/query/acc.cgi?acc=GSE30219
[9]http://www.ncbi.nlm.nih.gov/geo/query/acc.cgi?acc=GSE3141
[10]http://www.ncbi.nlm.nih.gov/geo/query/acc.cgi?acc=GSE31210

TABLE 8

Normalization methods used for the 3 public gene expression datasets

| Source | Platforms | Data Preprocessing/Normalization |
|---|---|---|
| TCGA | RNASeq | RSEM expression estimates are normalized to set the upper quartile count at 1000 for gene level, 2 based log transformed, data matrix is row (gene) median centered, column (sample) standardized. |
| UNC + NKI | Agilent_ 44K | 2 based log ratio of the two channel intensities are LOWESS normalized, data matrix is row (gene) median centered, column (sample) standardized. |
| Affy | HG-U133 + 2 | MAS5 normalized one channel intensities are 2 based log transformed, data matrix is row (gene) median centered, column (sample) standardized. |

The A-833 dataset was used as training for calculation of adenocarcinoma, carcinoid, small cell carcinoma, and squamous cell carcinoma gene centroids according to methods described previously. Gene centroids trained on the A-833 data were then applied to the normalized TCGA and A-334 datasets to investigate LSP's ability to classify lung tumors using publicly available gene expression data. For the application of A-833 training centroids to the A-833 dataset, evaluation was performed using Leave One Out (LOO) cross validation. Spearman correlations were calculated for tumor sample gene expression results to the A-833 gene expression training centroids. Tumors were assigned a genomic-defined histologic type (carcinoid, small cell, adenocarcinoma and squamous cell carcinoma) corresponding to the maximally correlated centroids. A 2 class, 3 class, and 4 class prediction was explored. Correct predictions were defined as LSP calls matching the tumor's histologic diagnosis. Percent agreement was defined as the number of correct predictions divided by the number of all predictions and an agreement kappa statistic was calculated.

Ten lung tumor RNA expression datasets were combined into three platform specific data sets (A-833, A-334, and I-951). The patient population was diverse and included smokers and nonsmokers with tumors ranging from Stage 1-Stage IV. Sample characteristics and lung cancer diagnoses of the three datasets are included in Table 9.

TABLE 9

Sample Characteristics

| Characteristic | TCGA RNA seq | Agilent | Affymetrix |
|---|---|---|---|
| Total # of samples | 1062 | 334 | 875 |
| Tumor Specimen histology | | | |
| Adenocarcinoma | 468 | 174 | 490 |
| Carcinoid | 0 | 0 | 23 |
| Neuroendocrine (NOS) | 0 | 0 | 6 |
| Squamous cell carcinoma | 483 | 148 | 227 |
| Other (excluded from analysis) | 111 | 12 | 105 |
| Gender | | | |
| Female/Male/NA | 285/366/300 | 87/85/150 | 272/491/7 |
| Age at diagnosis | | | |
| Median/(Range) | 67/(38-88) | 66/(37-90) | 63/(13-85) |
| Age not available | 323 | 150 | 7 |
| Stage | | | |
| I | 355 | NA | NA |
| II | 146 | NA | NA |
| III | 119 | NA | NA |
| IV | 26 | NA | NA |
| Stage not available | 305 | 322 | 770 |
| Smoking | | | |
| Smoker | 386 | NA | NA |
| Non-smoker | 39 | NA | NA |
| Smoking status not available | 526 | 322 | 770 |

Predicted tumor type for a 2 class, 3 class, and 4 class predictor were compared with tumor morphologic classification and percent agreement and Fleiss' kappa was calculated for each predictor (Tables 10a, 10b and 10c).

TABLE 10a

A-833 dataset training gene centroids applied to 2 other publicly available lung cancer gene expression databases (TCGA & A-334) for a 2 class prediction of lung tumor type. LOO cross validation was performed for the A-833 dataset.

| Histology Diagnosis | Prediction | | | | | | | | |
|---|---|---|---|---|---|---|---|---|---|
| | TCGA RNAseq | | | Agilent | | | Affymetrix LOO | | |
| | AD | SQ | Sum | AD | SQ | Sum | AD | SQ | Sum |
| Adenocarcinoma (AD) | 452 | 16 | 468 | 151 | 23 | 174 | 423 | 67 | 490 |
| Squamous cell carcinoma (SQ) | 37 | 446 | 483 | 39 | 109 | 148 | 41 | 186 | 227 |
| Sum | 489 | 462 | 951 | 190 | 132 | 322 | 464 | 253 | 717 |
| % Agreement | | 94% | | | 81% | | | 85% | |
| kappa | | 0.89 | | | 0.61 | | | 0.66 | |

TABLE 10b

A-833 dataset training gene centroids applied to data from 2 other publicly available lung cancer gene expression databases (TCGA & A-334) for a 3 class prediction of lung tumor type. LOO cross validation was performed for the A-833 dataset.

| Histology Diagnosis | Prediction | | | | | | | | | | | |
|---|---|---|---|---|---|---|---|---|---|---|---|---|
| | TCGA RNAseq | | | | Agilent | | | | Affymetrix LOO | | | |
| | AD | NE | SQ | Sum | AD | NE | SQ | Sum | AD | NE | SQ | Sum |
| Adenocarcinoma (AD) | 419 | 29 | 29 | 468 | 141 | 6 | 27 | 174 | 399 | 3 | 88 | 490 |
| Neuroendocrine (NE) | NA | NA | NA | NA | NA | NA | NA | NA | 2 | 49 | 2 | 53 |
| Squamous cell carcinoma (SQ) | 23 | 15 | 445 | 483 | 28 | 3 | 117 | 148 | 25 | 7 | 195 | 227 |
| Sum | 442 | 44 | 465 | 951 | 169 | 9 | 144 | 322 | 426 | 59 | 285 | 770 |
| % Agreement | | 91% | | | | 80% | | | | 84% | | |
| kappa | | 0.82 | | | | 0.61 | | | | 0.69 | | |

TABLE 10c

A-833 dataset training gene centroids applied to data from 2 other publicly available lung cancer gene expression databases (TCGA & A-334) for a 4 class prediction of lung tumor type. L00 cross validation was performed for the A-833 dataset.

| Histology Diagnosis | Prediction | | | | | | | | | | | | | | |
|---|---|---|---|---|---|---|---|---|---|---|---|---|---|---|---|
| | TCGA RNAseq | | | | | Agilent | | | | | Affymetrix LOO | | | | |
| | AD | CA | SC | SQ | Sum | AD | CA | SC | SQ | Sum | AD | CA | SC | SQ | Sum |
| Adenocarcinoma (AD) | 428 | 2 | 20 | 18 | 468 | 138 | 2 | 5 | 29 | 174 | 389 | 1 | 3 | 97 | 490 |
| Carcinoid (CA) | NA | NA | NA | NA | NA | NA | NA | NA | NA | NA | 1 | 22 | 0 | 0 | 23 |
| Small cell (SC) | NA | NA | NA | NA | NA | NA | NA | NA | NA | NA | 27 | 1 | 5 | 194 | 227 |
| Squamous cell carcinoma (SQ) | 23 | 2 | 15 | 443 | 483 | 27 | 0 | 3 | 118 | 148 | 27 | 1 | 5 | 194 | 227 |
| Sum | 451 | 4 | 35 | 461 | 951 | 165 | 2 | 8 | 147 | 322 | 418 | 25 | 28 | 293 | 764 |
| % Agreement | | | 92% | | | | | 80% | | | | | 82% | | |
| kappa | | | 0.84 | | | | | 0.60 | | | | | 0.65 | | |

Evaluation of inter-observer reproducibility of lung cancer diagnosis based on morphologic classification alone has previously been published. Overall inter-observer agreement improved with simplification of the typing scheme. Using the comprehensive 2004 World Health Organization classification system inter-observer agreement was low (k=0.25). Agreement improved with simplification of the diagnosis to the therapeutically relevant 2 type differentiation of squamous/non-squamous (k=0.55). Agreement of inter-observer diagnosis is compared to agreement of 2, 3 and 4 class LSP diagnosis in this validation study (Table 11).

TABLE 11

Inter-observer agreement (3) measured using kappa statistic and LSP agreement with histologic diagnosis in multiple gene expression datasets.

| Agreement | WHO 2004 Classification Inter-observer agreement | 2 class squamous/ nonsquamous cell carcinoma Inter-observer agreement | 3 class LSP agreement w/Hist Dx | 4 class LSP agreement w/Hist Dx | LSP agreement w/Hist Dx |
|---|---|---|---|---|---|
| Kappa | 0.25 | 0.55 | 0.61-0.89 | 0.61-0.82 | 0.60-0.84 |

Differentiation among various morphologic subtypes of lung cancer is increasingly important as therapeutic development and patient management become more specifically targeted to unique features of each tumor. Histologic diagnosis can be challenging and several studies have demonstrated limited reproducibility of morphologic diagnoses. The addition of several immunohistochemistry markers, such as p63 and TTF-1 improves diagnostic precision but many lung cancer biopsies are limited in size and/or cellularity precluding full characterization using multiple IHC markers. Agreement was markedly better for all the classifiers (2, 3, and 4 type) in the TCGA RNAseq dataset (% agreement range 91%-94%) as compared to the other datasets possibly due to the greater accuracy of the histologic diagnosis and/or the greater precision of the RNA expression results. Despite several limitations described below, this study demonstrates that LSP, can be a valuable adjunct to histology in typing lung tumors.

In multiple datasets with hundreds of lung cancer samples, molecular profiling using the Lung Subtype Panel (LSP) compared favorably to light microscopic derived diagnoses, and showed a higher level of agreement than pathologist reassessments. RNA-based tumor subtyping can provide valuable information in the clinic, especially when tissue is limiting and the morphologic diagnosis remains unclear.

The disclosures of the following references are incorporated herein by reference in their entireties for all purposes:
a. American Cancer Society. Cancer Facts and Figures, 2014.
b. National Comprehensive Cancer Network (NCCN) Clinical Practice Guideline in Oncology. Non-Small Cell Lung Cancer. Version 2.2013.
c. Grilley Olson J E, Hayes D N, Moore D T, et al. Arch Pathol Lab Med 2013; 137: 32-40
d. Thunnissen E, Boers E, Heideman D A, et al. Virchows Arch 2012; 461:629-38.
e. Wilkerson M D, Schallheim J M, Hayes D N, et al. J Molec Diagn 2013; 15:485-497.
f. Li B, Dewey C N. BMC Bioinformatics 2011, 12:323 doi:10.1186/1471-2105-12-323
g. Yang Y H, Dudoit S, Luu P, et al. Nucleic Acids Research 2002, 30:e15.
h. Hubbell E, Liu, W, Mei R. Bioinformatics (2002) 18 (12): 1585-1592. doi:10.1093/bioinformatics/18.12.1585.
i. Travis W D, Brambilla E, Muller-Hermelink H K, Harris C C. Pathology and Genetics of Tumors of the Lung, Pleura, Thymus, and Heart. 3rd ed. Lyon, France: IARC Press; 2004. World Health Organization Classification of Tumors: vol 10.
j. Travis W D and Rekhtman N. Sem Resp and Crit Care Med 2011; 32(1): 22-31.

Example 2—Lung Cancer Subtyping of Multiple Fresh Frozen and Formalin Fixed Paraffin Embedded Lung Tumor Gene Expression Datasets Multiple datasets comprising 2,177 samples were assembled to evaluate a Lung Subtype Panel (LSP) gene expression classifier. The datasets included several publically available lung cancer gene expression data sets, including 2,099 Fresh Frozen lung cancer samples (TCGA, NCI, UNC, Duke, Expo, Seoul, and France) as well as newly collected gene expression data from 78 FFPE samples. Data sources are provided in the Table 12 below. The 78 FFPE samples were archived residual lung tumor samples collected at the University of North Carolina at Chapel Hill (UNC-CH) using an IRB approved protocol. Only samples with a definitive diagnosis of AD, carcinoid, Small Cell Carcinoma (SCC), or SQC were used in the analysis. A total of 4 categories of genomic data were available for analysis: Affymetrix U133+2 (n=693), Agilent 44K (n=344), Illumina® RNAseq (n=1,062) and newly collected qRT-PCR (n=78) data.

Archived FFPE lung tumor samples (n=78) were analyzed using a qRT-PCR gene expression assay as previously described (Wilkerson et al. J Molec Diagn 2013; 15:485-497, incorporated by reference herein in its entirety for all purposes) with the following modifications. RNA was extracted from one 10 μm section of FFPE tissue using the High Pure RNA Paraffin Kit (Roche Applied Science, Indianapolis, Ind.). Extracted RNA was diluted to 5 ng/μL and first strand cDNA was synthesized using gene specific 3' primers in combination with random hexamers (Superscript III®, Invitrogen®, Thermo Fisher Scientific Corp, Waltham, Mass.). An ABI 7900 (Applied Biosystems, Thermo Fisher Scientific Corp, Waltham, Mass.) was used for qRT-PCR with continuous SYBR green fluorescence (530 nm) monitoring. ABI 7900 quantitation software generated amplification curves and associated threshold cycle (Ct) values. Original clinical diagnoses gathered with the samples is in Table 13.

TABLE 12

| Source | Platforms | N | Subtype | Normalization Method Used | Data Source |
|---|---|---|---|---|---|
| TCGA | RNASeq (LUAD) | 528 | adenocarcinomas | RSEM expression estimates are normalized to set the upper quartile count at 1000 for | Ref 16 TCGA |

TABLE 12-continued

| Source | Platforms | N | Subtype | Normalization Method Used | Data Source |
|---|---|---|---|---|---|
| TCGA | RNASeq (LUSC) | 534 | squamous cell carcinoma | gene level, 2 based log transformed, data matrix is row (gene) median centered, column (sample) standardized.[28] | Ref 15 TCGA |
| UNC | Agilent_44K | 56 | squamous cell carcinoma | 2 based log ratio of the two channel intensities are LOWESS normalized, data matrix is row (gene) median centered, column (sample) standardized.[29] | Ref 19 GSE17710 |
| UNC | Agilent_44K | 116 | adenocarcinomas | | Ref 20 GSE26939 |
| NCI | Agilent_44K | 172 | adenocarcinoma, squamous cell & large cell | | Ref 22 http://research.agendia.com/ |
| Korea | HG-U133 + 2 | 138 | adenocarcinoma, squamous cell carcinoma | MAS5 normalized one channel intensitis are 2 based log transformed, data matrix is low (gene) median centered, column (sample) standardized.[30] | Ref 23 GSE8894 |
| Expo | HG-U133 + 2 | 130 | all histology subtypes | | Ref 24 GSE2109 |
| French | HG-U133 + 2 | 307 | all histology subtypes | | Ref 25 GSE30219 |
| Duke | HG-U133 + 2 | 118 | adenocarcinoma, squamous cell carcinoma | | Ref 26 GSE3141 |
| UNC | FFPE tissue RT-PCR | 78 | adenocarcinoma, squamous cell carcinoma, small cell, & carcinoid | FFPE sample gene expression data was scaled to align gene variance with Wilkerson et al. data[21]. A gene-specific scaling factor was calculated that took into account label frequency differences between the data sets. | Ref 27 Supplemental File #1 |

TABLE 13

| Sample | Label |
|---|---|
| VELO001 | Squamous.Cell.Carcinoma |
| VELO002 | Squamous.Cell.Carcinoma |
| VELO004 | Adenocarcinoma |
| VELO006 | Squamous.Cell.Carcinoma |
| VELO007 | Squamous.Cell.Carcinoma |
| VELO008 | Squamous.Cell.Carcinoma |
| VELO010 | Squamous.Cell.Carcinoma |
| VELO011 | Squamous.Cell.Carcinoma |
| VELO012 | Squamous.Cell.Carcinoma |
| VELO013 | Squamous.Cell.Carcinoma |
| VELO014 | Squamous.Cell.Carcinoma |
| VELO015 | Adenocarcinoma |
| VELO016 | Squamous.Cell.Carcinoma |
| VELO017 | Squamous.Cell.Carcinoma |
| VELO018 | Squamous.Cell.Carcinoma |
| VELO019 | Squamous.Cell.Carcinoma |
| VELO020 | Adenocarcinoma |
| VELO021 | Adenocarcinoma |
| VELO022 | Adenocarcinoma |
| VELO023 | Adenocarcinoma |
| VELO024 | Adenocarcinoma |
| VELO025 | Adenocarcinoma |
| VELO026 | Adenocarcinoma |
| VELO027 | Adenocarcinoma |
| VELO028 | Adenocarcinoma |
| VELO029 | Adenocarcinoma |
| VELO030 | Adenocarcinoma |
| VELO031 | Adenocarcinoma |
| VELO032 | Adenocarcinoma |
| VELO033 | Adenocarcinoma |
| VELO034 | Adenocarcinoma |
| VELO035 | Adenocarcinoma |
| VELO036 | Adenocarcinoma |
| VELO037 | Adenocarcinoma |
| VELO038 | Squamous.Cell.Carcinoma |
| VELO039 | Squamous.Cell.Carcinoma |
| VELO040 | Squamous.Cell.Carcinoma |
| VELO042 | Squamous.Cell.Carcinoma |
| VELO044 | Squamous.Cell.Carcinoma |
| VELO046 | Squamous.Cell.Carcinoma |
| VELO048 | Squamous.Cell.Carcinoma |
| VELO049 | Squamous.Cell.Carcinoma |
| VELO050 | Adenocarcinoma |
| VELO041 | Squamous.Cell.Carcinoma |
| VELO043 | Squamous.Cell.Carcinoma |
| VELO045 | Squamous.Cell.Carcinoma |
| VELO055 | Neuroendocrine |
| VELO056 | Neuroendocrine |
| VELO057 | Neuroendocrine |
| VELO058 | Neuroendocrine |
| VELO059 | Neuroendocrine |
| VELO060 | Neuroendocrine |
| VELO061 | Neuroendocrine |
| VELO062 | Neuroendocrine |
| VELO063 | Neuroendocrine |
| VELO064 | Neuroendocrine |
| VELO065 | Neuroendocrine |
| VELO066 | Neuroendocrine |
| VELO067 | Neuroendocrine |
| VELO068 | Neuroendocrine |
| VELO069 | Neuroendocrine |
| VELO070 | Neuroendocrine |
| VELO071 | Neuroendocrine |
| VELO072 | Neuroendocrine |
| VELO073 | Neuroendocrine |
| VELO074 | Neuroendocrine |
| VELO075 | Neuroendocrine |
| VELO076 | Neuroendocrine |
| VELO077 | Neuroendocrine |
| VELO078 | Neuroendocrine |
| VELO079 | Neuroendocrine |
| VELO080 | Neuroendocrine |
| VELO081 | Neuroendocrine |
| VELO082 | Neuroendocrine |
| VELO083 | Neuroendocrine |
| VELO084 | Neuroendocrine |
| VELO085 | Neuroendocrine |

Pathology review was only possible for the FFPE lung tumor cohort in which additional sections were collected and imaged. Two contiguous sections from each sample were Hematoxylin & Eosin (H&E) stained and scanned using an Aperio™ ScanScope® slide scanner (Aperio Technologies, Vista, Calif.). Virtual slides were viewable at magnifications equivalent to 32 to 320 objectives (340 magnifier). Pathologist review was blinded to the original clinical diagnosis and to the gene expression-based subtype classification. Pathology review-based histological subtype calls were compared to the original diagnosis (n=78). Agreement of pathology review was defined as those samples for which both slides were assigned the same subtype as the original diagnosis.

All statistical analyses were conducted using R 3.0.2 software (http://cran.R-project.org). Data analyses were conducted separately for FF and for FFPE tumor samples.

Fresh Frozen Dataset Analysis:

Datasets were normalized as described in Table 12. The Affymetrix dataset served as the training set for calculation of AD, carcinoid, SCC, and SQC gene centroids according to methods described previously (Wilkerson et al. PLoS ONE. 2012; 7(5) e36530. Doi:10.1371/journal.pone.0036530; Wilkerson et al. J Molec Diagn 2013; 15:485-497, each of which is incorporated by reference herein in its entirety for all purposes)

Affymetrix training gene centroids are provided in Table 14. The training set gene centroids were tested in normalized TCGA RNAseq gene expression and Agilent microarray gene expression data sets. Due to missing data from the public Agilent dataset, the Agilent evaluations were performed with a 47 gene classifier, rather than a 52 gene panel with exclusion of the following genes: CIB1 FOXH1, LIPE, PCAM1, TUBA1.

TABLE 14

| Gene | Adeno-carcinoma | Neuro-endocrine | Squamous.Cell.Carcinoma |
|---|---|---|---|
| ABCC5 | −0.453 | 0.3715 | 1.1245 |
| ACVR1 | 0.0475 | 0.3455 | −0.0465 |
| ALDH3B1 | 0.4025 | −0.638 | −0.401 |
| ANTXR1 | −0.0705 | −0.478 | 0.014 |
| BMP7 | −0.532 | −0.6265 | 0.6245 |
| CACNB1 | 0.024 | 0.157 | −0.039 |
| CAPG | 0.109 | −1.9355 | −0.0605 |
| CBX1 | −0.2045 | 0.745 | 0.187 |
| CDH5 | 0.391 | 0.145 | −0.352 |
| CDKN2C | −0.0045 | 1.496 | 0.004 |
| CHGA | −0.143 | 5.7285 | 0.1075 |
| CIB1 | 0.1955 | −0.261 | −0.065 |
| CLEC3B | 0.449 | 0.6815 | −0.3085 |
| CYB5B | 0.058 | 1.487 | −0.03 |
| DOK1 | 0.233 | −0.355 | −0.183 |
| DSC3 | −0.781 | −0.8175 | 4.3445 |
| FEN1 | −0.5025 | −0.0195 | 0.4035 |
| FOXH1 | −0.0405 | 0.1315 | −0.0105 |
| GJB5 | −1.388 | −1.5505 | 0.7685 |
| HOXD1 | 0.17 | −0.462 | −0.288 |
| HPN | 0.5335 | 0.444 | −0.736 |
| HYAL2 | 0.1775 | 0.073 | −0.143 |
| ICA1 | 0.3455 | 1.048 | −0.233 |
| ICAM5 | 0.13 | −0.145 | −0.12 |
| INSM1 | 0.0705 | 7.5695 | −0.0245 |
| ITGA6 | −0.709 | 0.029 | 1.074 |
| LGALS3 | 0.1805 | −1.1435 | −0.2305 |
| LIPE | 0.0065 | 0.5225 | −0.0015 |
| LRP10 | 0.2565 | −0.087 | −0.16 |
| MAPRE3 | −0.0245 | 0.6445 | −0.0025 |
| ME3 | 0.3085 | 0.3415 | −0.2915 |
| MGRN1 | 0.429 | 0.8075 | −0.3775 |
| MYBPH | 0.04 | −0.193 | −0.054 |
| MYO7A | 0.083 | −0.287 | −0.109 |
| NFIL3 | −0.332 | −1.0425 | 0.3095 |
| PAICS | −0.2145 | 0.3915 | 0.2815 |
| PAK1 | −0.112 | 0.6095 | 0.0965 |
| PCAM1 | 0.232 | −0.256 | −0.144 |
| PIK3C2A | 0.1505 | 0.597 | −0.021 |
| PLEKHA6 | 0.4465 | 2.0785 | −0.2615 |
| PSMD14 | −0.251 | 0.5935 | 0.1635 |
| SCD5 | −0.1615 | 0.06 | 0.13 |
| SFN | −0.789 | −3.026 | 0.91 |
| SIAH2 | −0.5795 | 0.1895 | 0.7175 |
| SNAP91 | −0.0255 | 3.818 | 0.003 |
| STMN1 | −0.0995 | 1.2095 | 0.1405 |

TABLE 14-continued

| Gene | Adeno-carcinoma | Neuro-endocrine | Squamous.Cell.Carcinoma |
|---|---|---|---|
| TCF2 | 0.2835 | −0.5175 | −0.4665 |
| TCP1 | −0.1685 | 0.9815 | 0.1985 |
| TFAP2A | −0.374 | −0.5075 | 0.3645 |
| TITF1 | 1.482 | 0.1525 | −1.2755 |
| TRIM29 | −1.0485 | −1.318 | 1.379 |
| TUBA1 | 0.155 | 1.71 | −0.07 |

TABLE 15

| Gene | Adeno-carcinoma | Neuro-endocrine | Squamous.Cell.Carcinoma |
|---|---|---|---|
| ABCC5 | −1.105993 | 0.53584995 | 0.28498017 |
| ACVR1 | −0.1780792 | 0.27746814 | −0.1331305 |
| ALDH3B1 | 2.21915126 | −1.0930042 | 0.82709803 |
| ANTXR1 | 0.14704523 | −0.0027417 | −0.1000265 |
| CACNB1 | −0.2032444 | 0.36015235 | −0.7588385 |
| CAPG | 0.52784999 | −0.6495988 | −0.0218352 |
| CBX1 | −0.5905845 | −0.0461076 | −0.2776489 |
| CDH5 | −0.1546498 | 0.53564677 | −0.9166437 |
| CDKN2C | −1.8382992 | −0.1614815 | −0.7501799 |
| CHGA | −6.2702431 | 8.18090411 | −7.4497926 |
| CIB1 | 0.29948877 | −0.1804507 | 0.06141265 |
| CLEC3B | 0.1454466 | 0.86221597 | −0.6686516 |
| CYB5B | −0.1957799 | 0.13060667 | −0.2393801 |
| DOK1 | 0.03629227 | 0.03029676 | −0.2861762 |
| DSC3 | 0.76811006 | −2.2230482 | 4.45353398 |
| FEN1 | −0.4100344 | −0.774919 | 0.19244803 |
| FOXH1 | 1.36365962 | −1.1539159 | 1.86758359 |
| GJB5 | 2.19942372 | −3.2908475 | 4.00132739 |
| HOXD1 | −0.069692 | −0.3296808 | 0.50430984 |
| HPN | 0.62232864 | −0.0416111 | −0.5391064 |
| HYAL2 | 0.47459315 | −0.2332929 | −0.0080073 |
| ICA1 | −0.8108302 | 1.25305275 | −2.1742476 |
| ICAM5 | 2.12506546 | −2.2078991 | 2.89691121 |
| INSM1 | −2.4346556 | 1.92393374 | −1.9749654 |
| ITGA6 | −0.7881662 | 0.36443897 | 0.54978058 |
| LGALS3 | −0.8270046 | 0.79512054 | −0.9453521 |
| LIPE | −0.2519692 | 0.29291064 | −0.2216243 |
| LRP10 | 0.09504093 | 0.14082188 | −0.4042101 |
| MAPRE3 | −0.6806204 | 1.2417945 | −0.5496704 |
| ME3 | 0.17668171 | 0.67674964 | −1.581183 |
| MGRN1 | −0.0839601 | 0.35069923 | −0.6885404 |
| MYBPH | 0.73519429 | −0.9569161 | 1.14344753 |
| MYO7A | 0.58098661 | −0.2096425 | 0.0488886 |
| NFIL3 | 0.22274434 | −0.337858 | 0.66234639 |
| PAICS | −0.2423309 | −0.1863934 | 0.39037381 |
| PAK1 | −0.3803406 | 0.15627507 | 0.0677904 |
| PCAM1 | 0.03655586 | 0.32457357 | −0.6957339 |
| PIK3C2A | −0.3868824 | 0.56861416 | −0.6629455 |
| PLEKHA6 | −0.4007847 | 1.31002812 | −1.9802266 |
| PSMD14 | −0.5115938 | 0.27513479 | −0.2847234 |
| SCD5 | −0.4770619 | −0.4338812 | 0.56043153 |
| SFN | 0.35719248 | −1.4361124 | 2.34498532 |
| SIAH2 | −0.4222382 | −0.3853078 | 0.43237756 |
| SNAP91 | −5.5499562 | 4.65742276 | −2.5441741 |
| STMN1 | −1.4075058 | 0.49776156 | −1.017481 |
| TCF2 | 1.96819785 | −0.4121173 | −0.6555613 |
| TCP1 | −2.9255287 | 2.322428 | −2.3059797 |
| TFAP2A | 2.02528144 | −2.9053184 | 3.62844763 |
| TITF1 | 0.46476685 | −9.82E−05 | −1.7079242 |
| TRIM29 | −1.6554559 | −0.6463626 | 2.94818107 |
| TUBA1 | 1.77126501 | −2.0395783 | 1.58902579 |

Evaluation of the Affymetrix data was performed using Leave One Out (LOO) cross validation. Spearman correlations were calculated for tumor test sample to the Affymetrix gene expression training centroids. Tumors were assigned a genomic-defined histologic type (AD, SQC, or NE) corresponding to the maximally correlated centroids. Correct predictions were defined as LSP calls matching the tumor's original histologic diagnosis. Percent agreement was defined as the number of correct predictions divided by the number of total predictions and an agreement kappa statistic was calculated.

qRT-PCR from FFPE Sample Analysis:

Previously published training centroids (Wilkerson et al. J Molec Diagn 2013; 15:485-497, incorporated by reference herein), calculated from qRT-PCR data of FFPE lung tumor samples, were cross-validated in this new sample set of qRT-PCR gene expression from FFPE lung tumor tissue. Wilkerson et al. AD and SQC centroids were used as published (Wilkerson et al. J Molec Diagn 2013; 15:485-497, incorporated by reference herein). Neuroendocrine gene centroids were calculated similarly using published gene expression data (n=130) (Wilkerson et al. J Molec Diagn 2013; 15:485-497, incorporated by reference herein). The Wilkerson et al. gene centroids (Wilkerson et al. J Molec Diagn 2013; 15:485-497, incorporated by reference herein) for the FFPE tissue evaluation are included in Table 15. FFPE sample gene expression data was scaled to align gene variance with Wilkerson et al. data. A gene-specific scaling factor was calculated that took into account label frequency differences between the data sets. Gene expression data was then median centered, sign flipped (high Ct=low abundance), and scaled using the gene specific scaling factor. Subtype was predicted by correlating each sample with the 3 subtype centroids and assignment of the subtype with the highest correlation centroid (Spearman correlation).

Ten lung tumor gene expression datasets including nine FF plus one new FFPE qRT-PCR gene expression dataset were combined into four platform-specific data sets (Affymetrix, Agilent, Illumina RNAseq, and qRT-PCR). For the datasets where clinical information was available, the patient population was diverse and included smokers and nonsmokers with tumors ranging from Stage 1-Stage IV. Sample characteristics and lung cancer diagnoses of the datasets used in this study are included in Table 16. After exclusion of samples without a definitive diagnosis of AD, SQC, SCC, or carcinoid, and exclusion of 1 FFPE sample that failed qRT-PCR analysis, the following samples were available for further data analysis: Affymetrix (n=538), Agilent (n=322), Illumina RNAseq (n=951) and qRT-PCR (n=77).

TABLE 16

| Characteristic | TCGA RNA seq | Agilent | Affymetrix | UNC FFPE |
|---|---|---|---|---|
| Total # of samples | 1062 | 344 | 693 | 78 |
| Tissue Preservation | Fresh Frozen | Fresh Frozen | Fresh Frozen | FFPE |
| Tumor specimen histology | | | | |
| Adenocarcinoma | 468 | 174 | 264 | 21 |
| Carcinoid | 0 | 0 | 23 | 15 |
| Small Cell Carcinoma | 0 | 0 | 24 | 16 |
| Squamous Cell Carcinoma | 483 | 148 | 227 | 25 |
| Other(excluded from analysis) | 111 | 22 | 155 | 01 |
| Gender | | | | |
| Female/Male/NA | 285/366/300 | 87/85/150 | 151/386/1 | NA |
| Age at Diagnosis | | | | |
| Median/(Range) | 67/(38-88) | 66/(37-90) | 65/(13-85) | NA |
| Age not available | 323 | 0 | 2 | NA |
| Stage | | | | |
| I | 355 | NA | NA | NA |
| II | 146 | NA | NA | NA |
| III | 119 | NA | NA | NA |

TABLE 16-continued

| Characteristic | TCGA RNA seq | Agilent | Affymetrix | UNC FFPE |
|---|---|---|---|---|
| IV | 26 | NA | NA | NA |
| Stage not available | 305 | 322 | 538 | 77 |
| Smoking | | | | |
| Smoker | 386 | NA | NA | NA |
| Nonsmoker | 39 | NA | NA | NA |
| Smoking status not available | 526 | 322 | 538 | 77 |

Figure 2:
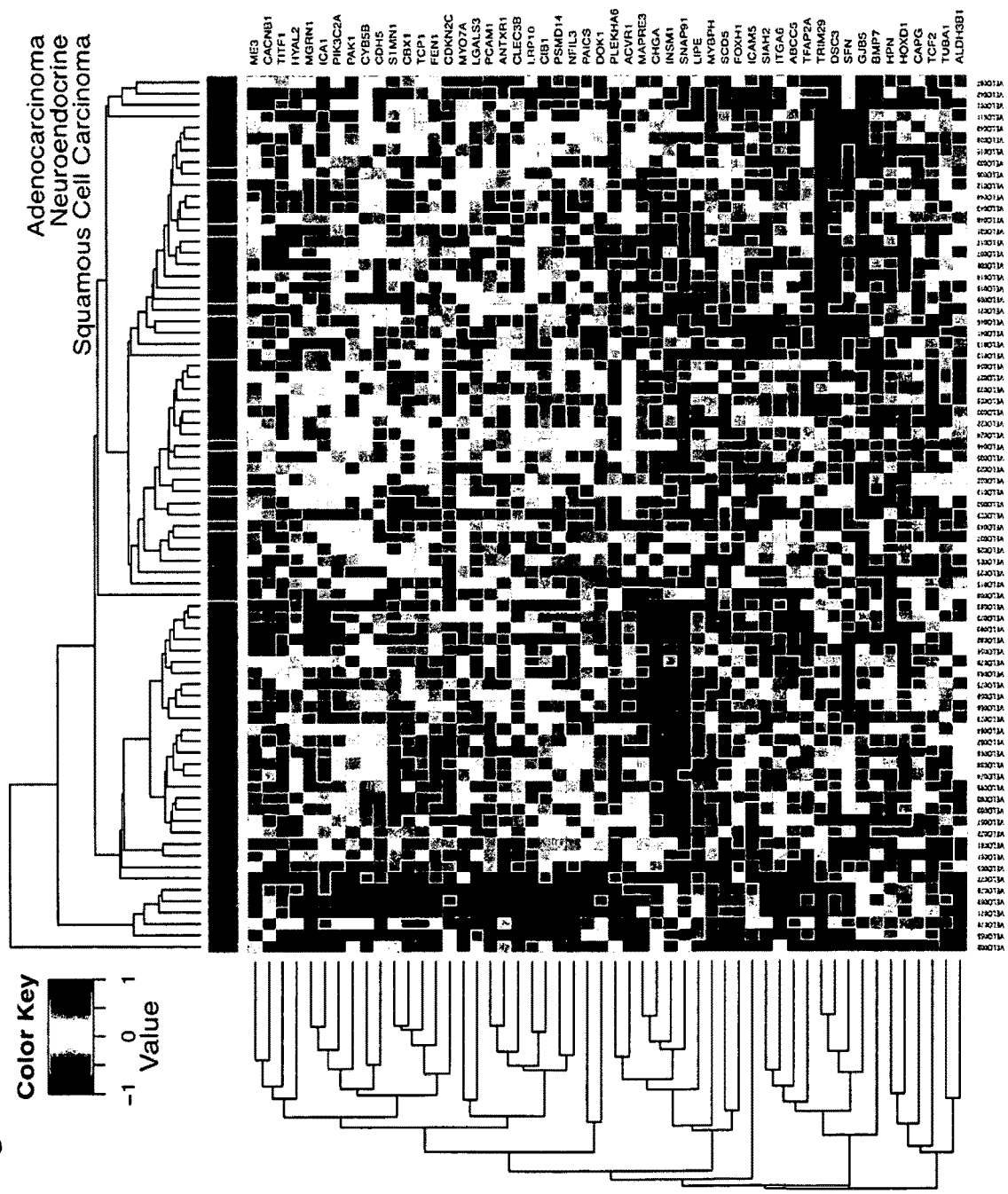
FIG. 2 is a heatmap of gene expression hierarchical clustering for FFPE RT-PCR gene expression dataset.

As a means of de novo evaluation of the new FFPE data set, we performed hierarchical clustering of LSP gene expression from the FFPE archived samples (n=77); as expected, this analysis demonstrated three clusters/subtypes corresponding to AD, SQC, and NE (FIG. 2). The predetermined LSP 3-subtype centroid predictor was then applied to all 4 datasets, and results were compared with tumor morphologic classifications. Percent agreement and Fleiss' kappa were calculated for each dataset (Table 17). The percent agreement ranged from 78%-91% and kappa's from 0.57-0.85.

As another means of assessing independent pathology agreement, the agreement of blinded pathology review of the 77 FFPE lung tumors with the original morphologic diagnosis was found to be 82% (63/77). In 12/77 cases, blinded duplicate slides provided conflicting results and in 10/77 cases, at least one of the duplicates had a non-definitive pathological subtype classification of "Adenosquamous", "Large Cell", or "High grade poorly differentiated carcinoma". Comparison of the original morphologic diagnosis, blinded pathology review, and gene expression LSP subtype call for each of the 77 samples is shown in FIG. 3. Details of discordant sample overlap (i.e., 6 samples where tumor subtype disagreed with original morphology diagnosis by both path review and gene expression LSP call) are provided in Table 18. Overall, these concordance values of LSP relative to the original pathology calls were at least as great as the concordance between any two pathologists (Grilley et al. Arch Pathol Lab Med 2013; 137: 32-40; Thunnissen et al. Virchows Arch 2012; 461(6): 629-38. Doi: 10.1007/s00428-012-1234-x. Epub 2012 Oct. 12; Thunnissen et al. Mod Pathol 2012; 25(12):1574-83. Doi: 10.1038/modpathol.2012.106; each of which is incorporated by reference herein for all purposes) thus suggesting that the assay described herein performs at least as well as a trained pathologist.

In this study, LSP provided reliable subtype classifications, validating its performance across multiple gene expression platforms, and even when using FFPE specimens. Hierarchical clustering of the newly assayed FFPE samples demonstrated good separation of the 3 subtypes (AC, SQC, and NE) based on the levels of 52 classifier biomarkers. Concordance with morphology diagnosis when using the LSP centroids was greatest in the TCGA RNAseq dataset (agreement=91%), possibly due to the very extensive pathology review and accuracy of the histologic diagnosis associated with TCGA samples as compared to other datasets. Agreement was lowest (78%) in the Agilent dataset, which may have been affected by the reduced number of genes that were available for that analysis. Overall, the LSP assay displayed a higher concordance with the original morphology diagnosis than the pathology review in all datasets except in the Agilent dataset, in which only 47 genes, rather than 52, were present for the analysis.

In the FFPE samples where blinded pathology re-review was possible, results suggested that pathology calls were not always consistent with the original diagnosis, nor were they necessarily consistent in the duplicate slides provided from each sample. For a subset of samples (n=6), both the pathology re-review and the LSP gene expression analysis suggested the same alternate diagnosis, leading one to question the accuracy of the original morphologic diagnosis, which was our "gold standard".

In this study, there were a low number of NE tumor samples in the Affymetrix dataset, and an absence of NE samples in both the Agilent and TCGA datasets. This was partially overcome by a relatively high number of NE samples in the FFPE sample set (31/77), thus providing a good test of the LSP signature's ability to identify NE samples. Another limitation of the study relates to the blinded pathology re-review. The blinded pathology review was based on two imaged sections and did not reflect usual histology standard practice where multiple sections/blocks and potentially IHC stains would have been available to make a diagnosis.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

---

What is claimed is:

1. A method of detecting biomarkers in a lung tissue sample obtained from a human patient, the method comprising measuring nucleic acid expression levels for every classifier biomarker in a group of classifier biomarkers consisting of only (a) CDH5, PECAM1, PAICS, PAK1, TFAP2A, CDKN2C, INSM1, STMN1, ACVR1, CIB1, LRP10, CHGA, MAPRE3, SNAP91, CAPG, LGALS3, SFN, PSMD14, CBX1, NFIL3, SCD5, HOXD1, ICAM5, FOXH1, CACNB1, TCF2, FEN1, TUBA1, CYB5B, PIK3C2A, ANTXR1, LIPE, MYBPH, DOK1, SIAH2, ITGA6, ICA1, TTF1, HPN, TRIM29, DSC3, MGRN1, HYAL2, MYO7A, ABCC5, GJB5, PLEKHA6, ME3, and ALDH3B1 or (b) CDH5, CLEC3B, PAICS, PAK1, TFAP2A, CDKN2C, INSM1, STMN1, ACVR1, LRP10, CHGA, MAPRE3, SNAP91, CAPG, LGALS3, SFN, PSMD14, CBX1, NFIL3, SCD5, HOXD1, ICAM5, CACNB1, TCF2, TCP1, FEN1, CYB5B, PIK3C2A, ANTXR1, MYBPH, DOK1, SIAH2, ITGA6, ICA1, TTF1, HPN, TRIM29, DSC3, MGRN1, HYAL2, MYO7A, ABCC5, GJB5, PLEKHA6, ME3 and ALDH3B1 in the lung tissue sample, wherein the measuring is performed using an amplification, hybridization and/or sequencing assay.

2. The method of claim 1, wherein the lung tissue sample was previously diagnosed as lung cancer by histological examination.

3. The method of claim 1, wherein the measuring is performed using an amplification assay, wherein the amplification assay is qRT-PCR.

4. The method of claim 3, wherein the measuring of the nucleic acid expression levels comprises using at least one pair of oligonucleotide primers per each of the classifier biomarkers of only (a) or (b).

5. The method of claim 4, further comprising comparing the nucleic acid expression levels of every classifier biomarker in a group of classifier biomarkers consisting of only (a) or (b) to the expression levels of every classifier biomarker in a group of classifier biomarkers consisting of only (a) or (b) from a reference sample.

6. The method of claim 2, wherein the lung cancer is adenocarcinoma, squamous cell carcinoma or neuroendocrine.

7. The method of claim 2, wherein the lung cancer is adenocarcinoma, squamous cell carcinoma, small cell carcinoma or carcinoid.

8. The method of claim 5, wherein the reference sample is a normal sample from an individual that is healthy.

9. The method of claim 5, wherein the reference sample is from an individual known to have a lung cancer subtype.

10. The method of claim 1, wherein the measuring is performed using a hybridization assay, wherein the hybridization assay comprises:
(a) probing the nucleic acid expression levels of the classifier biomarkers in the group of classifier biomarkers consisting of only (a) or (b) in the lung cancer sample obtained from the patient, wherein the probing comprises:
(i) mixing the sample with oligonucleotides that are complementary to portions of nucleic acid molecules of the classifier biomarkers of only (a) or (b) under conditions suitable for hybridization of the oligonucleotides to their complements;
(ii) detecting whether hybridization occurs between the oligonucleotides to their complements;
(iii) obtaining hybridization values of the classifier biomarkers based on the detecting; and
(b) comparing the hybridization values of the classifier biomarkers to reference hybridization value(s) from at least one sample training set, wherein the at least one sample training set comprises hybridization values from a reference adenocarcinoma sample, hybridization values from a reference squamous cell carcinoma sample, hybridization values from a reference neuroendocrine sample, hybridization values from a reference small cell carcinoma sample, hybridization values from a reference carcinoid sample, or a combination thereof.

11. The method of claim 10, wherein the comparing comprises determining a correlation between the hybridization values of the classifier biomarkers and the reference hybridization values.

12. The method of claim 10, wherein the comparing further comprises determining an average expression ratio of the biomarkers and comparing the average expression ratio to an average expression ratio of the biomarkers obtained from the references values in the sample training set.

13. The method of claim 10, wherein the hybridization comprises hybridization of a cDNA probe to a cDNA biomarker, thereby forming a non-natural complex.

14. The method of claim 10, wherein the hybridization comprises hybridization of a cDNA probe to an mRNA biomarker, thereby forming a non-natural complex.

15. The method of claim 1, wherein the lung tissue sample is selected from a formalin-fixed, paraffin-embedded (FFPE) lung tissue sample, fresh and a frozen tissue sample.

* * * * *